US007442371B2

(12) United States Patent
Yu et al.

(10) Patent No.: US 7,442,371 B2
(45) Date of Patent: Oct. 28, 2008

(54) RECOMBINANT HUMAN ALBUMIN-ERYTHROPOIETIN FUSION PROTEINS WITH LONG-LASTING BIOLOGICAL EFFECTS

(76) Inventors: Zailin Yu, 334 E. 54th St., Apt. # 3F, New York, NY (US) 10022; Yan Fu, 334 E. 54th St., Apt# 3F, New York, NY (US) 10022

( * ) Notice: Subject to any disclaimer, the term of this patent is extended or adjusted under 35 U.S.C. 154(b) by 0 days.

(21) Appl. No.: 11/825,686

(22) Filed: Jul. 8, 2007

(65) Prior Publication Data

US 2008/0009446 A1 Jan. 10, 2008

Related U.S. Application Data

(63) Continuation of application No. 10/609,346, filed on Jun. 26, 2003, now Pat. No. 7,244,833.

(60) Provisional application No. 60/392,948, filed on Jul. 1, 2002.

(51) Int. Cl.
*C07K 14/52* (2006.01)
*A61K 38/19* (2006.01)
(52) U.S. Cl. .................. 424/85.1; 530/351; 530/402
(58) Field of Classification Search .................. None
See application file for complete search history.

(56) References Cited

U.S. PATENT DOCUMENTS 5,116,964 A * 5/1992 Capon et al. ............... 536/23.5
5,547,933 A   8/1996 Lin
7,141,547 B2 * 11/2006 Rosen et al. ............... 514/12

FOREIGN PATENT DOCUMENTS

WO WO-01/79271 A1 10/2001
WO WO-01/79442 A2 10/2001

OTHER PUBLICATIONS

Mikayama et al. Proc. Natl. Acad. Sci. USA vol. 90, pp. 10056-10060.*
Voet et al. Biochemistry John Wiley & Sons, Inc., pp. 126-128 and 228-234.*
Pennathur-Das et al., "Evidence for the Presenece of CFU-E with Increased In-Vitro Sensitivity to Erythropoietin in Sickle Cell Anemia", Blood, vol. 63, No. 5, 1984: pp. 1168-1171.
Tong et al., "Formation of Erythrocyte Membrane Proteins during Erythropoietin-induced Differentiation", Journal of Biological Chemistry, vol. 256, No. 24, 1981, pp. 12666-12672.
Lin et al., "Cloning and Expression of the Human Erythropoietin Gene", Proc. Natl. Acad. Sci. USA, vol. 82, 1985, pp. 7580-7584.
Morgan et al., "Erythropoietin and Renal Function in Sickle-Cell Disease", British Medical Journal, vol. 285, 1982, pp. 1686-1688.
Korhonen et al., "Expression of bovine P-lactoglobulinhuman erythropoietin fusion protein in the milk of transgenic mice and rabbits", Eur. J. Biochem. (1997), vol. 245, p. 482-489.

* cited by examiner

*Primary Examiner*—Prema Mertz
(74) *Attorney, Agent, or Firm*—Yi Li

(57) ABSTRACT

Compositions, kits and methods are provided for promoting general health or for prevention or treatment of diseases by using novel recombinant fusion proteins of human serum albumin (HSA) and bioactive molecules. The bioactive molecules may be a protein or peptide having a biological function in vitro or in vivo, and preferably, having a therapeutic activity when administered to a human. By fusing the bioactive molecule to HSA, stability of the bioactive molecule in vivo can be improved and the therapeutic index increased due to reduced toxicity and longer-lasting therapeutic effects in vivo. In addition, manufacturing processes are provided for efficient, cost-effective production of these recombinant proteins in yeast.

7 Claims, 20 Drawing Sheets

Figure 1

(A) Seq ID No. 1: DNA Sequence Encoding HSA-hIL-11

ATGAAGTGGGTAACCTTTATTTCCCTTCTTTTTCTCTTTAGCTCGGCTTATTCCAGGGGTGTGTTTCGTCG
AGATGCACACAAGAGTGAGGTTGCTCATCGGTTTAAAGATTTGGGAGAAGAAAATTTCAAAGCCTTGGTGT
TGATTGCCTTTGCTCAGTATCTTCAGCAGTGTCCATTTGAAGATCATGTAAAATTAGTGAATGAAGTAACT
GAATTTGCAAAAACATGTGTTGCTGATGAGTCAGCTGAAAATTGTGACAAATCACTTCATACCCTTTTGG
AGACAAATTATGCACAGTTGCAACTCTTCGTGAAACCTATGGTGAAATGGCTGACTGCTGTGCAAAACAAG
AACCTGAGAGAAATGAATGCTTCTTGCAACACAAAGATGACAACCCAAACCTCCCCCGATTGGTGAGACCA
GAGGTTGATGTGATGTGCACTGCTTTTCATGACAATGAAGAGACATTTTTGAAAAAATACTTATATGAAAT
TGCCAGAAGACATCCTTACTTTTATGCCCCGGAACTCCTTTTCTTTGCTAAAAGGTATAAAGCTGCTTTTA
CAGAATGTTGCCAAGCTGCTGATAAAGCTGCCTGCCTGTTGCCAAAGCTCGATGAACTTCGGGATGAAGGG
AAGGCTTCGTCTGCCAAACAGAGACTCAAGTGTGCCAGTCTCCAAAAATTTGGAGAAAGAGCTTTCAAAGC
ATGGGCAGTAGCTCGCCTGAGCCAGAGATTTCCCAAAGCTGAGTTTGCAGAAGTTTCCAAGTTAGTGACAG
ATCTTACCAAAGTCCACACGGAATGCTGCCATGGAGATCTGCTTGAATGTGCTGATGACAGGCGGACCTT
GCCAAGTATATCTGTGAAAATCAAGATTCGATCTCCAGTAAACTGAAGGAATGCTGTGAAAAACCTCTGTT
GGAAAAATCCCACTGCATTGCCGAAGTGGAAAATGATGAGATGCCTGCTGACTTGCCTTCATTAGCTGCTG
ATTTTGTTGAAAGTAAGGATGTTTGCAAAAACTATGCTGAGGCAAAGGATGTCTTCCTGGGCATGTTTTTG
TATGAATATGCAAGAAGGCATCCTGATTACTCTGTCGTGCTGCTGCTGAGACTTGCCAAGACATATGAAAC
CACTCTAGAGAAGTGCTGTGCCGCTGCAGATCCTCATGAATGCTATGCCAAAGTGTTCGATGAATTTAAAC
CTCTTGTGGAAGAGCCTCAGAATTTAATCAAACAAAATTGTGAGCTTTTTGAGCAGCTTGGAGAGTACAAA
TTCCAGAATGCGCTATTAGTTCGTTACACCAAGAAAGTACCCCAAGTGTCAACTCCAACTCTTGTAGAGGT
CTCAAGAAACCTAGGAAAAGTGGGCAGCAAATGTTGTAAACATCCTGAAGCAAAAGAATGCCCTGTGCAG
AAGACTATCTATCCGTGGTCCTGAACCAGTTATGTGTGTTGCATGAGAAAACGCCAGTAAGTGACAGAGTC
ACCAAATGCTGCACAGAATCCTTGGTGAACAGGCGACCATGCTTTTCAGCTCTGGAAGTCGATGAAACATA
CGTTCCCAAAGAGTTTAATGCTGAAACATTCACCTTCCATGCAGATATATGCACACTTTCTGAGAAGGAGA
GACAAATCAAGAAACAAACTGCACTTGTTGAGCTTGTGAAACACAAGCCCAAGGCAACAAAAGAGCAACTG
AAAGCTGTTATGGATGATTTCGCAGCTTTTGTAGAGAAGTGCTGCAAGGCTGACGATAAGGAGACCTGCTT
TGCCGAGGAGGGTAAAAAACTTGTTGCTGCAAGTCAAGCTGCCTTAGGCTTAGCTCCCATGACCCAGACAA
CGTCCTTGAAGACAAGCTGGGTTAACTGCTCTAACATGATCGATGAAATTATAACACACTTAAAGCAGCCA
CCTTTGCCTTTGCTGGACTTCAACAACCTCAATGGGGAAGACCAAGACATTCTGATGGAAAATAACCTTCG
AAGGCCAAACCTGGAGGCATTCAACAGGGCTGTCAAGAGTTTACAGAACGCATCAGCAATTGAGAGCATTC
TTAAAAATCTCCTGCCATGTCTGCCCCTGGCCACGGCCGCACCCACGCGACATCCAATCCATATCAAGGAC
GGTGACTGGAATGAATTCCGGAGGAAACTGACGTTCTATCTGAAAACCCTTGAGAATGCGCAGGCTCAACA
GACGACTTTGAGCCTCGCGATCTTTTAG (B) Seq ID No. 2. Amino Acid Sequence of HSA-hIL-11 Fusion Protein DAHKSEVAHRFKDLGEENFKALVLIAFAQYLQQCPFEDHVKLVNEVTEFAKTCVADESAENCDKSLHTLFG
DKLCTVATLRETYGEMADCCAKQEPERNECFLQHKDDNPNLPRLVRPEVDVMCTAFHDNEETFLKKYLYEI
ARRHPYFYAPELLFFAKRYKAAFTECCQAADKAACLLPKLDELRDEGKASSAKQRLKCASLQKFGERAFKA
WAVARLSQRFPKAEFAEVSKLVTDLTKVHTECCHGDLLECADDRADLAKYICENQDSISSKLKECCEKPLL
EKSHCIAEVENDEMPADLPSLAADFVESKDVCKNYAEAKDVFLGMFLYEYARRHPDYSVVLLLRLAKTYET
TLEKCCAAADPHECYAKVFDEFKPLVEEPQNLIKQNCELFEQLGEYKFQNALLVRYTKKVPQVSTPTLVEV
SRNLGKVGSKCCKHPEAKRMPCAEDYLSVVLNQLCVLHEKTPVSDRVTKCCTESLVNRRPCFSALEVDETY
VPKEFNAETFTFHADICTLSEKERQIKKQTALVELVKHKPKATKEQLKAVMDDFAAFVEKCCKADDKETCF
AEEGKKLVAASQAALGLPGPPPGPPRVSPDPRAELDSTVLLTRSLLADTRQLAAQLRDKFPADGDHNLDSL
PTLAMSAGALGALQLPGVLTRLRADLLSYLRHVQWLRRAGGSSLKTLEPELGTLQARLDRLLRRLQLLMSR
LALPQPPPDPPAPPLAPPSSAWGGIRAAHAILGGLHLTLDWAVRGLLLLKTRL

Figure 1-continued (C) Seq ID No. 3. DNA Sequence Encoding HSA-hIL-3

```
ATGAAGTGGGTAACCTTTATTTCCCTTCTTTTTCTCTTTAGCTCGGCTTATTCCAGGGGTGTGTTTCGTCG
AGATGCACACAAGAGTGAGGTTGCTCATCGGTTTAAAGATTTGGGAGAAGAAAATTTCAAAGCCTTGGTGT
TGATTGCCTTTGCTCAGTATCTTCAGCAGTGTCCATTTGAAGATCATGTAAAATTAGTGAATGAAGTAACT
GAATTTGCAAAAACATGTGTTGCTGATGAGTCAGCTGAAAATTGTGACAAATCACTTCATACCCTTTTTGG
AGACAAATTATGCACAGTTGCAACTCTTCGTGAAACCTATGGTGAAATGGCTGACTGCTGTGCAAAACAAG
AACCTGAGAGAAATGAATGCTTCTTGCAACACAAAGATGACAACCCAAACCTCCCCCGATTGGTGAGACCA
GAGGTTGATGTGATGTGCACTGCTTTTCATGACAATGAAGAGACATTTTTGAAAAAATACTTATATGAAAT
TGCCAGAAGACATCCTTACTTTTATGCCCCGGAACTCCTTTTCTTTGCTAAAAGGTATAAAGCTGCTTTTA
CAGAATGTTGCCAAGCTGCTGATAAAGCTGCCTGCCTGTTGCCAAAGCTCGATGAACTTCGGGATGAAGGG
AAGGCTTCGTCTGCCAAACAGAGACTCAAGTGTGCCAGTCTCCAAAAATTTGGAGAAAGAGCTTTCAAAGC
ATGGGCAGTAGCTCGCCTGAGCCAGAGATTTCCCAAAGCTGAGTTTGCAGAAGTTTCCAAGTTAGTGACAG
ATCTTACCAAAGTCCACACGGAATGCTGCCATGGAGATCTGCTTGAATGTGCTGATGACAGGGCGGACCTT
GCCAAGTATATCTGTGAAAATCAAGATTCGATCTCCAGTAAACTGAAGGAATGCTGTGAAAAACCTCTGTT
GGAAAAAATCCCACTGCATTGCCGAAGTGGAAAATGATGAGATGCCTGCTGACTTGCCTTCATTAGCTGCTG
ATTTTGTTGAAAGTAAGGATGTTTGCAAAAACTATGCTGAGGCAAAGGATGTCTTCCTGGGCATGTTTTTG
TATGAATATGCAAGAAGGCATCCTGATTACTCTGTCGTGCTGCTGCTGAGACTTGCCAAGACATATGAAAC
CACTCTAGAGAAGTGCTGTGCCGCTGCAGATCCTCATGAATGCTATGCCAAAGTGTTCGATGAATTTAAAC
CTCTTGTGGAAGAGCCTCAGAATTTAATCAAACAAAATTGTGAGCTTTTTGAGCAGCTTGGAGAGTACAAA
TTCCAGAATGCGCTATTAGTTCGTTACACCAAGAAAGTACCCCAAGTGTCAACTCCAACTCTTGTAGAGGT
CTCAAGAAACCTAGGAAAAGTGGGCAGCAAATGTTGTAAACATCCTGAAGCAAAAAGAATGCCCTGTGCAG
AAGACTATCTATCCGTGGTCCTGAACCAGTTATGTGTGTTGCATGAGAAAACGCCAGTAAGTGACAGAGTC
ACCAAATGCTGCACAGAATCCTTGGTGAACAGGCGACCATGCTTTTCAGCTCTGGAAGTCGATGAAACATA
CGTTCCCAAAGAGTTTAATGCTGAAACATTCACCTTCCATGCAGATATATGCACACTTTCTGAGAAGGAGA
GACAAATCAAGAAACAAACTGCACTTGTTGAGCTTGTGAAACACAAGCCCAAGGCAACAAAAGAGCAACTG
AAAGCTGTTATGGATGATTTCGCAGCTTTTGTAGAGAAGTGCTGCAAGGCTGACGATAAGGAGACCTGCTT
TGCCGAGGAGGGTAAAAAACTTGTTGCTGCAAGTCAAGCTGCCTTAGGCTTAGCTCCCATGACCCAGACAA
CGTCCTTGAAGACAAGCTGGGTTAACTGCTCTAACATGATCGATGAAATTATAACACACTTAAAGCAGCCA
CCTTTGCCTTTGCTGGACTTCAACAACCTCAATGGGGAAGACCAAGACATTCTGATGGAAAATAACCTTCG
AAGGCCAAACCTGGAGGCATTCAACAGGGCTGTCAAGAGTTTACAGAACGCATCAGCAATTGAGAGCATTC
TTAAAAATCTCCTGCCATGTCTGCCCCTGGCCACGGCCGCACCCACGCGACATCCAATCCATATCAAGGAC
GGTGACTGGAATGAATTCCGGAGGAAACTGACGTTCTATCTGAAAACCCTTGAGAATGCGCAGGCTCAACA
GACGACTTTGAGCCTCGCGATCTTTTAG
```

(D) Seq ID No. 4. Amino Acid Sequence of HSA-hIL-3 Fusion Protein

```
DAHKSEVAHRFKDLGEENFKALVLIAFAQYLQQCPFEDHVKLVNEVTEFAKTCVADESAENCDKSLHTLFG
DKLCTVATLRETYGEMADCCAKQEPERNECFLQHKDDNPNLPRLVRPEVDVMCTAFHDNEETFLKKYLYEI
ARRHPYFYAPELLFFAKRYKAAFTECCQAADKAACLLPKLDELRDEGKASSAKQRLKCASLQKFGERAFKA
WAVARLSQRFPKAEFAEVSKLVTDLTKVHTECCHGDLLECADDRADLAKYICENQDSISSKLKECCEKPLL
EKSHCIAEVENDEMPADLPSLAADFVESKDVCKNYAEAKDVFLGMFLYEYARRHPDYSVVLLLRLAKTYET
TLEKCCAAADPHECYAKVFDEFKPLVEEPQNLIKQNCELFEQLGEYKFQNALLVRYTKKVPEVSTPTLVEV
SRNLGKVGSKCCKHPEAKRMPCAEDYLSVVLNQLCVLHEKTPVSDRVTKCCTESLVNRRPCFSALEVDETY
VPKEFNAETFTFHADICTLSEKERQIKKQTALVELVKHKPKATKEQLKAVMDDFAAFVEKCCKADDKETCF
AEEGKKLVAASQAALGLAPMTQTTSLKTSWVNCSNMIDEIITHLKQPPLPLLDFNNLNGEDQDILMENNLR
RPNLEAFNRAVKSLQNASAIESILKNLLPCLPLATAAPTRHPIHIKDGDWNEFRRKLTFYLKTLENAQAQQ
TTLSLAIF
```

Figure 1-continued (E) Seq ID No. 5. DNA Sequence Encoding HSA-hEPO

```
ATGAAGTGGGTAACCTTTATTTCCCTTCTTTTTCTCTTTAGCTCGGCTTATTCCAGGGGTGTGTTTCGTCG
AGATGCACACAAGAGTGAGGTTGCTCATCGGTTTAAAGATTTGGGAGAAGAAAATTTCAAAGCCTTGGTGT
TGATTGCCTTTGCTCAGTATCTTCAGCAGTGTCCATTTGAAGATCATGTAAAATTAGTGAATGAAGTAACT
GAATTTGCAAAAACATGTGTTGCTGATGAGTCAGCTGAAAATTGTGACAAATCACTTCATACCCTTTTTGG
AGACAAATTATGCACAGTTGCAACTCTTCGTGAAACCTATGGTGAAATGGCTGACTGCTGTGCAAAACAAG
AACCTGAGAGAAATGAATGCTTCTTGCAACACAAAGATGACAACCCAAACCTCCCCCGATTGGTGAGACCA
GAGGTTGATGTGATGTGCACTGCTTTTCATGACAATGAAGAGACATTTTTGAAAAAATACTTATATGAAAT
TGCCAGAAGACATCCTTACTTTTATGCCCCGGAACTCCTTTTCTTTGCTAAAAGGTATAAAGCTGCTTTTA
CAGAATGTTGCCAAGCTGCTGATAAAGCTGCCTGCCTGTTGCCAAAGCTCGATGAACTTCGGGATGAAGGG
AAGGCTTCGTCTGCCAAACAGAGACTCAAGTGTGCCAGTCTCCAAAAATTTGGAGAAAGAGCTTTCAAAGC
ATGGGCAGTAGCTCGCCTGAGCCAGAGATTTCCCAAAGCTGAGTTTGCAGAAGTTTCCAAGTTAGTGACAG
ATCTTACCAAAGTCCACACGGAATGCTGCCATGGAGATCTGCTTGAATGTGCTGATGACAGGGCGGACCTT
GCCAAGTATATCTGTGAAAATCAAGATTCGATCTCCAGTAAACTGAAGGAATGCTGTGAAAAACCTCTGTT
GGAAAAATCCCACTGCATTGCCGAAGTGGAAAATGATGAGATGCCTGCTGACTTGCCTTCATTAGCTGCTG
ATTTTGTTGAAAGTAAGGATGTTTGCAAAAACTATGCTGAGGCAAAGGATGTCTTCCTGGGCATGTTTTTG
TATGAATATGCAAGAAGGCATCCTGATTACTCTGTCGTGCTGCTGCTGAGACTTGCCAAGACATATGAAAC
CACTCTAGAGAAGTGCTGTGCCGCTGCAGATCCTCATGAATGCTATGCCAAAGTGTTCGATGAATTTAAAC
CTCTTGTGGAAGAGCCTCAGAATTTAATCAAACAAAATTGTGAGCTTTTTGAGCAGCTTGGAGAGTACAAA
TTCCAGAATGCGCTATTAGTTCGTTACACCAAGAAAGTACCCCAAGTGTCAACTCCAACTCTTGTAGAGGT
CTCAAGAAACCTAGGAAAAGTGGGCAGCAAATGTTGTAAACATCCTGAAGCAAAAGAATGCCCTGTGCAG
AAGACTATCTATCCGTGGTCCTGAACCAGTTATGTGTGTTGCATGAGAAAACGCCAGTAAGTGACAGAGTC
ACCAAATGCTGCACAGAATCCTTGGTGAACAGGCGACCATGCTTTTCAGCTCTGGAAGTCGATGAAACATA
CGTTCCCAAAGAGTTTAATGCTGAAACATTCACCTTCCATGCAGATATATGCACACTTTCTGAGAAGGAGA
GACAAATCAAGAAACAAACTGCACTTGTTGAGCTTGTGAAACACAAGCCCAAGGCAACAAAAGAGCAACTG
AAAGCTGTTATGGATGATTTCGCAGCTTTTGTAGAGAAGTGCTGCAAGGCTGACGATAAGGAGACCTGCTT
TGCCGAGGAGGGTAAAAAACTTGTTGCTGCAAGTCAAGCTGCCTTAGGCTTAATCTGTGACAGCCGAGTCC
TGGAGAGGTACCTCTTGGAGGCCAAGGAGGCCGAGAATATCACGACGGGCTGTGCTGAACACTGCAGCTTG
AATGAGAATATCACTGTCCCAGACACCAAAGTTAATTTCTATGCCTGGAAGAGGATGGAGGTCGGGCAGCA
GGCCGTAGAAGTCTGGCAGGGCCTGGCCCTGCTGTCGGAAGCTGTCCTGCGGGGCCAGGCCCTGTTGGTCA
ACTCTTCCCAGCCGTGGGAGCCCCTGCAGCTGCATGTGGATAAAGCCGTCAGTGGCCTTCGCAGCCTCACC
ACTCTGCTTCGGGCTCTGCGAGCCCAGAAGGAAGCCATCTCCCCTCCAGATGCGGCCTCAGCTGCTCCACT
CCGAACAATCACTGCTGACACTTTCCGCAAACTCTTCCGAGTCTACTCCAATTTCCTCCGGGGAAAGCTGA
AGCTGTACACAGGGGAGGCCTGCAGGACAGGGGACAGATGA
```

(F) Seq ID No. 6. Amino Acid Sequence of Human HSA-hEPO Fusion Protein

```
DAHKSEVAHRFKDLGEENFKALVLIAFAQYLQQCPFEDHVKLVNEVTEFAKTCVADESAENCDKSLHTLFG
DKLCTVATLRETYGEMADCCAKQEPERNECFLQHKDDNPNLPRLVRPEVDVMCTAFHDNEETFLKKYLYEI
ARRHPYFYAPELLFFAKRYKAAFTECCQAADKAACLLPKLDELRDEGKASSAKQRLKCASLQKFGERAFKA
WAVARLSQRFPKAEFAEVSKLVTDLTKVHTECCHGDLLECADDRADLAKYICENQDSISSKLKECCEKPLL
EKSHCIAEVENDEMPADLPSLAADFVESKDVCKNYAEAKDVFLGMFLYEYARRHPDYSVVLLLRLAKTYET
TLEKCCAAADPHECYAKVFDEFKPLVEEPQNLIKQNCELFEQLGEYKFQNALLVRYTKKVPEVSTPTLVEV
SRNLGKVGSKCCKHPEAKRMPCAEDYLSVVLNQLCVLHEKTPVSDRVTKCCTESLVNRRPCFSALEVDETY
VPKEFNAETFTFHADICTLSEKERQIKKQTALVELVKHKPKATKEQLKAVMDDFAAFVEKCCKADDKETCF
AEEGKKLVAASQAALGLICDSRVLERYLLEAKEAENITTGCAEHCSLNENITVPDTKVNFYAWKRMEVGQQ
AVEVWQGLALLSEAVLRGQALLVNSSQPWEPLQLHVDKAVSGLRSLTTLLRALRAQKEAISPPDAASAAPL
RTITADTFRKLFRVYSNFLRGKLKLYTGEACRTGDR
```

Figure 1-continued

(G) Seq ID No. 7. DNA Sequence Encoding HSA-hGCSF

ATGAAGTGGGTAACCTTTATTTCCCTTCTTTTTCTCTTTAGCTCGGCTTATTCCAGGGGTGTGTTTCGTCG
AGATGCACACAAGAGTGAGGTTGCTCATCGGTTTAAAGATTTGGGAGAAGAAAATTTCAAAGCCTTGGTGT
TGATTGCCTTTGCTCAGTATCTTCAGCAGTGTCCATTTGAAGATCATGTAAAATTAGTGAATGAAGTAACT
GAATTTGCAAAAACATGTGTTGCTGATGAGTCAGCTGAAAATTGTGACAAATCACTTCATACCCTTTTTGG
AGACAAATTATGCACAGTTGCAACTCTTCGTGAAACCTATGGTGAAATGGCTGACTGCTGTGCAAAACAAG
AACCTGAGAGAAATGAATGCTTCTTGCAACACAAAGATGACAACCCAAACCTCCCCCGATTGGTGAGACCA
GAGGTTGATGTGATGTGCACTGCTTTTCATGACAATGAAGAGACATTTTTGAAAAAATACTTATATGAAAT
TGCCAGAAGACATCCTTACTTTTATGCCCCGGAACTCCTTTTCTTTGCTAAAAGGTATAAAGCTGCTTTTA
CAGAATGTTGCCAAGCTGCTGATAAAGCTGCCTGCCTGTTGCCAAAGCTCGATGAACTTCGGGATGAAGGG
AAGGCTTCGTCTGCCAAACAGAGACTCAAGTGTGCCAGTCTCCAAAAATTTGGAGAAAGAGCTTTCAAAGC
ATGGGCAGTAGCTCGCCTGAGCCAGAGATTTCCCAAAGCTGAGTTTGCAGAAGTTTCCAAGTTAGTGACAG
ATCTTACCAAAGTCCACACGGAATGCTGCCATGGAGATCTGCTTGAATGTGCTGATGACAGGGCGGACCTT
GCCAAGTATATCTGTGAAAATCAAGATTCGATCTCCAGTAAACTGAAGGAATGCTGTGAAAAACCTCTGTT
GGAAAAATCCCACTGCATTGCCGAAGTGGAAAATGATGAGATGCCTGCTGACTTGCCTTCATTAGCTGCTG
ATTTTGTTGAAAGTAAGGATGTTTGCAAAAACTATGCTGAGGCAAAGGATGTCTTCCTGGGCATGTTTTTG
TATGAATATGCAAGAAGGCATCCTGATTACTCTGTCGTGCTGCTGCTGAGACTTGCCAAGACATATGAAAC
CACTCTAGAGAAGTGCTGTGCCGCTGCAGATCCTCATGAATGCTATGCCAAAGTGTTCGATGAATTTAAAC
CTCTTGTGGAAGAGCCTCAGAATTTAATCAAACAAAATTGTGAGCTTTTTGAGCAGCTTGGAGAGTACAAA
TTCCAGAATGCGCTATTAGTTCGTTACACCAAGAAAGTACCCCAAGTGTCAACTCCAACTCTTGTAGAGGT
CTCAAGAAACCTAGGAAAAGTGGGCAGCAAATGTTGTAAACATCCTGAAGCAAAAAGAATGCCCTGTGCAG
AAGACTATCTATCCGTGGTCCTGAACCAGTTATGTGTGTTGCATGAGAAAACGCCAGTAAGTGACAGAGTC
ACCAAATGCTGCACAGAATCCTTGGTGAACAGGCGACCATGCTTTTCAGCTCTGGAAGTCGATGAAACATA
CGTTCCCAAAGAGTTTAATGCTGAAACATTCACCTTCCATGCAGATATATGCACACTTTCTGAGAAGGAGA
GACAAATCAAGAAACAAACTGCACTTGTTGAGCTTGTGAAACACAAGCCCAAGGCAACAAAAGAGCAACTG
AAAGCTGTTATGGATGATTTCGCAGCTTTTGTAGAGAAGTGCTGCAAGGCTGACGATAAGGAGACCTGCTT
TGCCGAGGAGGGTAAAAAACTTGTTGCTGCAAGTCAAGCTGCCTTAGGCTTA<u>ACCCCCCTGGGCCCTGCCA
GCTCCCTGCCCCAGAGCTTCCTGCTCAAGTGCTTAGAGCAAGTGAGGAAGATCCAGGGCGATGGCGCAGCG
CTCCAGGAGAAGCTGTGTGCCACCTACAAGCTGTGCCACCCCGAGGAGCTGGTGCTGCTCGGACACTCTCT
GGGCATCCCCTGGGCTCCCCTGAGCAGCTGCCCCAGCCAGGCCCTGCAGCTGGCAGGCTGCTTGAGCCAAC
TCCATAGCGGCCTTTTCCTCTACCAGGGGCTCCTGCAGGCCCTGGAAGGGATCTCCCCCGAGTTGGGTCCC
ACCTTGGACACACTGCAGCTGGACGTCGCCGACTTTGCCACCACCATCTGGCAGCAGATGGAAGAACTGGG
AATGGCCCCTGCCCTGCAGCCCACCCAGGGTGCCATGCCGGCCTTCGCCTCTGCTTTCCAGCGCCGGGCAG
GAGGGGTCCTAGTTGCCTCCCATCTGCAGAGCTTCCTGGAGGTGTCGTACCGCGTTCTACGCCACCTTGCC
CAGCCCTGA</u>

(H) Seq ID No. 8. Amino Acid Sequence of HSA-hGCSF Fusion Protein

DAHKSEVAHRFKDLGEENFKALVLIAFAQYLQQCPFEDHVKLVNEVTEFAKTCVADESAENCDKSLHTLFG
DKLCTVATLRETYGEMADCCAKQEPERNECFLQHKDDNPNLPRLVRPEVDVMCTAFHDNEETFLKKYLYEI
ARRHPYFYAPELLFFAKRYKAAFTECCQAADKAACLLPKLDELRDEGKASSAKQRLKCASLQKFGERAFKA
WAVARLSQRFPKAEFAEVSKLVTDLTKVHTECCHGDLLECADDRADLAKYICENQDSISSKLKECCEKPLL
EKSHCIAEVENDEMPADLPSLAADFVESKDVCKNYAEAKDVFLGMFLYEYARRHPDYSVVLLLRLAKTYET
TLEKCCAAADPHECYAKVFDEFKPLVEEPQNLIKQNCELFEQLGEYKFQNALLVRYTKKVPEVSTPTLVEV
SRNLGKVGSKCCKHPEAKRMPCAEDYLSVVLNQLCVLHEKTPVSDRVTKCCTESLVNRRPCFSALEVDETY
VPKEFNAETFTFHADICTLSEKERQIKKQTALVELVKHKPKATKEQLKAVMDDFAAFVEKCCKADDKETCF
AEEGKKLVAASQAALGLTPLGPASSLPQSFLLKCLEQVRKIQGDGAALQEKLCATYKLCHPEELVLLGHSL
GIPWAPLSSCPSQALQLAGCLSQLHSGLFLYQGLLQALEGISPELGPTLDTLQLDVADFATTIWQQMEELG
MAPALQPTQGAMPAFASAFQRRAGGVLVASHLQSFLEVSYRVLRHLAQP

Figure 1-continued

(I) Seq ID No. 9. DNA Sequence Encoding HSA-hGMCSF

ATGAAGTGGGTAACCTTTATTTCCCTTCTTTTTCTCTTTAGCTCGGCTTATTCCAGGGGTGTGTTTCGTCG
AGATGCACACAAGAGTGAGGTTGCTCATCGGTTTAAAGATTTGGGAGAAGAAAATTTCAAAGCCTTGGTGT
TGATTGCCTTTGCTCAGTATCTTCAGCAGTGTCCATTTGAAGATCATGTAAAATTAGTGAATGAAGTAACT
GAATTTGCAAAAACATGTGTTGCTGATGAGTCAGCTGAAAATTGTGACAAATCACTTCATACCCTTTTTGG
AGACAAATTATGCACAGTTGCAACTCTTCGTGAAACCTATGGTGAAATGGCTGACTGCTGTGCAAAACAAG
AACCTGAGAGAAATGAATGCTTCTTGCAACACAAAGATGACAACCCAAACCTCCCCCGATTGGTGAGACCA
GAGGTTGATGTGATGTGCACTGCTTTTCATGACAATGAAGAGACATTTTTGAAAAAATACTTATATGAAAT
TGCCAGAAGACATCCTTACTTTTATGCCCCGGAACTCCTTTTCTTTGCTAAAAGGTATAAAGCTGCTTTTA
CAGAATGTTGCCAAGCTGCTGATAAAGCTGCCTGCCTGTTGCCAAAGCTCGATGAACTTCGGGATGAAGGG
AAGGCTTCGTCTGCCAAACAGAGACTCAAGTGTGCCAGTCTCCAAAAATTTGGAGAAAGAGCTTTCAAAGC
ATGGGCAGTAGCTCGCCTGAGCCAGAGATTTCCCAAAGCTGAGTTTGCAGAAGTTTCCAAGTTAGTGACAG
ATCTTACCAAAGTCCACACGGAATGCTGCCATGGAGATCTGCTTGAATGTGCTGATGACAGGGCGGACCTT
GCCAAGTATATCTGTGAAAATCAAGATTCGATCTCCAGTAAACTGAAGGAATGCTGTGAAAAACCTCTGTT
GGAAAAATCCCACTGCATTGCCGAAGTGGAAAATGATGAGATGCCTGCTGACTTGCCTTCATTAGCTGCTG
ATTTTGTTGAAAGTAAGGATGTTTGCAAAAACTATGCTGAGGCAAAGGATGTCTTCCTGGGCATGTTTTTG
TATGAATATGCAAGAAGGCATCCTGATTACTCTGTCGTGCTGCTGCTGAGACTTGCCAAGACATATGAAAC
CACTCTAGAGAAGTGCTGTGCCGCTGCAGATCCTCATGAATGCTATGCCAAAGTGTTCGATGAATTTAAAC
CTCTTGTGGAAGAGCCTCAGAATTTAATCAAACAAAATTGTGAGCTTTTTGAGCAGCTTGGAGAGTACAAA
TTCCAGAATGCGCTATTAGTTCGTTACACCAAGAAAGTACCCCAAGTGTCAACTCCAACTCTTGTAGAGGT
CTCAAGAAACCTAGGAAAAGTGGGCAGCAAATGTTGTAAACATCCTGAAGCAAAAAGAATGCCCTGTGCAG
AAGACTATCTATCCGTGGTCCTGAACCAGTTATGTGTGTTGCATGAGAAAACGCCAGTAAGTGACAGAGTC
ACCAAATGCTGCACAGAATCCTTGGTGAACAGGCGACCATGCTTTTCAGCTCTGGAAGTCGATGAAACATA
CGTTCCCAAAGAGTTTAATGCTGAAACATTCACCTTCCATGCAGATATATGCACACTTTCTGAGAAGGAGA
GACAAATCAAGAAACAAACTGCACTTGTTGAGCTTGTGAAACACAAGCCCAAGGCAACAAAAGAGCAACTG
AAAGCTGTTATGGATGATTTCGCAGCTTTTGTAGAGAAGTGCTGCAAGGCTGACGATAAGGAGACCTGCTT
TGCCGAGGAGGGTAAAAAACTTGTTGCTGCAAGTCAAGCTGCCTTAGGCTTAGCACCCGCCCGCTCGCCCA
GCCCCAGCACGCAGCCCTGGGAGCATGTGAATGCCATCCAGGAGGCCCGGCGTCTCCTGAACCTGAGTAGA
GACACTGCTGCTGAGATGAATGAAACAGTAGAAGTCATCTCAGAAATGTTTGACCTCCAGGAGCCGACCTG
CCTACAGACCCGCCTGGAGCTGTACAAGCAGGGCCTGCGGGGCAGCCTCACCAAGCTCAAGGGCCCCTTGA
CCATGATGGCCAGCCACTACAAGCAGCACTGCCCTCCAACCCCGGAAACTTCCTGTGCAACCCAGATTATC
ACCTTTGAAAGTTTCAAAGAGAACCTGAAGGACTTTCTGCTTGTCATCCCCTTTGACTGCTGGGAGCCAGT
CCAGGAGTGA (J) Seq ID No. 10. Amino Acid Sequence of Human HSA-hGMCSF Fusion Protein DAHKSEVAHRFKDLGEENFKALVLIAFAQYLQQCPFEDHVKLVNEVTEFAKTCVADESAENCDKSLHTLFG
DKLCTVATLRETYGEMADCCAKQEPERNECFLQHKDDNPNLPRLVRPEVDVMCTAFHDNEETFLKKYLYEI
ARRHPYFYAPELLFFAKRYKAAFTECCQAADKAACLLPKLDELRDEGKASSAKQRLKCASLQKFGERAFKA
WAVARLSQRFPKAEFAEVSKLVTDLTKVHTECCHGDLLECADDRADLAKYICENQDSISSKLKECCEKPLL
EKSHCIAEVENDEMPADLPSLAADFVESKDVCKNYAEAKDVFLGMFLYEYARRHPDYSVVLLLRLAKTYET
TLEKCCAAADPHECYAKVFDEFKPLVEEPQNLIKQNCELFEQLGEYKFQNALLVRYTKKVPEVSTPTLVEV
SRNLGKVGSKCCKHPEAKRMPCAEDYLSVVLNQLCVLHEKTPVSDRVTKCCTESLVNRRPCFSALEVDETY
VPKEFNAETFTFHADICTLSEKERQIKKQTALVELVKHKPKATKEQLKAVMDDFAAFVEKCCKADDKETCF
AEEGKKLVAASQAALGLAPARSPSPSTQPWEHVNAIQEARRLLNLSRDTAAEMNETVEVISEMFDLQEPTC
LQTRLELYKQGLRGSLTKLKGPLTMMASHYKQHCPPTPETSCATQIITFESFKENLKDFLLVIPFDCWEPV
QE

Figure 1-continued

(K) Seq ID No. 11. DNA Sequence Encoding Human Serum Albumin (HSA)

ATGAAGTGGGTAACCTTTATTTCCCTTCTTTTTCTCTTTAGCTCGGCTTATTCCAGGGGTGTGTTTCGTCG
AGATGCACACAAGAGTGAGGTTGCTCATCGGTTTAAAGATTTGGGAGAAGAAAATTTCAAAGCCTTGGTGT
TGATTGCCTTTGCTCAGTATCTTCAGCAGTGTCCATTTGAAGATCATGTAAAATTAGTGAATGAAGTAACT
GAATTTGCAAAAACATGTGTTGCTGATGAGTCAGCTGAAAATTGTGACAAATCACTTCATACCCTTTTTGG
AGACAAATTATGCACAGTTGCAACTCTTCGTGAAACCTATGGTGAAATGGCTGACTGCTGTGCAAAACAAG
AACCTGAGAGAAATGAATGCTTCTTGCAACACAAAGATGACAACCCAAACCTCCCCCGATTGGTGAGACCA
GAGGTTGATGTGATGTGCACTGCTTTTCATGACAATGAAGAGACATTTTTGAAAAAATACTTATATGAAAT
TGCCAGAAGACATCCTTACTTTTATGCCCCGGAACTCCTTTTCTTTGCTAAAAGGTATAAAGCTGCTTTTA
CAGAATGTTGCCAAGCTGCTGATAAAGCTGCCTGCCTGTTGCCAAAGCTCGATGAACTTCGGGATGAAGGG
AAGGCTTCGTCTGCCAAACAGAGACTCAAGTGTGCCAGTCTCCAAAAATTTGGAGAAAGAGCTTTCAAAGC
ATGGGCAGTAGCTCGCCTGAGCCAGAGATTTCCCAAAGCTGAGTTTGCAGAAGTTTCCAAGTTAGTGACAG
ATCTTACCAAAGTCCACACGGAATGCTGCCATGGAGATCTGCTTGAATGTGCTGATGACAGGGCGGACCTT
GCCAAGTATATCTGTGAAAATCAAGATTCGATCTCCAGTAAACTGAAGGAATGCTGTGAAAAACCTCTGTT
GGAAAAATCCCACTGCATTGCCGAAGTGGAAAATGATGAGATGCCTGCTGACTTGCCTTCATTAGCTGCTG
ATTTTGTTGAAAGTAAGGATGTTTGCAAAAACTATGCTGAGGCAAAGGATGTCTTCCTGGGCATGTTTTTG
TATGAATATGCAAGAAGGCATCCTGATTACTCTGTCGTGCTGCTGCTGAGACTTGCCAAGACATATGAAAC
CACTCTAGAGAAGTGCTGTGCCGCTGCAGATCCTCATGAATGCTATGCCAAAGTGTTCGATGAATTTAAAC
CTCTTGTGGAAGAGCCTCAGAATTTAATCAAACAAAATTGTGAGCTTTTTGAGCAGCTTGGAGAGTACAAA
TTCCAGAATGCGCTATTAGTTCGTTACACCAAGAAAGTACCCCAAGTGTCAACTCCAACTCTTGTAGAGGT
CTCAAGAAACCTAGGAAAAGTGGGCAGCAAATGTTGTAAACATCCTGAAGCAAAAAGAATGCCCTGTGCAG
AAGACTATCTATCCGTGGTCCTGAACCAGTTATGTGTGTTGCATGAGAAAACGCCAGTAAGTGACAGAGTC
ACCAAATGCTGCACAGAATCCTTGGTGAACAGGCGACCATGCTTTTCAGCTCTGGAAGTCGATGAAACATA
CGTTCCCAAAGAGTTTAATGCTGAAACATTCACCTTCCATGCAGATATATGCACACTTTCTGAGAAGGAGA
GACAAATCAAGAAACAAACTGCACTTGTTGAGCTTGTGAAACACAAGCCCAAGGCAACAAAAGAGCAACTG
AAAGCTGTTATGGATGATTTCGCAGCTTTTGTAGAGAAGTGCTGCAAGGCTGACGATAAGGAGACCTGCTT
TGCCGAGGAGGGTAAAAAACTTGTTGCTGCAAGTCAAGCTGCCTTAGGCTTATAA (L) Seq ID No. 12. Amino Acid Sequence of Human Serum Albumin (HSA)

MKWVTFISLLFLFSSAYSRGVFRRDAHKSEVAHRFKDLGEENFKALVLIAFAQYLQQCPFEDHVKLVNEVT
EFAKTCVADESAENCDKSLHTLFGDKLCTVATLRETYGEMADCCAKQEPERNECFLQHKDDNPNLPRLVRP
EVDVMCTAFHDNEETFLKKYLYEIARRHPYFYAPELLFFAKRYKAAFTECCQAADKAACLLPKLDELRDEG
KASSAKQRLKCASLQKFGERAFKAWAVARLSQRFPKAEFAEVSKLVTDLTKVHTECCHGDLLECADDRADL
AKYICENQDSISSKLKECCEKPLLEKSHCIAEVENDEMPADLPSLAADFVESKDVCKNYAEAKDVFLGMFL
YEYARRHPDYSVVLLLRLAKTYETTLEKCCAAADPHECYAKVFDEFKPLVEEPQNLIKQNCELFEQLGEYK
FQNALLVRYTKKVPEVSTPTLVEVSRNLGKVGSKCCKHPEAKRMPCAEDYLSVVLNQLCVLHEKTPVSDRV
TKCCTESLVNRRPCFSALEVDETYVPKEFNAETFTFHADICTLSEKERQIKKQTALVELVKHKPKATKEQL
KAVMDDFAAFVEKCCKADDKETCFAEEGKKLVAASQAALGL

Figure 1-continued

(O) Seq ID No. 15. DNA Sequence Encoding Human Erythropoietin (EPO)

ATGGGGGTGCACGAATGTCCTGCCTGGCTGTGGCTTCTCCTGTCCCTGCTGTCGCTCCC
TCTGGGCCTCCCAGTCCTGGGCGCCCCACCACGCCTCATCTGTGACAGCCGAGTCCTGG
AGAGGTACCTCTTGGAGGCCAAGGAGGCCGAGAATATCACGACGGGCTGTGCTGAACAC
TGCAGCTTGAATGAGAATATCACTGTCCCAGACACCAAAGTTAATTTCTATGCCTGGAA
GAGGATGGAGGTCGGGCAGCAGGCCGTAGAAGTCTGGCAGGGCCTGGCCCTGCTGTCGG
AAGCTGTCCTGCGGGCCAGGCCCTGTTGGTCAACTCTTCCCAGCCGTGGGAGCCCCTG
CAGCTGCATGTGGATAAAGCCGTCAGTGGCCTTCGCAGCCTCACCACTCTGCTTCGGGC
TCTGCGAGCCCAGAAGGAAGCCATCTCCCCTCCAGATGCGGCCTCAGCTGCTCCACTCC
GAACAATCACTGCTGACACTTTCCGCAAACTCTTCCGAGTCTACTCCAATTTCCTCCGG
GGAAAGCTGAAGCTGTACACAGGGGAGGCCTGCAGGACAGGGGACAGATGA (P) Seq ID No. 16. Amino Acid Sequence of Human Erythropoietin (EPO)

MGVHECPAWLWLLLSLLSLPLGLPVLGAPPRLICDSRVLERYLLEAKEAENITTGCAEH
CSLNENITVPDTKVNFYAWKRMEVGQQAVEVWQGLALLSEAVLRGQALLVNSSQPWEPL
QLHVDKAVSGLRSLTTLLRALRAQKEAISPPDAASAAPLRTITADTFRKLFRVYSNFLR
GKLKLYTGEACRTGDR

Figure 1-continued

(Q) Seq ID No. 17. DNA Sequence Encoding Human GCSF

GGATCCATGGCTGGACCTGCCACCCAGAGCCCCATGAAGCTGATGGCCCTGCAGCTGCT
GCTGTGGCACAGTGCACTCTGGACAGTGCAGGAAGCCACCCCCCTGGGCCCTGCCAGCT
CCCTGCCCCAGAGCTTCCTGCTCAAGTGCTTAGAGCAAGTGAGGAAGATCCAGGGCGAT
GGCGCAGCGCTCCAGGAGAAGCTGTGTGCCACCTACAAGCTGTGCCACCCCGAGGAGCT
GGTGCTGCTCGGACACTCTCTGGGCATCCCCTGGGCTCCCCTGAGCAGCTGCCCCAGCC
AGGCCCTGCAGCTGGCAGGCTGCTTGAGCCAACTCCATAGCGGCCTTTTCCTCTACCAG
GGGCTCCTGCAGGCCCTGGAAGGGATCTCCCCCGAGTTGGGTCCCACCTTGGACACACT
GCAGCTGGACGTCGCCGACTTTGCCACCACCATCTGGCAGCAGATGGAAGAACTGGGAA
TGGCCCCTGCCCTGCAGCCCACCCAGGGTGCCATGCCGGCCTTCGCCTCTGCTTTCCAG
CGCCGGGCAGGAGGGGTCCTAGTTGCCTCCCATCTGCAGAGCTTCCTGGAGGTGTCGTA
CCGCGTTCTACGCCACCTTGCCCAGCCCTGAGCCGAATTC (R) Seq ID No. 18. Amino Acid Sequence of Human GCSF MAGPATQSPMKLMALQLLLWHSALWTVQEAT<u>PLGPASSLPQSFLLKCLEQVRKIQGDGA
ALQEKLCATYKLCHPEELVLLGHSLGIPWAPLSSCPSQALQLAGCLSQLHSGLFLYQGL
LQALEGISPELGPTLDTLQLDVADFATTIWQQMEELGMAPALQPTQGAMPAFASAFQRR
AGGVLVASHLQSFLEVSYRVLRHLAQP</u>

Figure 1-continued

(M) Seq ID No. 13. DNA Sequence Encoding Human Interleukin-11 (IL-11)

ATGAACTGTGTTTGCCGCCTGGTCCTGGTCGTGCTGAGCCTGTGGCCAGATACAGCTGT
CGCCCCTGGGCCACCACCTGGCCCCCCTCGAGTTTCCCCAGACCCTCGGGCCGAGCTGG
ACAGCACCGTGCTCCTGACCCGCTCTCTCCTGGCGGACACGCGGCAGCTGGCTGCACAG
CTGAGGGACAAATTCCCAGCTGACGGGGACCACAACCTGGATTCCCTGCCCACCCTGGC
CATGAGTGCGGGGGCACTGGGAGCTCTACAGCTCCCAGGTGTGCTGACAAGGCTGCGAG
CGGACCTACTGTCCTACCTGCGGCACGTGCAGTGGCTGCGCCGGGCAGGTGGCTCTTCC
CTGAAGACCCTGGAGCCCGAGCTGGGCACCCTGCAGGCCCGACTGGACCGGCTGCTGCG
CCGGCTGCAGCTCCTGATGTCCCGCCTGGCCCTGCCCCAGCCACCCCGGACCCGCCGG
CGCCCCCGCTGGCGCCCCCCTCCTCAGCCTGGGGGGGCATCAGGGCCGCCCACGCCATC
CTGGGGGGGCTGCACCTGACACTTGACTGGGCCGTGAGGGGACTGCTGCTGCTGAAGAC
TCGGCTGTGA (N) Seq ID No. 14. Amino Acid Sequence of Human Interleukin-11 (IL-11)

MNCVCRLVLVVLSLWPDTAVAPGPPPGPPRVSPDPRAELDSTVLLTRSLLADTRQLAAQ
LRDKFPADGDHNLDSLPTLAMSAGALGALQLPGVLTRLRADLLSYLRHVQWLRRAGGSS
LKTLEPELGTLQARLDRLLRRLQLLMSRLALPQPPPDPPAPPLAPPSSAWGGIRAAHAI
LGGLHLTLDWAVRGLLLLKTRL

Figure 1-continued

(S) Seq ID No. 19. DNA Sequence Encoding Human GMCSF

ATGTGGCTGCAGAGCCTGCTGCTCTTGGGCACTGTGGCCTGCAGCATCTCTGCACCCGC
CCGCTCGCCCAGCCCCAGCACGCAGCCCTGGGAGCATGTGAATGCCATCCAGGAGGCCC
GGCGTCTCCTGAACCTGAGTAGAGACACTGCTGCTGAGATGAATGAAACAGTAGAAGTC
ATCTCAGAAATGTTTGACCTCCAGGAGCCGACCTGCCTACAGACCCGCCTGGAGCTGTA
CAAGCAGGGCCTGCGGGGCAGCCTCACCAAGCTCAAGGGCCCCTTGACCATGATGGCCA
GCCACTACAAGCAGCACTGCCCTCCAACCCCGGAAACTTCCTGTGCAACCCAGATTATC
ACCTTTGAAAGTTTCAAAGAGAACCTGAAGGACTTTCTGCTTGTCATCCCCTTTGACTG
CTGGGAGCCAGTCCAGGAGTGAGACCGGCCAGATG (T) Seq ID No. 20. Amino Acid Sequence of Human GMCSF MWLQSLLLLGTVACSISAPARSPSPSTQPWEHVNAIQEARRLLNLSRDTAAEMNETVEV
ISEMFDLQEPTCLQTRLELYKQGLRGSLTKLKGPLTMMASHYKQHCPPTPETSCATQII
TFESFKENLKDFLLVIPFDCWEPVQE

Figure 1-continued

(U) Seq ID No. 21. DNA Sequence Encoding Human IL-3

ATGAGCCGCCTGCCCGTCCTGCTCCTGCTCCAACTCCTGGTCCGCCCCGGACTCCAAGC
TCCCATGACCCAGACAACGTCCTTGAAGACAAGCTGGGTTAACTGCTCTAACATGATCG
ATGAAATTATAACACACTTAAAGCAGCCACCTTTGCCTTTGCTGGACTTCAACAACCTC
AATGGGGAAGACCAAGACATTCTGATGGAAAATAACCTTCGAAGGCCAAACCTGGAGGC
ATTCAACAGGGCTGTCAAGAGTTTACAGAACGCATCAGCAATTGAGAGCATTCTTAAAA
ATCTCCTGCCATGTCTGCCCCTGGCCACGGCCGCACCCACGCGACATCCAATCCATATC
AAGGACGGTGACTGGAATGAATTCCGGAGGAAACTGACGTTCTATCTGAAAACCCTTGA
GAATGCGCAGGCTCAACAGACGACTTTGAGCCTCGCGATCTTTTAG (V) Seq ID No. 22. Amino Acid Sequence of Human IL-3

MSRLPVLLLLQLLVRPGLQAPMTQTTSLKTSWVNCSNMIDEIITHLKQPPLPLLDFNNL
NGEDQDILMENNLRRPNLEAFNRAVKSLQNASAIESILKNLLPCLPLATAAPTRHPIHI
KDGDWNEFRRKLTFYLKTLENAQAQQTTLSLAIF

Figure 6.
A.
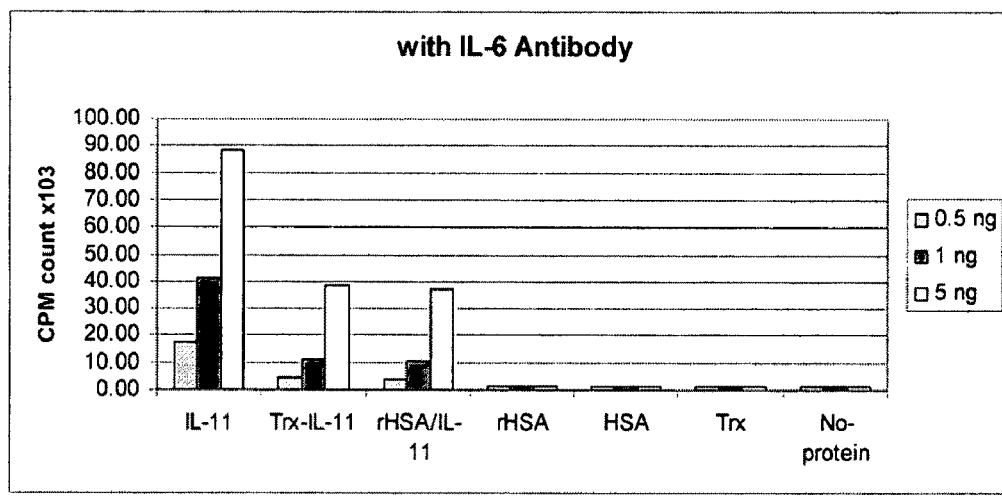
B.
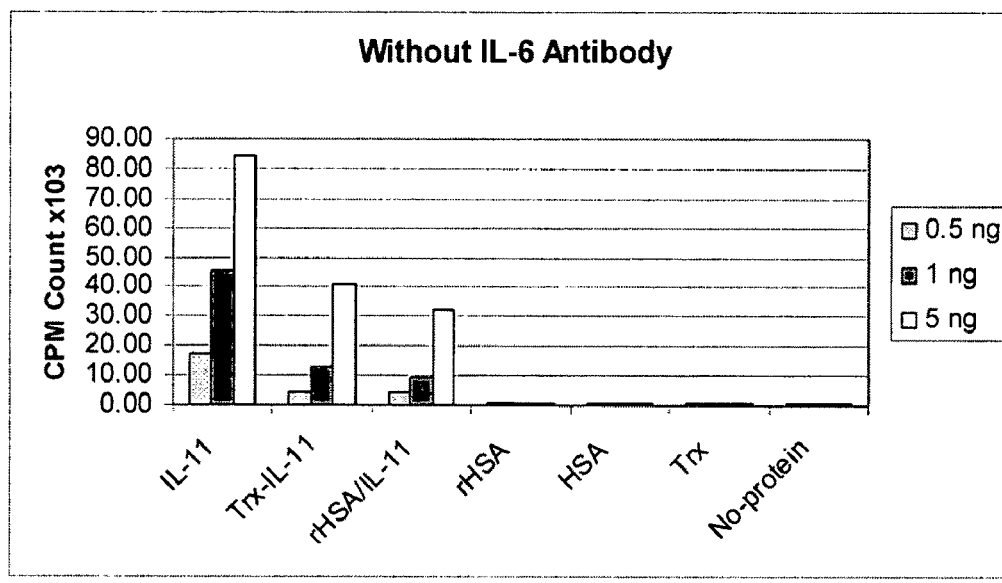

Figure 8.
A.
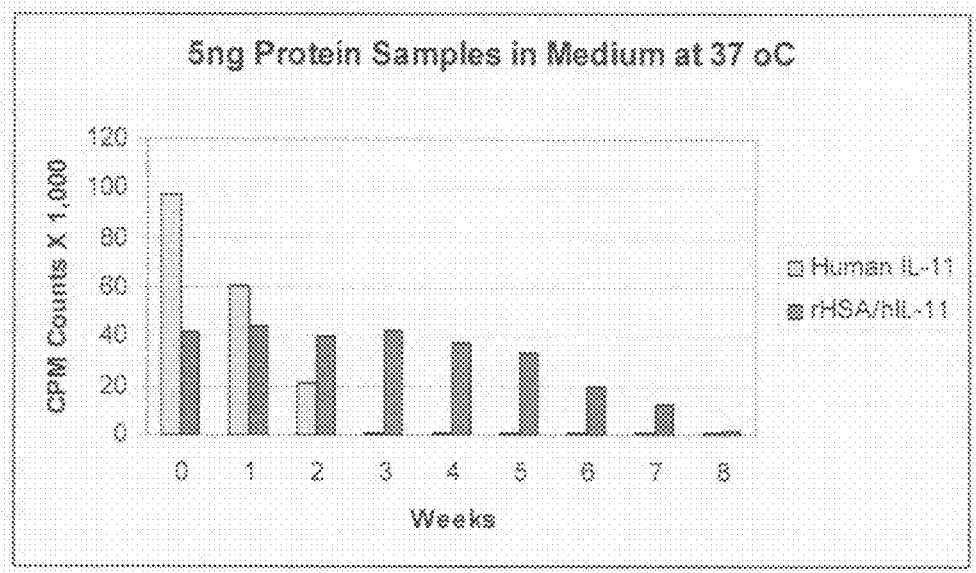
B.
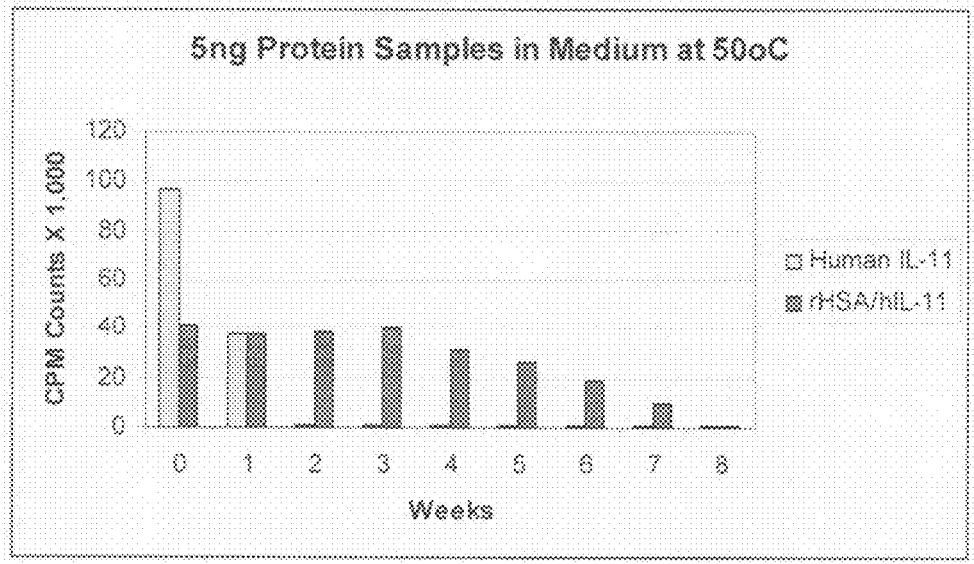

Figure 9.
A.
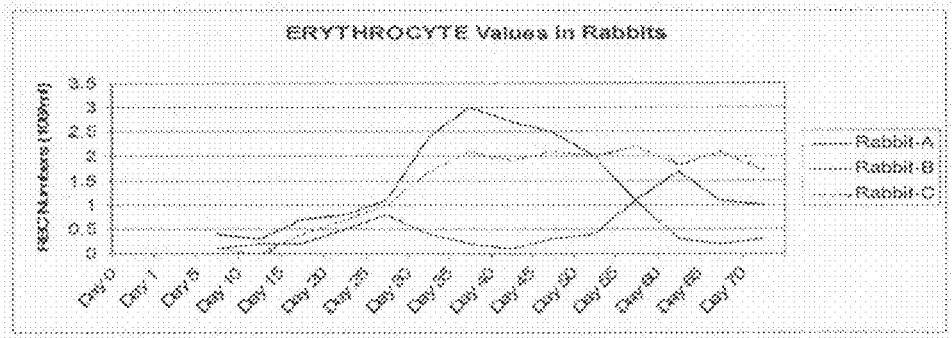
B.
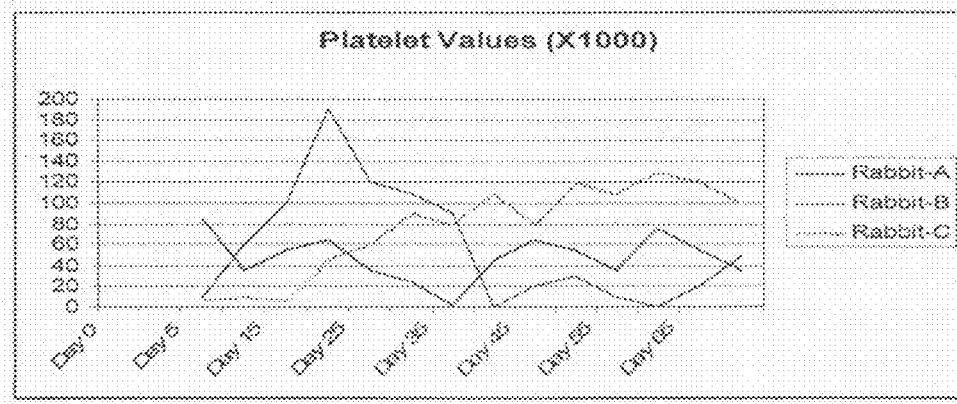
C.
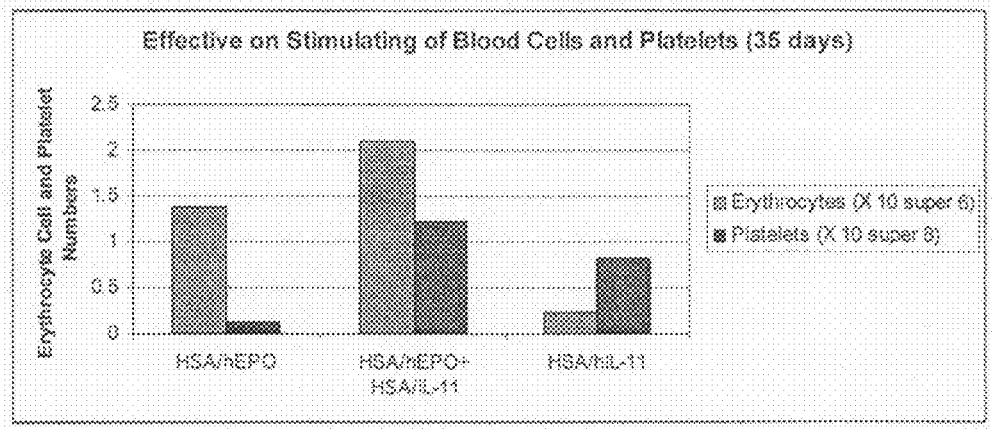

SEQUENCE LISTING

<160> NUMBER OF SEQ ID NOS: 40

<210> SEQ ID NO 1
<211> LENGTH: 2229
<212> TYPE: DNA
<213> ORGANISM: Artificial Sequence
<220> FEATURE:
<223> OTHER INFORMATION: DNA of HSA-hIL-11

<400> SEQUENCE: 1

```
atgaagtggg taacctttat ttcccttctt tttctcttta gctcggctta ttccaggggt      60
gtgtttcgtc gagatgcaca caagagtgag gttgctcatc ggtttaaaga tttgggagaa     120
gaaaatttca aagccttggt gttgattgcc tttgctcagt atcttcagca gtgtccattt     180
gaagatcatg taaaattagt gaatgaagta actgaatttg caaaaacatg tgttgctgat     240
gagtcagctg aaaattgtga caaatcactt catacccttt ttggagacaa attatgcaca     300
gttgcaactc ttcgtgaaac ctatggtgaa atggctgact gctgtgcaaa acaagaacct     360
gagagaaatg aatgcttctt gcaacacaaa gatgacaacc caaacctccc ccgattggtg     420
agaccagagg ttgatgtgat gtgcactgct tttcatgaca atgaagagac attttttgaaa     480 aaatacttat atgaaattgc agaagacatc cttactttt atgcccgga actccttttc     540 tttgctaaaa ggtataaagc tgcttttaca gaatgttgcc aagctgctga taaagctgcc     600
tgcctgttgc caaagctcga tgaacttcgg gatgaaggga aggcttcgtc tgccaaacag     660
agactcaagt gtgccagtct ccaaaaattt ggagaaagag ctttcaaagc atgggcagta     720
gctcgcctga gccagagatt tcccaaagct gagtttgcag aagtttccaa gttagtgaca     780
gatcttacca agtccacac ggaatgctgc catggagatc tgcttgaatg tgctgatgac     840
agggcggacc ttgccaagta tatctgtgaa aatcaagatt cgatctccag taaactgaag     900
gaatgctgtg aaaaacctct gttggaaaaa tcccactgca ttgccgaagt ggaaaatgat     960
gagatgcctg ctgacttgcc ttcattagct gctgattttg ttgaaagtaa ggatgtttgc    1020
aaaaactatg ctgaggcaaa ggatgtcttc ctgggcatgt ttttgtatga atatgcaaga    1080
aggcatcctg attactctgt cgtgctgctg ctgagacttg ccaagacata tgaaaccact    1140
ctagagaagt gctgtgccgc tgcagatcct catgaatgct atgccaaagt gttcgatgaa    1200
tttaaacctc ttgtggaaga gcctcagaat ttaatcaaac aaaattgtga gcttttgag    1260 cagcttggag agtacaaatt ccagaatgcg ctattagttc gttacaccaa gaaagtaccc    1320
caagtgtcaa ctccaactct tgtagaggtc tcaagaaacc taggaaaagt gggcagcaaa    1380
```

```
tgttgtaaac atcctgaagc aaaaagaatg ccctgtgcag aagactatct atccgtggtc    1440
ctgaaccagt tatgtgtgtt gcatgagaaa acgccagtaa gtgacagagt caccaaatgc    1500
tgcacagaat ccttggtgaa caggcgacca tgcttttcag ctctggaagt cgatgaaaca    1560
tacgttccca aagagtttaa tgctgaaaca ttcaccttcc atgcagatat atgcacactt    1620
tctgagaagg agagacaaat caagaaacaa actgcacttg ttgagcttgt gaaacacaag    1680
cccaaggcaa caaagagca actgaaagct gttatggatg atttcgcagc ttttgtagag    1740
aagtgctgca aggctgacga taaggagacc tgctttgccg aggagggtaa aaaacttgtt    1800
gctgcaagtc aagctgcctt aggcttagct cccatgaccc agacaacgtc cttgaagaca    1860
agctgggtta actgctctaa catgatcgat gaaattataa cacacttaaa gcagccacct    1920
ttgcctttgc tggacttcaa caacctcaat ggggaagacc aagacattct gatgaaaat     1980 aaccttcgaa ggccaaacct ggaggcattc aacagggctg tcaagagttt acagaacgca    2040
tcagcaattg agagcattct taaaaatctc ctgccatgtc tgcccctggc cacggccgca    2100
cccacgcgac atccaatcca tatcaaggac ggtgactgga atgaattccg gaggaaactg    2160
acgttctatc tgaaaaccct tgagaatgcg caggctcaac agacgacttt gagcctcgcg    2220
atcttttag                                                            2229

<210> SEQ ID NO 2
<211> LENGTH: 763
<212> TYPE: PRT
<213> ORGANISM: Artificial Sequence
<220> FEATURE:
<223> OTHER INFORMATION: HSA-hIL-11

<400> SEQUENCE: 2

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205
```

-continued

```
Arg Ala Phe Lys Ala Trp Ala Val Ala Arg Leu Ser Gln Arg Phe Pro
    210                 215                 220
Lys Ala Glu Phe Ala Glu Val Ser Lys Leu Val Thr Asp Leu Thr Lys
225                 230                 235                 240
Val His Thr Glu Cys Cys His Gly Asp Leu Leu Glu Cys Ala Asp Asp
                    245                 250                 255
Arg Ala Asp Leu Ala Lys Tyr Ile Cys Glu Asn Gln Asp Ser Ile Ser
                260                 265                 270
Ser Lys Leu Lys Glu Cys Cys Glu Lys Pro Leu Leu Glu Lys Ser His
            275                 280                 285
Cys Ile Ala Glu Val Glu Asn Asp Glu Met Pro Ala Asp Leu Pro Ser
290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                325                 330                 335
Arg His Pro Asp Tyr Ser Val Val Leu Leu Leu Arg Leu Ala Lys Thr
                340                 345                 350
Tyr Glu Thr Thr Leu Glu Lys Cys Cys Ala Ala Ala Asp Pro His Glu
            355                 360                 365
Cys Tyr Ala Lys Val Phe Asp Glu Phe Lys Pro Leu Val Glu Glu Pro
370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Gln Val Ser Thr Pro Thr Leu Val Glu Val Ser Arg Asn Leu Gly Lys
            420                 425                 430
Val Gly Ser Lys Cys Cys Lys His Pro Glu Ala Lys Arg Met Pro Cys
            435                 440                 445
Ala Glu Asp Tyr Leu Ser Val Val Leu Asn Gln Leu Cys Val Leu His
    450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
                485                 490                 495
Tyr Val Pro Lys Glu Phe Asn Ala Glu Thr Phe Thr Phe His Ala Asp
                500                 505                 510
Ile Cys Thr Leu Ser Glu Lys Glu Arg Gln Ile Lys Lys Gln Thr Ala
            515                 520                 525
Leu Val Glu Leu Val Lys His Lys Pro Lys Ala Thr Lys Glu Gln Leu
            530                 535                 540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Glu Gly Lys Lys Leu Val
                565                 570                 575
Ala Ala Ser Gln Ala Ala Leu Gly Leu Pro Gly Pro Pro Gly Pro
                580                 585                 590
Pro Arg Val Ser Pro Asp Pro Arg Ala Glu Leu Asp Ser Thr Val Leu
            595                 600                 605
Leu Thr Arg Ser Leu Leu Ala Asp Thr Arg Gln Leu Ala Ala Gln Leu
        610                 615                 620
Arg Asp Lys Phe Pro Ala Asp Gly Asp His Asn Leu Asp Ser Leu Pro
```

```
                    625                 630                 635                 640
Thr Leu Ala Met Ser Ala Gly Ala Leu Gly Ala Leu Gln Leu Pro Gly
                645                 650                 655
Val Leu Thr Arg Leu Arg Ala Asp Leu Leu Ser Tyr Leu Arg His Val
                660                 665                 670
Gln Trp Leu Arg Arg Ala Gly Gly Ser Ser Leu Lys Thr Leu Glu Pro
            675                 680                 685
Glu Leu Gly Thr Leu Gln Ala Arg Leu Asp Arg Leu Leu Arg Arg Leu
        690                 695                 700
Gln Leu Leu Met Ser Arg Leu Ala Leu Pro Gln Pro Pro Pro Asp Pro
705                 710                 715                 720
Pro Ala Pro Pro Leu Ala Pro Pro Ser Ser Ala Trp Gly Gly Ile Arg
                725                 730                 735
Ala Ala His Ala Ile Leu Gly Gly Leu His Leu Thr Leu Asp Trp Ala
                740                 745                 750
Val Arg Gly Leu Leu Leu Leu Lys Thr Arg Leu
            755                 760

<210> SEQ ID NO 3
<211> LENGTH: 2229
<212> TYPE: DNA
<213> ORGANISM: Artificial Sequence
<220> FEATURE:
<223> OTHER INFORMATION: DNA of HSA-hIL-3

<400> SEQUENCE: 3
atgaagtggg taacctttat ttcccttctt tttctcttta gctcggctta ttccaggggt      60
gtgtttcgtc gagatgcaca caagagtgag gttgctcatc ggtttaaaga tttgggagaa     120
gaaaatttca agcccttggt gttgattgcc tttgctcagt atcttcagca gtgtccattt     180
gaagatcatg taaaattagt gaatgaagta actgaatttg caaaaacatg tgttgctgat     240
gagtcagctg aaaattgtga caaatcactt catacccttt ttggagacaa attatgcaca     300
gttgcaactc ttcgtgaaac ctatggtgaa atggctgact gctgtgcaaa acaagaacct     360
gagagaaatg aatgcttctt gcaacacaaa gatgacaacc caaacctccc ccgattggtg     420
agaccagagg ttgatgtgat gtgcactgct tttcatgaca atgaagagac attttttgaaa    480
aaatacttat atgaaattgc cagaagacat ccttactttt atgccccgga actccttttc     540
tttgctaaaa ggtataaagc tgctttttaca gaatgttgcc aagctgctga taaagctgcc    600
tgcctgttgc caaagctcga tgaacttcgg gatgaaggga aggcttcgtc tgccaaacag     660
agactcaagt gtgccagtct ccaaaaattt ggagaaagag ctttcaaagc atgggcagta     720
gctcgcctga gccagagatt cccaaagct gagtttgcag aagtttccaa gttagtgaca     780
gatcttacca agtccacac ggaatgctgc catggagatc tgcttgaatg tgctgatgac     840
agggcggacc ttgccaagta tatctgtgaa atcaagatt cgatctccag taaactgaag     900
gaatgctgtg aaaaacctct gttggaaaaa tcccactgca ttgccgaagt ggaaatgat     960
gagatgcctg ctgacttgcc ttcattagct gctgattttg ttgaaagtaa ggatgtttgc    1020
aaaaactatg ctgaggcaaa ggatgtcttc ctgggcatgt ttttgtatga atatgcaaga    1080
aggcatcctg attactctgt cgtgctgctg ctgagacttg ccaagacata tgaaaccact    1140
ctagagaagt gctgtgccgc tgcagatcct catgaatgct atgccaaagt gttcgatgaa    1200
tttaaacctc ttgtggaaga gcctcagaat ttaatcaaac aaaattgtga gcttttttgag    1260
cagcttggag agtacaaatt ccagaatgcg ctattagttc gttacaccaa gaaagtaccc    1320
```

-continued

```
caagtgtcaa ctccaactct tgtagaggtc tcaagaaacc taggaaaagt gggcagcaaa    1380
tgttgtaaac atcctgaagc aaaaagaatg ccctgtgcag aagactatct atccgtggtc    1440
ctgaaccagt tatgtgtgtt gcatgagaaa acgccagtaa gtgacagagt caccaaatgc    1500
tgcacagaat ccttggtgaa caggcgacca tgcttttcag ctctggaagt cgatgaaaca    1560
tacgttccca aagagtttaa tgctgaaaca ttcaccttcc atgcagatat atgcacactt    1620
tctgagaagg agagacaaat caagaaacaa actgcacttg ttgagcttgt gaaacacaag    1680
cccaaggcaa caaagagca actgaaagct gttatggatg atttcgcagc ttttgtagag    1740
aagtgctgca aggctgacga taaggagacc tgctttgccg aggagggtaa aaaacttgtt    1800
gctgcaagtc aagctgcctt aggcttagct cccatgaccc agacaacgtc cttgaagaca    1860
agctgggtta actgctctaa catgatcgat gaaattataa cacacttaaa gcagccacct    1920
ttgcctttgc tggacttcaa caacctcaat ggggaagacc aagacattct gatggaaaat    1980
aaccttcgaa ggccaaacct ggaggcattc aacagggctg tcaagagttt acagaacgca    2040
tcagcaattg agagcattct taaaaatctc ctgccatgtc tgccccctggc cacggccgca    2100 cccacgcgac atccaatcca tatcaaggac ggtgactgga atgaattccg gaggaaactg    2160
acgttctatc tgaaaaccct tgagaatgcg caggctcaac agacgacttt gagcctcgcg    2220
atcttttag                                                             2229
```

<210> SEQ ID NO 4
<211> LENGTH: 718
<212> TYPE: PRT
<213> ORGANISM: Artificial Sequence
<220> FEATURE:
<223> OTHER INFORMATION: HSA-hIL-3

<400> SEQUENCE: 4

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190
```

-continued

```
Ser Ala Lys Gln Arg Leu Lys Cys Ala Ser Leu Gln Lys Phe Gly Glu
    195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Glu Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Gly Lys Lys Leu Val
                565                 570                 575

Ala Ala Ser Gln Ala Ala Leu Gly Leu Ala Pro Met Thr Gln Thr Thr
            580                 585                 590

Ser Leu Lys Thr Ser Trp Val Asn Cys Ser Asn Met Ile Asp Glu Ile
        595                 600                 605

Ile Thr His Leu Lys Gln Pro Pro Leu Pro Leu Leu Asp Phe Asn Asn
```

```
        610             615             620
Leu Asn Gly Glu Asp Gln Asp Ile Leu Met Glu Asn Asn Leu Arg Arg
625                 630                 635                 640

Pro Asn Leu Glu Ala Phe Asn Arg Ala Val Lys Ser Leu Gln Asn Ala
                645                 650                 655

Ser Ala Ile Glu Ser Ile Leu Lys Asn Leu Leu Pro Cys Leu Pro Leu
                660                 665                 670

Ala Thr Ala Ala Pro Thr Arg His Pro Ile His Ile Lys Asp Gly Asp
            675                 680                 685

Trp Asn Glu Phe Arg Arg Lys Leu Thr Phe Tyr Leu Lys Thr Leu Glu
690                 695                 700

Asn Ala Gln Ala Gln Gln Thr Thr Leu Ser Leu Ala Ile Phe
705                 710                 715

<210> SEQ ID NO 5
<211> LENGTH: 2313
<212> TYPE: DNA
<213> ORGANISM: Artificial Sequence
<220> FEATURE:
<223> OTHER INFORMATION: DNA of HSA-hEPO

<400> SEQUENCE: 5
atgaagtggg taacctttat ttcccttctt tttctcttta gctcggctta ttccaggggt      60
gtgtttcgtc gagatgcaca agagtgag gttgctcatc ggtttaaaga tttgggagaa      120
gaaaatttca agccttggt gttgattgcc tttgctcagt atcttcagca gtgtccattt      180
gaagatcatg taaaattagt gaatgaagta actgaatttg caaaaacatg tgttgctgat      240
gagtcagctg aaaattgtga caaatcactt catacccttt ttggagacaa attatgcaca      300
gttgcaactc ttcgtgaaac ctatggtgaa atggctgact gctgtgcaaa acaagaacct      360
gagagaaatg aatgcttctt gcaacacaaa gatgacaacc caaacctccc ccgattggtg      420
agaccagagg ttgatgtgat gtgcactgct tttcatgaca tgaagagac attttttgaaa      480 aaatacttat atgaaattgc cagaagacat ccttactttt atgccccgga actccttttc      540
tttgctaaaa ggtataaagc tgcttttaca gaatgttgcc aagctgctga taaagctgcc      600
tgcctgttgc caaagctcga tgaacttcgg gatgaaggga aggcttcgtc tgccaaacag      660
agactcaagt gtgccagtct ccaaaaattt ggagaaagag ctttcaaagc atgggcagta      720
gctcgcctga ccagagatt tcccaaagct gagtttgcag aagtttccaa gttagtgaca      780
gatcttacca aagtccacac ggaatgctgc catggagatc tgcttgaatg tgctgatgac      840
agggcggacc ttgccaagta tatctgtgaa aatcaagatt cgatctccag taaactgaag      900
gaatgctgtg aaaaacctct gttggaaaaa tcccactgca ttgccgaagt ggaaaatgat      960
gagatgcctg ctgacttgcc ttcattagct gctgattttg ttgaaagtaa ggatgtttgc     1020
aaaaactatg ctgaggcaaa ggatgtcttc ctgggcatgt ttttgtatga atatgcaaga     1080
aggcatcctg attactctgt cgtgctgctg ctgagacttg ccaagacata tgaaaccact     1140
ctagagaagt gctgtgccgc tgcagatcct catgaatgct atgccaaagt gttcgatgaa     1200
tttaaaccct tgtggaaga gcctcagaat ttaatcaaac aaaattgtga gcttttgag     1260 cagcttggag agtacaaatt ccagaatgcg ctattagttc gttacaccaa gaaagtaccc     1320
caagtgtcaa ctccaactct gtgtagaggtc tcaagaaacc taggaaagt gggcagcaaa     1380 tgttgtaaac atcctgaagc aaaaagaatg ccctgtgcag aagactatct atccgtggtc     1440
ctgaaccagt tatgtgtgtt gcatgagaaa acgccagtaa gtgacagagt caccaaatgc     1500
```

-continued

```
tgcacagaat ccttggtgaa caggcgacca tgcttttcag ctctggaagt cgatgaaaca    1560
tacgttccca aagagtttaa tgctgaaaca ttcaccttcc atgcagatat atgcacactt    1620
tctgagaagg agacaaat caagaaacaa actgcacttg ttgagcttgt gaaacacaag      1680
cccaaggcaa caaaagagca actgaaagct gttatggatg atttcgcagc ttttgtagag    1740
aagtgctgca aggctgacga taaggagacc tgctttgccg aggagggtaa aaaacttgtt    1800
gctgcaagtc aagctgcctt aggcttaatc tgtgacagcc gagtcctgga gaggtacctc    1860
ttggaggcca aggaggccga gaatatcacg acgggctgtg ctgaacactg cagcttgaat    1920
gagaatatca ctgtcccaga caccaaagtt aatttctatg cctggaagag gatggaggtc    1980
gggcagcagg ccgtagaagt ctggcagggc ctggccctgc tgtcggaagc tgtcctgcgg    2040
ggccaggccc tgttggtcaa ctcttcccag ccgtgggagc ccctgcagct gcatgtggat    2100
aaagccgtca gtggccttcg cagcctcacc actctgcttc gggctctgcg agcccagaag    2160
gaagccatct cccctccaga tgcggcctca gctgctccac tccgaacaat cactgctgac    2220
actttccgca aactcttccg agtctactcc aatttcctcc ggggaaagct gaagctgtac    2280
acaggggagg cctgcaggac aggggacaga tga                                 2313
```

<210> SEQ ID NO 6
<211> LENGTH: 746
<212> TYPE: PRT
<213> ORGANISM: Artificial Sequence
<220> FEATURE:
<223> OTHER INFORMATION: HSA-hEPO

<400> SEQUENCE: 6

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
```

-continued

```
              210                 215                 220
Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                    245                 250                 255

Arg Ala Asp Leu Ala Lys Tyr Ile Cys Glu Asn Gln Asp Ser Ile Ser
                    260                 265                 270

Ser Lys Leu Lys Glu Cys Cys Glu Lys Pro Leu Leu Glu Lys Ser His
                    275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                    325                 330                 335

Arg His Pro Asp Tyr Ser Val Val Leu Leu Leu Arg Leu Ala Lys Thr
                    340                 345                 350

Tyr Glu Thr Thr Leu Glu Lys Cys Cys Ala Ala Ala Asp Pro His Glu
                    355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                    405                 410                 415

Glu Val Ser Thr Pro Thr Leu Val Glu Val Ser Arg Asn Leu Gly Lys
                    420                 425                 430

Val Gly Ser Lys Cys Cys Lys His Pro Glu Ala Lys Arg Met Pro Cys
                    435                 440                 445

Ala Glu Asp Tyr Leu Ser Val Val Leu Asn Gln Leu Cys Val Leu His
                    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                    485                 490                 495

Tyr Val Pro Lys Glu Phe Asn Ala Glu Thr Phe Thr Phe His Ala Asp
                    500                 505                 510

Ile Cys Thr Leu Ser Glu Lys Glu Arg Gln Ile Lys Lys Gln Thr Ala
                    515                 520                 525

Leu Val Glu Leu Val Lys His Lys Pro Lys Ala Thr Lys Glu Gln Leu
                    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Gly Lys Lys Leu Val
                    565                 570                 575

Ala Ala Ser Gln Ala Ala Leu Gly Leu Ile Cys Asp Ser Arg Val Leu
                    580                 585                 590

Glu Arg Tyr Leu Leu Glu Ala Lys Glu Ala Glu Asn Ile Thr Thr Gly
                    595                 600                 605

Cys Ala Glu His Cys Ser Leu Asn Glu Asn Ile Thr Val Pro Asp Thr
                    610                 615                 620

Lys Val Asn Phe Tyr Ala Trp Lys Arg Met Glu Val Gly Gln Gln Ala
625                 630                 635                 640
```

```
Val Glu Val Trp Gln Gly Leu Ala Leu Leu Ser Glu Ala Val Leu Arg
            645                 650                 655
Gly Gln Ala Leu Leu Val Asn Ser Ser Gln Pro Trp Glu Pro Leu Gln
            660                 665                 670
Leu His Val Asp Lys Ala Val Ser Gly Leu Arg Ser Leu Thr Thr Leu
            675                 680                 685
Leu Arg Ala Leu Arg Ala Gln Lys Glu Ala Ile Ser Pro Pro Asp Ala
            690                 695                 700
Ala Ser Ala Ala Pro Leu Arg Thr Ile Thr Ala Asp Thr Phe Arg Lys
705                 710                 715                 720
Leu Phe Arg Val Tyr Ser Asn Phe Leu Arg Gly Lys Leu Lys Leu Tyr
                725                 730                 735
Thr Gly Glu Ala Cys Arg Thr Gly Asp Arg
            740                 745

<210> SEQ ID NO 7
<211> LENGTH: 2352
<212> TYPE: DNA
<213> ORGANISM: Artificial Sequence
<220> FEATURE:
<223> OTHER INFORMATION: DNA of HSA-GCSF

<400> SEQUENCE: 7
atgaagtggg taacctttat ttcccttctt tttctcttta gctcggctta ttccaggggt      60
gtgtttcgtc gagatgcaca caagagtgag gttgctcatc ggtttaaaga tttgggagaa     120
gaaaatttca agccttggt gttgattgcc tttgctcagt atcttcagca gtgtccattt      180
gaagatcatg taaaattagt gaatgaagta actgaatttg caaaaacatg tgttgctgat     240
gagtcagctg aaaattgtga caaatcactt cataccctt ttggagacaa attatgcaca     300
gttgcaactc ttcgtgaaac ctatggtgaa atggctgact gctgtgcaaa acaagaacct     360
gagagaaatg aatgcttctt gcaacacaaa gatgacaacc caaacctccc ccgattggtg     420
agaccagagg ttgatgtgat gtgcactgct tttcatgaca tgaagagaca tttttgaaa     480 aaatacttat atgaaattgc cagaagacat ccttactttt atgccccgga actccttttc     540
tttgctaaaa ggtataaagc tgcttttaca gaatgttgcc aagctgctga taaagctgcc     600
tgcctgttgc caaagctcga tgaacttcgg gatgaaggga aggcttcgtc tgccaaacag     660
agactcaagt gtgccagtct ccaaaaattt ggagaaagag ctttcaaagc atgggcagta     720
gctcgcctga gccagagatt tcccaaagct gagtttgcag aagtttccaa gttagtgaca     780
gatcttacca agtccacac ggaatgctgc catggagatc tgcttgaatg tgctgatgac     840
agggcggacc ttgccaagta tatctgtgaa aatcaagatt cgatctccag taaactgaag     900
gaatgctgtg aaaaacctct gttggaaaaa tcccactgca ttgccgaagt ggaaaatgat     960
gagatgcctg ctgacttgcc ttcattagct gctgattttg ttgaaagtaa ggatgtttgc    1020
aaaaactatg ctgaggcaaa ggatgtcttc ctgggcatgt ttttgtatga atatgcaaga    1080
aggcatcctg attactctgt cgtgctgctg ctgagacttg ccaagacata tgaaaccact    1140
ctagagaagt gctgtgccgc tgcagatcct catgaatgct atgccaaagt gttcgatgaa    1200
tttaaacctc ttgtggaaga gcctcagaat ttaatcaaac aaaattgtga gcttttgag    1260 cagcttggag agtacaaatt ccagaatgcg ctattagttc gttacaccaa gaaagtaccc    1320
caagtgtcaa ctccaactct gtagaggtc tcaagaaacc taggaaaagt gggcagcaaa    1380
tgttgtaaac atcctgaagc aaaaagaatg ccctgtgcag aagactatct atccgtggtc    1440
```

-continued

```
ctgaaccagt tatgtgtgtt gcatgagaaa acgccagtaa gtgacagagt caccaaatgc    1500
tgcacagaat ccttggtgaa caggcgacca tgcttttcag ctctggaagt cgatgaaaca    1560
tacgttccca aagagtttaa tgctgaaaca ttcaccttcc atgcagatat atgcacactt    1620
tctgagaagg agagacaaat caagaaacaa actgcacttg ttgagcttgt gaaacacaag    1680
cccaaggcaa caaagagca actgaaagct gttatggatg atttcgcagc ttttgtagag     1740
aagtgctgca aggctgacga taaggagacc tgctttgccg aggagggtaa aaaacttgtt    1800
gctgcaagtc aagctgcctt aggcttaacc cccctgggcc ctgccagctc cctgccccag    1860
agcttcctgc tcaagtgctt agagcaagtg aggaagatcc agggcgatgg cgcagcgctc    1920
caggagaagc tgtgtgccac ctacaagctg tgccacccg aggagctggt gctgctcgga     1980
cactctctgg gcatcccctg gctcccctg agcagctgcc ccagccaggc cctgcagctg     2040
gcaggctgct tgagccaact ccatagcggc ctttttcctct accaggggct cctgcaggcc    2100
ctggaaggga tctcccccga gttgggtccc accttggaca cactgcagct ggacgtcgcc    2160
gactttgcca ccaccatctg gcagcagatg aagaactgg gaatggcccc tgccctgcag     2220
cccacccagg gtgccatgcc ggccttcgcc tctgctttcc agcgccgggc aggaggggtc    2280
ctagttgcct cccatctgca gagcttcctg gaggtgtcgt accgcgttct acgccacctt    2340 gcccagcct ga                                                         2352
```

<210> SEQ ID NO 8
<211> LENGTH: 759
<212> TYPE: PRT
<213> ORGANISM: Artificial Sequence
<220> FEATURE:
<223> OTHER INFORMATION: HSA-GCSF

<400> SEQUENCE: 8

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190
```

```
Ser Ala Lys Gln Arg Leu Lys Cys Ala Ser Leu Gln Lys Phe Gly Glu
    195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Glu Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Gly Lys Lys Leu Val
                565                 570                 575

Ala Ala Ser Gln Ala Ala Leu Gly Leu Thr Pro Leu Gly Pro Ala Ser
            580                 585                 590

Ser Leu Pro Gln Ser Phe Leu Leu Lys Cys Leu Glu Gln Val Arg Lys
        595                 600                 605

Ile Gln Gly Asp Gly Ala Ala Leu Gln Glu Lys Leu Cys Ala Thr Tyr
```

```
            610                 615                 620
Lys Leu Cys His Pro Glu Glu Leu Val Leu Leu Gly His Ser Leu Gly
625                 630                 635                 640

Ile Pro Trp Ala Pro Leu Ser Ser Cys Pro Ser Gln Ala Leu Gln Leu
                645                 650                 655

Ala Gly Cys Leu Ser Gln Leu His Ser Gly Leu Phe Leu Tyr Gln Gly
            660                 665                 670

Leu Leu Gln Ala Leu Glu Gly Ile Ser Pro Glu Leu Gly Pro Thr Leu
        675                 680                 685

Asp Thr Leu Gln Leu Asp Val Ala Asp Phe Ala Thr Thr Ile Trp Gln
    690                 695                 700

Gln Met Glu Glu Leu Gly Met Ala Pro Ala Leu Gln Pro Thr Gln Gly
705                 710                 715                 720

Ala Met Pro Ala Phe Ala Ser Ala Phe Gln Arg Arg Ala Gly Gly Val
                725                 730                 735

Leu Val Ala Ser His Leu Gln Ser Phe Leu Glu Val Ser Tyr Arg Val
            740                 745                 750

Leu Arg His Leu Ala Gln Pro
        755

<210> SEQ ID NO 9
<211> LENGTH: 2211
<212> TYPE: DNA
<213> ORGANISM: Artificial Sequence
<220> FEATURE:
<223> OTHER INFORMATION: DNA of HSA-GMCSF

<400> SEQUENCE: 9
atgaagtggg taacctttat ttcccttctt tttctcttta gctcggctta ttccaggggt       60
gtgtttcgtc gagatgcaca caagagtgag gttgctcatc ggtttaaaga tttgggagaa      120
gaaaatttca aagccttggt gttgattgcc tttgctcagt atcttcagca gtgtccattt      180
gaagatcatg taaaattagt gaatgaagta actgaatttg caaaaacatg tgttgctgat      240
gagtcagctg aaaattgtga caaatcactt catacccttt ttggagacaa attatgcaca      300
gttgcaactc ttcgtgaaac ctatggtgaa atggctgact gctgtgcaaa acaagaacct      360
gagagaaatg aatgcttctt gcaacacaaa gatgacaacc caaacctccc ccgattggtg      420
agaccagagg ttgatgtgat gtgcactgct tttcatgaca atgaagagac attttttgaaa     480 aaatacttat atgaaattgc cagaagacat ccttactttt atgccccgga actcctttttc    540 tttgctaaaa ggtataaagc tgcttttaca gaatgttgcc aagctgctga taaagctgcc      600
tgcctgttgc caaagctcga tgaacttcgg gatgaaggga aggcttcgtc tgccaaacag      660
agactcaagt gtgccagtct ccaaaaattt ggagaaagag ctttcaaagc atgggcagta      720
gctcgcctga gccagagatt tcccaaagct gagtttgcag aagtttccaa gttagtgaca      780
gatcttacca agtccacac ggaatgctgc catggagatc tgcttgaatg tgctgatgac      840
agggcggacc ttgccaagta tatctgtgaa aatcaagatt cgatctccag taaactgaag      900
gaatgctgtg aaaaacctct gttggaaaaa tcccactgca ttgccgaagt ggaaaatgat      960
gagatgcctg ctgacttgcc ttcattagct gctgattttg ttgaaagtaa ggatgtttgc     1020
aaaaactatg ctgaggcaaa ggatgtcttc ctgggcatgt ttttgtatga atatgcaaga     1080
aggcatcctg attactctgt cgtgctgctg ctgagacttg ccaagacata tgaaaccact     1140
ctagagaagt gctgtgccgc tgcagatcct catgaatgct atgccaaagt gttcgatgaa     1200
```

-continued

```
tttaaacctc ttgtggaaga gcctcagaat ttaatcaaac aaaattgtga gcttttttgag    1260 cagcttggag agtacaaatt ccagaatgcg ctattagttc gttacaccaa gaaagtaccc    1320
caagtgtcaa ctccaactct tgtagaggtc tcaagaaacc taggaaaagt gggcagcaaa    1380
tgttgtaaac atcctgaagc aaaaagaatg ccctgtgcag aagactatct atccgtggtc    1440
ctgaaccagt tatgtgtgtt gcatgagaaa acgccagtaa gtgacagagt caccaaatgc    1500
tgcacagaat ccttggtgaa caggcgacca tgcttttcag ctctggaagt cgatgaaaca    1560
tacgttccca agagtttaa tgctgaaaca ttcaccttcc atgcagatat atgcacactt    1620
tctgagaagg agagacaaat caagaaacaa actgcacttg ttgagcttgt gaaacacaag    1680
cccaaggcaa caaagagca actgaaagct gttatggatg atttcgcagc ttttgtagag    1740
aagtgctgca aggctgacga taaggagacc tgctttgccg aggagggtaa aaaacttgtt    1800
gctgcaagtc aagctgcctt aggcttagca cccgcccgct cgcccagccc cagcacgcag    1860
ccctgggagc atgtgaatgc catccaggag gcccggcgtc tcctgaacct gagtagagac    1920
actgctgctg agatgaatga acagtagaa gtcatctcag aaatgtttga cctccaggag    1980
ccgacctgcc tacagacccg cctggagctg tacaagcagg gcctgcgggg cagcctcacc    2040
aagctcaagg gccccttgac catgatggcc agccactaca gcagcactg ccctccaacc    2100 ccggaaactt cctgtgcaac ccagattatc acctttgaaa gtttcaaaga gaacctgaag    2160
gactttctgc ttgtcatccc ctttgactgc tgggagccag tccaggagtg a             2211
```

<210> SEQ ID NO 10
<211> LENGTH: 712
<212> TYPE: PRT
<213> ORGANISM: Artificial Sequence
<220> FEATURE:
<223> OTHER INFORMATION: HSA-GMCSF

<400> SEQUENCE: 10

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190
```

```
Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Glu Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Ala Pro Ala Arg Ser Pro Ser
            580                 585                 590

Pro Ser Thr Gln Pro Trp Glu His Val Asn Ala Ile Gln Glu Ala Arg
        595                 600                 605
```

```
        Arg Leu Leu Asn Leu Ser Arg Asp Thr Ala Ala Glu Met Asn Glu Thr
            610                 615                 620

Val Glu Val Ile Ser Glu Met Phe Asp Leu Gln Glu Pro Thr Cys Leu
        625                 630                 635                 640

Gln Thr Arg Leu Glu Leu Tyr Lys Gln Gly Leu Arg Gly Ser Leu Thr
                        645                 650                 655

Lys Leu Lys Gly Pro Leu Thr Met Met Ala Ser His Tyr Lys Gln His
                    660                 665                 670

Cys Pro Pro Thr Pro Glu Thr Ser Cys Ala Thr Gln Ile Ile Thr Phe
                675                 680                 685

Glu Ser Phe Lys Glu Asn Leu Lys Asp Phe Leu Leu Val Ile Pro Phe
            690                 695                 700

Asp Cys Trp Glu Pro Val Gln Glu
        705                 710

<210> SEQ ID NO 11
<211> LENGTH: 1830
<212> TYPE: DNA
<213> ORGANISM: Homo sapiens

<400> SEQUENCE: 11
```

| | | | | | |
|---|---|---|---|---|---|
| atgaagtggg | taacctttat | ttcccttctt | tttctcttta | gctcggctta | ttccaggggt | 60 |
| gtgtttcgtc | gagatgcaca | caagagtgag | gttgctcatc | ggtttaaaga | tttgggagaa | 120 |
| gaaaatttca | agccttggt | gttgattgcc | tttgctcagt | atcttcagca | gtgtccattt | 180 |
| gaagatcatg | taaaattagt | gaatgaagta | actgaatttg | caaaaacatg | tgttgctgat | 240 |
| gagtcagctg | aaaattgtga | caaatcactt | catacccttt | ttggagacaa | attatgcaca | 300 |
| gttgcaactc | ttcgtgaaac | ctatggtgaa | atggctgact | gctgtgcaaa | acaagaacct | 360 |
| gagagaaatg | aatgcttctt | gcaacacaaa | gatgacaacc | caaacctccc | ccgattggtg | 420 |
| agaccagagg | ttgatgtgat | gtgcactgct | tttcatgaca | atgaagagac | attttttgaaa | 480 |
| aaatacttat | atgaaattgc | cagaagacat | ccttactttt | atgccccgga | actccttttc | 540 |
| tttgctaaaa | ggtataaagc | tgcttttaca | gaatgttgcc | aagctgctga | taaagctgcc | 600 |
| tgcctgttgc | caaagctcga | tgaacttcgg | gatgaaggga | aggcttcgtc | tgccaaacag | 660 |
| agactcaagt | gtgccagtct | ccaaaaattt | ggagaaagag | ctttcaaagc | atgggcagta | 720 |
| gctcgcctga | gccagagatt | tcccaaagct | gagtttgcag | aagtttccaa | gttagtgaca | 780 |
| gatcttacca | aagtccacac | ggaatgctgc | catggagatc | tgcttgaatg | tgctgatgac | 840 |
| agggcggacc | ttgccaagta | tatctgtgaa | aatcaagatt | cgatctccag | taaactgaag | 900 |
| gaatgctgtg | aaaaacctct | gttggaaaaa | tcccactgca | ttgccgaagt | ggaaaatgat | 960 |
| gagatgcctg | ctgacttgcc | ttcattagct | gctgattttg | ttgaaagtaa | ggatgtttgc | 1020 |
| aaaaactatg | ctgaggcaaa | ggatgtcttc | ctgggcatgt | ttttgtatga | atatgcaaga | 1080 |
| aggcatcctg | attactctgt | cgtgctgctg | ctgagacttg | ccaagacata | tgaaaccact | 1140 |
| ctagagaagt | gctgtgccgc | tgcagatcct | catgaatgct | atgccaaagt | gttcgatgaa | 1200 |
| tttaaacctc | ttgtggaaga | gcctcagaat | ttaatcaaac | aaaattgtga | gcttttgag | 1260 |
| cagcttggag | agtacaaatt | ccagaatgcg | ctattagttc | gttacaccaa | gaaagtaccc | 1320 |
| caagtgtcaa | ctccaactct | tgtagaggtc | tcaagaaacc | taggaaaagt | gggcagcaaa | 1380 |
| tgttgtaaac | atcctgaagc | aaaaagaatg | ccctgtgcag | aagactatct | atccgtggtc | 1440 |
| ctgaaccagt | tatgtgtgtt | gcatgagaaa | acgccagtaa | gtgacagagt | caccaaatgc | 1500 |

-continued

```
tgcacagaat ccttggtgaa caggcgacca tgcttttcag ctctggaagt cgatgaaaca    1560
tacgttccca aagagtttaa tgctgaaaca ttcaccttcc atgcagatat atgcacactt    1620
tctgagaagg agagacaaat caagaaacaa actgcacttg ttgagcttgt gaaacacaag    1680
cccaaggcaa caaagagca actgaaagct gttatggatg atttcgcagc ttttgtagag    1740
aagtgctgca aggctgacga taaggagacc tgctttgccg aggagggtaa aaaacttgtt    1800
gctgcaagtc aagctgcctt aggcttataa                                    1830
```

<210> SEQ ID NO 12
<211> LENGTH: 609
<212> TYPE: PRT
<213> ORGANISM: Homo sapiens

<400> SEQUENCE: 12

```
Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Glu Val Glu Asn Asp
305                 310                 315                 320
```

Glu Met Pro Ala Asp Leu Pro Ser Leu Ala Ala Asp Phe Val Glu Ser
            325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
            355                 360                 365

Leu Leu Leu Arg Leu Ala Lys Thr Tyr Glu Thr Thr Leu Glu Lys Cys
            370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Glu Val Ser Thr Pro Thr Leu Val
            435                 440                 445

Glu Val Ser Arg Asn Leu Gly Lys Val Gly Ser Lys Cys Cys Lys His
            450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
            515                 520                 525

Glu Thr Phe Thr Phe His Ala Asp Ile Cys Thr Leu Ser Glu Lys Glu
            530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
            595                 600                 605

Leu

<210> SEQ ID NO 13
<211> LENGTH: 600
<212> TYPE: DNA
<213> ORGANISM: Homo sapiens

<400> SEQUENCE: 13
atgaactgtg tttgccgcct ggtcctggtc gtgctgagcc tgtggccaga tacagctgtc    60
gcccctgggc caccacctgg ccccccctcga gtttccccag accctcgggc cgagctggac   120
agcaccgtgc tcctgacccg ctctctcctg gcggacacgc ggcagctggc tgcacagctg   180
agggacaaat cccagctga cggggaccac aacctggatt ccctgcccac cctggccatg   240
agtgcggggg cactgggagc tctacagctc ccaggtgtgc tgacaaggct gcgagcggac   300
ctactgtcct acctgcggca cgtgcagtgg ctgcgccggg caggtggctc ttccctgaag   360
accctggagc ccgagctggg caccctgcag gcccgactgg accggctgct gcgccggctg   420

```
cagctcctga tgtcccgcct ggccctgccc cagccacccc cggacccgcc ggcgccccg      480 ctggcgcccc cctcctcagc ctgggggggc atcagggccg cccacgccat cctggggggg      540
ctgcacctga cacttgactg ggccgtgagg ggactgctgc tgctgaagac tcggctgtga      600
```

<210> SEQ ID NO 14
<211> LENGTH: 199
<212> TYPE: PRT
<213> ORGANISM: Homo sapiens

<400> SEQUENCE: 14

```
Met Asn Cys Val Cys Arg Leu Val Leu Val Leu Ser Leu Trp Pro
1               5                   10                  15

Asp Thr Ala Val Ala Pro Gly Pro Pro Gly Pro Pro Arg Val Ser
                20                  25                  30

Pro Asp Pro Arg Ala Glu Leu Asp Ser Thr Val Leu Leu Thr Arg Ser
            35                  40                  45

Leu Leu Ala Asp Thr Arg Gln Leu Ala Ala Gln Leu Arg Asp Lys Phe
    50                  55                  60

Pro Ala Asp Gly Asp His Asn Leu Asp Ser Leu Pro Thr Leu Ala Met
65                  70                  75                  80

Ser Ala Gly Ala Leu Gly Ala Leu Gln Leu Pro Gly Val Leu Thr Arg
                85                  90                  95

Leu Arg Ala Asp Leu Leu Ser Tyr Leu Arg His Val Gln Trp Leu Arg
                100                 105                 110

Arg Ala Gly Gly Ser Ser Leu Lys Thr Leu Glu Pro Glu Leu Gly Thr
            115                 120                 125

Leu Gln Ala Arg Leu Asp Arg Leu Leu Arg Arg Leu Gln Leu Leu Met
    130                 135                 140

Ser Arg Leu Ala Leu Pro Gln Pro Pro Asp Pro Pro Ala Pro Pro
145                 150                 155                 160

Leu Ala Pro Pro Ser Ser Ala Trp Gly Gly Ile Arg Ala Ala His Ala
                165                 170                 175

Ile Leu Gly Gly Leu His Leu Thr Leu Asp Trp Ala Val Arg Gly Leu
                180                 185                 190

Leu Leu Leu Lys Thr Arg Leu
            195
```

<210> SEQ ID NO 15
<211> LENGTH: 582
<212> TYPE: DNA
<213> ORGANISM: Homo sapiens

<400> SEQUENCE: 15

```
atgggggtgc acgaatgtcc tgcctggctg tggcttctcc tgtccctgct gtcgctccct      60
ctgggcctcc cagtcctggg cgccccacca cgcctcatct gtgacagccg agtcctggag     120
aggtacctct tggaggccaa ggaggccgag aatatcacga cgggctgtgc tgaacactgc     180
agcttgaatg agaatatcac tgtcccagac accaaagtta atttctatgc ctggaagagg     240
atggaggtcg ggcagcaggc cgtagaagtc tggcagggcc tggccctgct gtcggaagct     300
gtcctgcggg gccaggccct gttggtcaac tcttcccagc cgtgggagcc cctgcagctg     360
catgtggata agccgtcag tggccttcgc agcctcacca ctctgcttcg ggctctgcga     420
gcccagaagg aagccatctc ccctccagat gcggcctcag ctgctccact ccgaacaatc     480
actgctgaca ctttccgcaa actcttccga gtctactcca atttcctccg gggaaagctg     540
```
aagctgtaca caggggaggc ctgcaggaca ggggacagat ga                        582

<210> SEQ ID NO 16
<211> LENGTH: 193
<212> TYPE: PRT
<213> ORGANISM: Homo sapiens

<400> SEQUENCE: 16

Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Arg Ala Gln Lys Glu
130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 17
<211> LENGTH: 630
<212> TYPE: DNA
<213> ORGANISM: Homo sapiens

<400> SEQUENCE: 17
ggatccatgg ctggacctgc cacccagagc cccatgaagc tgatggccct gcagctgctg    60
ctgtggcaca gtgcactctg gacagtgcag gaagccaccc ccctgggccc tgccagctcc   120 ctgcccccaga gcttcctgct caagtgctta gagcaagtga ggaagatcca gggcgatggc   180
gcagcgctcc aggagaagct gtgtgccacc tacaagctgt gccaccccga ggagctggtg   240
ctgctcggac actctctggg catccctggg ctcccctga gcagctgccc cagccaggcc    300
ctgcagctgg caggctgctt gagccaactc atagcggcc ttttcctcta ccaggggctc    360
ctgcaggccc tggaagggat ctccccccag ttgggtccca ccttggacac actgcagctg   420
gacgtcgccg actttgccac caccatctgg cagcagatgg aagaactggg aatggcccct   480
gccctgcagc ccacccaggg tgccatgccg gccttcgcct ctgctttcca cgccgggca    540 ggaggggtcc tagttgcctc ccatctgcag agcttcctgg aggtgtcgta ccgcgttcta   600
cgccaccttg cccagccctg agccgaattc                                    630

<210> SEQ ID NO 18
<211> LENGTH: 204
<212> TYPE: PRT
<213> ORGANISM: Homo sapiens

<400> SEQUENCE: 18

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
    50                  55                  60

Leu Cys Ala Thr Tyr Lys Leu Cys His Pro Glu Glu Leu Val Leu Leu
65                  70                  75                  80

Gly His Ser Leu Gly Ile Pro Trp Ala Pro Leu Ser Ser Cys Pro Ser
                85                  90                  95

Gln Ala Leu Gln Leu Ala Gly Cys Leu Ser Gln Leu His Ser Gly Leu
            100                 105                 110

Phe Leu Tyr Gln Gly Leu Leu Gln Ala Leu Glu Gly Ile Ser Pro Glu
        115                 120                 125

Leu Gly Pro Thr Leu Asp Thr Leu Gln Leu Asp Val Ala Asp Phe Ala
    130                 135                 140

Thr Thr Ile Trp Gln Gln Met Glu Glu Leu Gly Met Ala Pro Ala Leu
145                 150                 155                 160

Gln Pro Thr Gln Gly Ala Met Pro Ala Phe Ala Ser Ala Phe Gln Arg
                165                 170                 175

Arg Ala Gly Gly Val Leu Val Ala Ser His Leu Gln Ser Phe Leu Glu
            180                 185                 190

Val Ser Tyr Arg Val Leu Arg His Leu Ala Gln Pro
        195                 200

<210> SEQ ID NO 19
<211> LENGTH: 448
<212> TYPE: DNA
<213> ORGANISM: Homo sapiens

<400> SEQUENCE: 19
atgtggctgc agagcctgct gctcttgggc actgtggcct gcagcatctc tgcacccgcc      60
cgctcgccca gccccagcac gcagccctgg gagcatgtga atgccatcca ggaggcccgg     120
cgtctcctga acctgagtag agacactgct gctgagatga atgaaacagt agaagtcatc     180
tcagaaatgt ttgacctcca ggagccgacc tgcctacaga cccgcctgga gctgtacaag     240
cagggcctgc ggggcagcct caccaagctc aagggcccct tgaccatgat ggccagccac     300
tacaagcagc actgccctcc aaccccggaa acttcctgtg caacccagat tatcaccttt     360
gaaagtttca agagaacct gaaggacttt ctgcttgtca tccccttgta ctgctgggag     420
ccagtccagg agtgagaccg gccagatg                                        448

<210> SEQ ID NO 20
<211> LENGTH: 144
<212> TYPE: PRT
<213> ORGANISM: Homo sapiens

<400> SEQUENCE: 20

Met Trp Leu Gln Ser Leu Leu Leu Leu Gly Thr Val Ala Cys Ser Ile

```
                1               5              10              15
Ser Ala Pro Ala Arg Ser Pro Ser Pro Ser Thr Gln Pro Trp Glu His
                    20                  25                  30

Val Asn Ala Ile Gln Glu Ala Arg Arg Leu Leu Asn Leu Ser Arg Asp
            35                  40                  45

Thr Ala Ala Glu Met Asn Glu Thr Val Glu Val Ile Ser Glu Met Phe
        50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
                100                 105                 110

Cys Ala Thr Gln Ile Ile Thr Phe Glu Ser Phe Lys Glu Asn Leu Lys
            115                 120                 125

Asp Phe Leu Leu Val Ile Pro Phe Asp Cys Trp Glu Pro Val Gln Glu
        130                 135                 140
```

<210> SEQ ID NO 21
<211> LENGTH: 459
<212> TYPE: DNA
<213> ORGANISM: Homo sapiens

<400> SEQUENCE: 21

```
atgagccgcc tgcccgtcct gctcctgctc caactcctgg tccgccccgg actccaagct    60
cccatgaccc agacaacgtc cttgaagaca agctgggtta actgctctaa catgatcgat   120
gaaattataa cacacttaaa gcagccacct ttgccttgc tggacttcaa caacctcaat    180
ggggaagacc aagacattct gatggaaaat aaccttcgaa ggccaaacct ggaggcattc   240
aacagggctg tcaagagttt acagaacgca tcagcaattg agagcattct taaaaatctc   300
ctgccatgtc tgcccctggc cacggccgca cccacgcgac atccaatcca tatcaaggac   360
ggtgactgga atgaattccg gaggaaactg acgttctatc tgaaaaccct gagaatgcg    420
caggctcaac agacgacttt gagcctcgcg atcttttag                          459
```

<210> SEQ ID NO 22
<211> LENGTH: 152
<212> TYPE: PRT
<213> ORGANISM: Homo sapiens

<400> SEQUENCE: 22

```
Met Ser Arg Leu Pro Val Leu Leu Leu Gln Leu Leu Val Arg Pro
1               5                  10                  15

Gly Leu Gln Ala Pro Met Thr Gln Thr Thr Ser Leu Lys Thr Ser Trp
                20                  25                  30

Val Asn Cys Ser Asn Met Ile Asp Glu Ile Ile Thr His Leu Lys Gln
            35                  40                  45

Pro Pro Leu Pro Leu Leu Asp Phe Asn Asn Leu Asn Gly Glu Asp Gln
        50                  55                  60

Asp Ile Leu Met Glu Asn Asn Leu Arg Arg Pro Asn Leu Glu Ala Phe
65                  70                  75                  80

Asn Arg Ala Val Lys Ser Leu Gln Asn Ala Ser Ala Ile Glu Ser Ile
                85                  90                  95

Leu Lys Asn Leu Leu Pro Cys Leu Pro Leu Ala Thr Ala Ala Pro Thr
                100                 105                 110
```

```
Arg His Pro Ile His Ile Lys Asp Gly Asp Trp Asn Glu Phe Arg Arg
    115                 120                 125

Lys Leu Thr Phe Tyr Leu Lys Thr Leu Glu Asn Ala Gln Ala Gln Gln
    130                 135                 140

Thr Thr Leu Ser Leu Ala Ile Phe
145                 150

<210> SEQ ID NO 23
<211> LENGTH: 30
<212> TYPE: DNA
<213> ORGANISM: Artificial Sequence
<220> FEATURE:
<223> OTHER INFORMATION: Cloning primer

<400> SEQUENCE: 23
gaattcatga agtgggtaac ctttatttcc                                    30

<210> SEQ ID NO 24
<211> LENGTH: 33
<212> TYPE: DNA
<213> ORGANISM: Artificial Sequence
<220> FEATURE:
<223> OTHER INFORMATION: Cloning primer

<400> SEQUENCE: 24
gaattcttat aagcctaagg cagcttgact tgc                                33

<210> SEQ ID NO 25
<211> LENGTH: 28
<212> TYPE: DNA
<213> ORGANISM: Artificial Sequence
<220> FEATURE:
<223> OTHER INFORMATION: Cloning primer

<400> SEQUENCE: 25
catatgaact gtgtttgccg cctggtcc                                      28

<210> SEQ ID NO 26
<211> LENGTH: 25
<212> TYPE: DNA
<213> ORGANISM: Artificial Sequence
<220> FEATURE:
<223> OTHER INFORMATION: Cloning primer

<400> SEQUENCE: 26
gatatgtatg acacatttaa ttccc                                         25

<210> SEQ ID NO 27
<211> LENGTH: 26
<212> TYPE: DNA
<213> ORGANISM: Artificial Sequence
<220> FEATURE:
<223> OTHER INFORMATION: Cloning primer

<400> SEQUENCE: 27
ggatccatgg gggtgcacga atgtcc                                        26

<210> SEQ ID NO 28
<211> LENGTH: 26
<212> TYPE: DNA
<213> ORGANISM: Artificial Sequence
<220> FEATURE:
<223> OTHER INFORMATION: Cloning primer

<400> SEQUENCE: 28
```

```
gaattctcat ctgtccsctg tcctgc                                            26
```

<210> SEQ ID NO 29
<211> LENGTH: 25
<212> TYPE: DNA
<213> ORGANISM: Artificial Sequence
<220> FEATURE:
<223> OTHER INFORMATION: Cloning primer

<400> SEQUENCE: 29

```
ggatccatgg ctggacctgc caccc                                             25
```

<210> SEQ ID NO 30
<211> LENGTH: 26
<212> TYPE: DNA
<213> ORGANISM: Artificial Sequence
<220> FEATURE:
<223> OTHER INFORMATION: Cloning primer

<400> SEQUENCE: 30

```
gaattctcag ggctgggcaa ggtggc                                            26
```

<210> SEQ ID NO 31
<211> LENGTH: 28
<212> TYPE: DNA
<213> ORGANISM: Artificial Sequence
<220> FEATURE:
<223> OTHER INFORMATION: Cloning primer

<400> SEQUENCE: 31

```
ggatccatgt ggctgcagag cctgctgc                                          28
```

<210> SEQ ID NO 32
<211> LENGTH: 25
<212> TYPE: DNA
<213> ORGANISM: Artificial Sequence
<220> FEATURE:
<223> OTHER INFORMATION: Cloning primer

<400> SEQUENCE: 32

```
gaattctcac tcctggactg gctcc                                             25
```

<210> SEQ ID NO 33
<211> LENGTH: 33
<212> TYPE: DNA
<213> ORGANISM: Artificial Sequence
<220> FEATURE:
<223> OTHER INFORMATION: Cloning primer

<400> SEQUENCE: 33

```
ctgccttagg cttacctggg ccaccacctg gcc                                    33
```

<210> SEQ ID NO 34
<211> LENGTH: 29
<212> TYPE: DNA
<213> ORGANISM: Artificial Sequence
<220> FEATURE:
<223> OTHER INFORMATION: Cloning primer

<400> SEQUENCE: 34

```
tgtcgactca cagccgagtc ttcagcagc                                         29
```

<210> SEQ ID NO 35
<211> LENGTH: 33
<212> TYPE: DNA
<213> ORGANISM: Artificial Sequence

```
<220> FEATURE:
<223> OTHER INFORMATION: Cloning primer

<400> SEQUENCE: 35
ctgccttagg cttaatctgt gacagccgag tcc                              33

<210> SEQ ID NO 36
<211> LENGTH: 28
<212> TYPE: DNA
<213> ORGANISM: Artificial Sequence
<220> FEATURE:
<223> OTHER INFORMATION: Cloning primer

<400> SEQUENCE: 36
cactcgagtc atctgtcccc tgtcctgc                                    28

<210> SEQ ID NO 37
<211> LENGTH: 35
<212> TYPE: DNA
<213> ORGANISM: Artificial Sequence
<220> FEATURE:
<223> OTHER INFORMATION: Cloning primer

<400> SEQUENCE: 37
ctgccttagg cttaaccccc ctgggccctg ccagc                            35

<210> SEQ ID NO 38
<211> LENGTH: 25
<212> TYPE: DNA
<213> ORGANISM: Artificial Sequence
<220> FEATURE:
<223> OTHER INFORMATION: Cloning primer

<400> SEQUENCE: 38
ctcgagtcag ggctgggcaa ggtgg                                       25

<210> SEQ ID NO 39
<211> LENGTH: 35
<212> TYPE: DNA
<213> ORGANISM: Artificial Sequence
<220> FEATURE:
<223> OTHER INFORMATION: Cloning primer

<400> SEQUENCE: 39
actccttagg cttagcaccc gcccgctcgc ccagc                            35

<210> SEQ ID NO 40
<211> LENGTH: 25
<212> TYPE: DNA
<213> ORGANISM: Artificial Sequence
<220> FEATURE:
<223> OTHER INFORMATION: Cloning primer

<400> SEQUENCE: 40
ctcgagtcac tcctggactg gctcc                                       25
```

RECOMBINANT HUMAN ALBUMIN-ERYTHROPOIETIN FUSION PROTEINS WITH LONG-LASTING BIOLOGICAL EFFECTS

CROSS REFERENCE TO RELATED APPLICATION

This application is a Continuation Application of patent application Ser. No. 10/609,346, filed Jun. 26, 2003, now issued as U.S. Pat. No. 7,244,833 B2, which claims the priority of Provisional Application Ser. No. 60/392,948, filed Jul. 1, 2002. All parent applications are hereby incorporated by reference in their entirety.

BACKGROUND OF THE INVENTION

1. Field of the Invention

This invention relates to the manufacture and use of recombinant albumin fusion proteins and combinations thereof, and particularly to yeast expressed fusion proteins formed between human albumin and bioactive molecules such as therapeutic proteins and peptides, and more particularly to yeast expressed fusion proteins formed between human albumin and cell proliferation stimulatory factor (CPSF), such as, blood cell-stimulatory factors, erythropoietin (EPO), interleukins (ILs), stem cell factor (SCF), thrombopoietin (TPO), granulocyte colony stimulating factor (G-CSF), and granulocyte macrophage colony stimulating factor (GM-CSF).

2. Description of Related Art

1. Albumin

Albumin is a soluble, monomeric protein which comprises about one-half of the blood serum protein. Albumin functions primarily as a carrier protein for steroids, fatty acids, and thyroid hormones and plays a role in stabilizing extracellular fluid volume. Mutations in this gene on chromosome 4 result in various anomalous proteins. Albumin is a globular unglycosylated serum protein of molecular weight 65,000. The human albumin gene is 16,961 nucleotides long from the putative 'cap' site to the first poly(A) addition site. It is split into 15 exons which are symmetrically placed within the 3 domains that are thought to have arisen by triplication of a single primordial domain. Albumin is synthesized in the liver as pre-pro-albumin which has an N-terminal peptide that is removed before the nascent protein is released from the rough endoplasmic reticulum. The product, proalbumin, is in turn cleaved in the Golgi vesicles to produce the secreted albumin. HSA has 35 cysteins; in blood this protein monomer has 17 disulfide linkage (Brown, J. R. "Albumin structure, Function, and Uses" Pergamon, New York, 1977). HSA is misfolded when produced intracellularly in yeast without its amino terminal secretion peptide sequence. This conclusion is based on its insolubility, loss of great than 90% of its antigenicity (as compared to human-derived HSA), and formation of large protein aggregates. At present albumin for clinical use is produced by extraction from human blood. The production of recombinant albumin in microorganisms has been disclosed in EP 330 451 and EP 361 991.

Albumin is a stable plasma transporter function provided by any albumin variant and in particular by human albumin. HSA is highly polymorphic and more than 30 different genetic alleles have been reported (Weikamp L, R, et al., Ann. Hum. Genet., 37 219-226, 1973). The albumin molecule, whose three-dimensional structure has been characterized by X-ray diffraction (Carter D. C. et al., Science 244, 1195-1198, 1989), was chosen to provide the stable transporter function because it is the most abundant plasma protein (40 g per liter in human), it has a high plasma half-life (14-20 days in human, Waldmann T. A., in "Albumin Structure, Function and Uses", Rosenoer V. M. et al (eds), Pergamon Press, Oxford, 255-275,1977), and above all it has the advantage of being devoid of enzymatic function, thus permitting its therapeutic utilization at high dose.

2. Interleukin-11 (IL-11)

Human IL-11 (Paul et al. (1990), Pro. Natl. Acad. Sci. 87:7512) has been identified in medium conditioned by primate bone marrow-derived stromal cells. IL-11 is expressed in cells of mesenchymal origin, such as stromal fibroblasts, fetal lung fibroblasts and trophoblasts.

IL-11, also called adipogenesis inhibitory factor (AGIF), acts on hematopoietic progenitor cells and stromal cells (Kawashima, I., et al., Progress in Growth Factor Research, 4,191 1992). The mature molecule is a non-glycosylation protein, 178aa in length, and has an apparent molecular weight 23 KD (as determined by SDS-PAGE). Human IL-11 gene consists of five exons and four introns and was mapped on chromosome 19 at band 19q13.3-q13.4. IL-11 exhibits a primary structure unrelated to that of known cytokines, but it often acts similar to other cytokines, notably IL-6. IL-11 is a pleiotropic growth factor effecting hematopoietic and non-hematopoietic cells, often in synergy with interleukins, colony stimulating factors, or stem cell factor. In hematopoietic cells, IL-11 can enhance megakaryopoiesis, stimulate early and intermediate myeloid progenitor cells, initiate proliferation of dormant hematopoietic progenitor cells, and stimulate T-cell-dependent development of antibody-secreting B-cells. In non-hematopoietic cells, IL-11 can inhibit adipogenesis, and mediates the hepatic acute phase response. IL-11 stimulated the production of erythrocytes was reported only by Quesniaux, V F J., et al., Blood, 80, 1218 (1992).

Human IL-11 (e.g., NEURMEGA®, manufactured by America Home Products Company) has been approved for clinical trials in the United States for directly stimulating the proliferation of hematopoietic stem cells and megakaryocyte progenitor cells and inducing megakaryocyte maturation, resulting in increased platelet production. It has been used for the prevention of severe thrombocytopenia and the reduction of the need for platelet transfusion following myelosuppressive chemotherapy.

3. Erythropoietin (EPO)

Erythropoietin (EPO) is a glycoprotein that is the principle regulator of red blood cells growth and differentiation (U.S. Pat. No. 5,547,933). Erythropoiesis, the production of red blood cells, occurs continuously throughout the human life span to offset cell destruction. Erythropoiesis is a very precisely controlled physiological mechanism enabling sufficient numbers of red blood cells to be available in the blood for proper tissue oxygenation, but not so many that the cells would impede circulation. The formation of red blood cells occurs in the bone marrow and is under the control of the hormone EPO.

EPO is an acidic glycoprotein (~30,400 Daltons) produced primarily by the kidney and is the principal factor regulating red blood cell production in mammals. Renal production of EPO is regulated by changes in oxygen availability. Under conditions of hypoxia, the level of EPO in the circulation increases and this leads to increased production of red blood cells. The over-expression of EPO may be associated with certain pathophysiological conditions. Polycythemia exists when there is an overproduction of red blood cells (RBCs). Primary polycythemias, such as Polycythemia vera, are caused by EPO-independent growth of erythrocytic progenitors from abnormal stem cells and low to normal levels of EPO are found in the serum of affected patients.

On the other hand, various types of secondary polycythemias are associated with the production of higher than normal levels of EPO. The overproduction of EPO may be an adaptive response associated with conditions that produce tissue hypoxia, such as living at high altitude, chronic obstructive pulmonary disease, cyanotic heart disease, sleep apnea, high-affinity hemoglobinopathy, smoking, or localized renal hypoxia. In other instances, excessive EPO levels are the result of production by neoplastic cells. Cases of increased EPO production and erythrocytosis have been recorded for patients with renal carcinomas, benign renal tumors, Wilms' tumors, hepatomas liver carcinomas, cerebellar hemangioblastomas, adrenal gland tumors, smooth muscle tumors, and leiomyomas.

Deficient EPO production is found in conjunction with certain forms of anemias. These include anemia of renal failure and end-stage renal disease, anemias of chronic disorders [chronic infections, autoimmune diseases, rheumatoid arthritis, AIDS, malignancies], anemia of prematurity, anemia of hypothyroidism, and anemia of malnutrition. Many of these conditions are associated with the generation of IL-1 and TNF-, factors that have been shown to be inhibitors of EPO activity. Other forms of anemias, on the other hand, are due to EPO-independent causes and affected individuals show elevated levels of EPO. These forms include aplastic anemias, iron deficiency anemias, thalassemias, megaloblastic anemias, pure red cell aplasias, and myelodysplastic syndromes.

The amount of erythropoietin in the circulation is increased under conditions of hypoxia when oxygen transport by blood cells in the circulation is reduced. Hypoxia may be caused by loss of large amounts of blood through hemorrhage, destruction of red blood cells by over-exposure to radiation, reduction in oxygen intake due to high altitudes or prolonged unconsciousness, or various forms of anemia. In response to tissues undergoing hypoxic stress, erythropoietin will increase red blood cell production by stimulating the conversion of primitive precursor cells in the bone marrow into proerythroblasts which subsequently mature, synthesize hemoglobin and are released into the circulation as red blood cells. When the number of red blood cells in circulation is greater than needed for normal tissue oxygen requirements, erythropoietin in circulation is decreased.

EPO may occur in three forms: alpha-, beta and asialo-EPO. The alpha- and beta-forms differ slightly in carbohydrate components, but have the same potency, biological activity and molecular weight. The asialo-form is an alpha- or beta-form with the terminal carbohydrate (sialic acid) removed. EPO is present in very low concentrations in plasma when the body is in a healthy state wherein tissues receive sufficient oxygenation from the existing number of erythrocytes. This normal low concentration is enough to stimulate replacement of red blood cells which are lost normally through aging. See generally for references, Testa, et al., Exp. Hematol., 8(Supp. 8), 144-152 (1980); Tong, et al., J. Biol. Chem., 256(24), 12666-12672 (1981); Goldwasser, J. Cell. Physiol., 110(Supp 1), 133-135 (1982); Finch, Blood, 60(6), 1241-1246 (1982); Sytowski, et al., Exp. Hematol., 8(Supp 8), 52-64 (1980): Naughton, Ann. Clin. Lab. Sci., 13(5), 432-438 (1983); Weiss, et al., Am. J. Vet. Res., 44(10), 1832-1835 (1983); Lappin, et al., Exp. Hematol., 11(7), 661-666 (1983); Baciu, et al., Ann. N.Y. Acad. Sci., 414, 66-72 (1983); Murphy, et al., Acta Haematologica *Japonica*, 46(7), 1380-1396 (1983); Dessypris, et al., Brit. J. Haematol, 56, 295-306 (1984); and, Emmanouel, et al., Am. J. Physiol., 247 (1 Pt 2), F168-76 (1984).

Because EPO is essential in the process of red blood cell formation, the hormone has potential useful application in both the diagnosis and the treatment of blood disorders characterized by low or defective red blood cell production. See, generally, Pennathur-Das, et al., Blood, 63(5), 1168-71 (1984) and Haddy, Am. Jour. Ped. Hematol./Oncol., 4, 191-196, (1982) relating to erythropoietin in possible therapies for sickle cell disease, and Eschbach, et al. J. Clin. Invest., 74(2), pp. 434-441, (1984), describing a therapeutic regimen for uremic sheep based on in vivo response to erythropoietin-rich plasma infusions and proposing a dosage of 10 U EPO/kg per day for 15-40 days as corrective of anemia of the type associated with chronic renal failure. See also, Krane, Henry Ford Hosp. Med. J., 31(3), 177-181 (1983).

Prior attempts to obtain erythropoietin in good yield from plasma or urine have proven relatively unsuccessful. Complicated and sophisticated laboratory techniques are necessary and generally result in the collection of very small amounts of impure and unstable extracts containing erythropoietin. Genetically engineered EPO (U.S. Pat. No. 5,547,933) has been expressed in Chinese Hamster Ovary cell line (CHO). It has been approved for administration on clinical trials by FDA and now manufactures by Amgen Inc. under the name of EPOGEN.

It has been estimated that the availability of erythropoietin in quantity would allow for treatment each year of anemias of 1,600,000 persons in the United States alone. See, e.g., Morrison, "Bioprocessing in Space—an Overview", pp. 557-571 in The World Biotech Report 1984, Volume 2:USA, (Online Publications, New York, N.Y. 1984). Recent studies have provided a basis for projection of efficacy of erythropoietin therapy in a variety of disease states, disorders and states of hematologic irregularity: Vedovato, et al., Acta. Haematol, 71, 211-213 (1984) (beta-thalassemia); Vichinsky, et al., J. Pediatr., 105(1), 15-21 (1984) (cystic fibrosis); Cotes, et al., Brit. J. Obstet. Gyneacol., 90(4), 304-311 (1983) (pregnancy, menstrual disorders); Haga, et al., Acta. Pediatr. Scand., 72, 827-831 (1983) (early anemia of prematurity); Claus-Walker, et al., Arch. Phys. Med. Rehabil., 65, 370-374 (1984) (spinal cord injury); Dunn, et al., Eur. J. Appl. Physiol., 52, 178-182 (1984) (space flight); Miller, et al., Brit. J. Haematol., 52, 545-590 (1982) (acute blood loss); Udupa, et al., J. Lab. Clin. Med., 103(4), 574-580 and 581-588 (1984); and Lipschitz, et al., Blood, 63(3), 502-509 (1983) (aging); and Dainiak, et al., Cancer, 51(6), 1101-1106 (1983) and Schwartz, et al., Otolaryngol., 109, 269-272 (1983) (various neoplastic disease states accompanied by abnormal erythropoiesis).

4. Granulocyte Colony Stimulating Factor (G-CSF)

Granulocyte colony stimulating factor (G-CSF) is produced by monocytes and fibroblasts. It stimulating granulocyte colony formation, activates neutrophils, differentiates certain myeloid leukemic cell lines and is a potent activator of mature granulocytes (Metcalf D., cell, 43, 5, 1985; Groopman, J. E., Cell,. 50, 5 1987);. Nature human G-CSF is a 19.6 KD glycoprotein having 177 amino acids (Souza, L. M et al., Science, 232, 62, 1986). Human and murine GCSF share approximately 75% amino acid sequence homology and have biology cross-reactivity (Morstyn, G., and Burgess, A., Cancer Res., 48, 5624, 1988). The biological activity of recombinant human G-CSF was measured in a cell proliferation assay using NFS-60 cells (Shurafuji, N et al., Exp. Hematol., 17, 116, 1989). Human G-CSF has been brought to the market under the name of NEUPOGEN® by Amgen, Inc.

5. Granulocyte-Macrophage Colony Stimulating Factor (GM-CSF)

Granulocyte-Macrophage colony stimulating factor (GM-CSF) induces myeloid progenitor cells from bone marrow to from colonies contains macrophages and granulocytes in semisolid media. GM-CSF also acts upon mature macrophages, eosinophils and nutrophils to stimulate various functional activities (Mazur, E., and Cohen, J., Clin Pharmacol. Ther., 46, 250, 1989; Morstyn, T G., and Burgess. A., Cancer Res., 48, 5624, 1988). GM-CSF is an acidic glycoprotein {18-22 KD human (Wong, G., et al., Science, 228, 810, 1986), 23 KD mouse (Metcalf, D., Blood, 67, 257, 1986)} which binds to high affinity receptors on GM-CSF sensitive cells. Although human and mouse GMCSF share 54% amino acid sequence homology, their biological actions are species-specific (Metcalf, D., Blood, 67, 257, 1986). Other growth factors and CSFs modulate receptor binding or actions of GM-CSF (Nicola, N., Immunol. Today, 8, 134, 1987). The proliferative activity of human GMCSF is tested in culture using human TF-1 cells (Kitamura, T., et al., J. cell Physiol., 140, 323, 1989). Human GM-CSF has been brought to the market under the name of LEUKINE® by Immunex, Inc 6. Macrophage Colony Stimulating Factor (M-CSF)

Macrophage Colony Stimulating Factor (M-CSF) is produced by monocytes, fibroblasts and endothelial cells. It stimulates the formation of macrophage colonies (Metcalf, D., Blood, 67, 257, 1986), enhances antibody-dependent cell mediated cytotoxicity by monocytes and macrophages (Mufson, R. A. et al., Cellular Immunol., 119, 182, 1989), and inhibits bone resorption by osteoclasts (Hattersley, G., et al., J. Cell Physiol., 137, 199, 1988). M-CSF is glycoprotein and appears in a few different molecular weight forms due to variation in glycosylation. The peptide has 159 amino acids (Kawasaki, E. S., et al., Science, 230, 291, 1985).

7. Thrombopoietin (TPO)

Thrombopoietin (TPO), the ligand for the receptor encoded by the c-Mpl proto-oncogene, acts as a stimulator of the development of megakaryocyte precursors of platelets. Similar to erythropoietin, TPO leads to an increase in number of circulating platelets. TPO affects the entire thrombopoietic process, with stronger effects in the later stages. Other thrombopoietic cytokines include Stem cell factor (SCF), IL-3, IL-6 and IL-11.

TPO is an approximately 35 KD polypeptide of 335 amino acid. However, due to glycosylation the protein has an apparent molecular weight of 75 KD in SDS-PAGE. The precursor form of TPO consists of 356 amino acids. To generate the mature TPO (335aa), the precursor cleaves a 21 amino acids signal peptide. Human, mouse and dog TPO shows 69-75% amino acid homology. The biological activities of recombinant human TPO was measured in a cell proliferation assay using MO7e cells.

8. Interleukin-3 (IL-3)

Interleukin -3 (IL-3) is one of a large and growing group of growth factors which support the proliferation and differentiation of hematopoietic progenitors as well as cells committed to various myeloid lineages in vitro and in vivo. Human IL-3 has 133 amino acids in mature protein and the glycosylation is not necessary for biological activity in vitro and in vivo. The homology between human and murine IL-3 is considerably less. The initial studies on the biology and biochemistry of IL-3 shows that among the well characterized hematopoietic growth factors, IL-3, is the only factor to be predominantly, if not exclusively, produced by activated T cell in normal cells in mice (Ihele and Weinstein, 1986) as well as in human (Yang and Clark 1998). The structure of IL-3, and the structure and location of its gene, are very much like those of a number of the hematopoietic growth factors and suggest that IL-3 is a member of an evolutionarily related family of growth factors. In preclinical and clinical trials, the most prominent and consistent effect of I1-3 in vivo is a significant increase in the absolute neutrophil count (ANC). In vitro IL-3, in combination with other cytokines such as stem-cell factor, IL-6, IL-1, IL-11, G-CSF. GM-CSF, erythropoietin (EPO), or Thrombopoietin (TPO) induces the proliferation of colony-forming units granulocyte-macrophage (CFU-GM), CFU-Eo, CFU-Baso, burst-forming units-erythroid (BFU-E), colony-forming units-megakaryocyte (CFU-MK) and colony-forming units-granulocyte/erythroid/macrophage/megakaryocyte (CFU-GEMM) in semisolid medium, and it stimulates the proliferation of purified CD34+ cells in suspension culture (Eder, et al., Stem Cell, 15:327-333, 1997).

SUMMARY OF THE INVENTION

The present invention provides compositions, kits and methods for promoting general health or for prevention or treatment of diseases by using novel recombinant fusion proteins of human serum albumin (HSA) and bioactive molecules. The bioactive molecules may be a protein or peptide having a biological function in vitro or in vivo, and preferably, having a therapeutic activity when administered to a human. It is believed that by fusing the bioactive molecule to HSA, stability of the bioactive molecule in vivo may be improved and the therapeutic index increased due to reduced toxicity.

In one aspect of the invention, recombinant fusion proteins of human serum albumin (HSA) and a cell proliferation stimulatory factor (CPSF) are provided 1) to stimulate proliferation of multiple cell types, especially cells of various developmental lineages in the blood, 2) allow a slower release of the HSA-CPSF fusion in the body to maximize the therapeutic effects of the CPSF, and/or 3) to reduce potential side effects or toxicity associated with administration of CPSF alone. In addition, manufacturing processes are provided for efficient, cost-effective production for producing these recombinant proteins in yeast.

In another aspect of the invention, an isolated polynucleotide is provided that encodes a fusion protein formed between HSA and a CPSF, i.e., an HSA/CPSF fusion. The CPSF may include any protein that can stimulate cell proliferation and/or production, preferably selected from the group consisting of colony-stimulatory factors such as colony-stimulating factors such as G-CSF, GM-CSF, eosinophil (EOS)-CSF (i.e. Interleukin-5), macrophage (M)-CSF (CSF-1), multi-CSF (i.e. IL-3) and erythropoietin (EPO); interleukins such as IL-1; IL-2; IL-4; IL-6; IL-7; IL-9; IL-10; IL-11; IL-12; IL-13 and IL-18; Steel factors (SLF: c-kit ligand; Stem-cell factor (SCF); mast cell growth factor); erythroid potentiating activity (EPA), Lactoferrin (LF), H-subunit ferritin (i.e., acidic isoferritin), prostaglandin (PG) E1 and E2, tumor necrosis factor (TNF)-α, -β (i.e. lymphotoxin), interferon (IFN)-α (1b, 2a and 2b), -β, -ω and -γ; transforming growth factor (TGF)-β, activin, inhibin, leukemic inhibitory factor, oncostatin M; and chemokines such as macrophage inflammatory protein (MIP)-1-α (i.e. Stem-cell inhibitor); macrophage inflammatory protein (MIP)-1β; macrophage inflammatory protein (MIP)-2-α (i.e., GRO-β); GRO-α; MIP-2-β (i.e., GRO-γ); platelet factor-4; IL-8; macrophage chemotactic and activating factor and IP-10.

The CPSF may be linked directly to the N-terminus or the C-terminus of HSA to form an HSA-CPSF fusion. Optionally, there is a peptide linker (L) linking HSA and CPSF together to form the fusion protein: HSA-L-CPSF, or CPSF-L-HSA. The length of peptide is preferably between 2-100 aa, more preferably between 5-50 aa, and most preferably between 14-30 aa. The peptide linker may be a flexible linker that minimizes steric hindrance imposed by the bulky HSA protein on CPSF, such as a $(G_4S)_{3-4}$ linker.

In one embodiment, an isolated polynucleotide is provided that encodes a human serum albumin-interleukin-11 fusion protein (HSA-IL-11). The polynucleotide comprises a nucleotide sequence at least 90% identical to SEQ ID NO. 1 (FIG. 1). Preferably, the polynucleotide comprises a nucleotide sequence at least 95% identical to SEQ ID NO. 1. Preferably, the polynucleotide encodes an amino acid sequence comprising SEQ ID NO. 2.

In one embodiment, an isolated polynucleotide is provided that encodes a human serum albumin-interleukin-3 fusion protein (HSA-IL-3). The polynucleotide comprises a nucleotide sequence at least 90% identical to SEQ ID NO. 3. Preferably, the polynucleotide comprises a nucleotide sequence at least 95% identical to SEQ ID NO. 3. Preferably, the polynucleotide encodes an amino acid sequence comprising SEQ ID NO. 4.

In another embodiment, an isolated polynucleotide is provided that encodes a human serum albumin-erythropoietin fusion protein (HSA-EPO). The polynucleotide comprises a nucleotide sequence at least 90% identical to SEQ ID NO. 5. Preferably, the polynucleotide comprises a nucleotide sequence at least 95% identical to SEQ ID NO. 5. Preferably, the polynucleotide encodes an amino acid sequence comprising SEQ ID NO. 6. [HSA-EPO].

In yet another embodiment, an isolated polynucleotide is provided that encodes a human serum albumin-granulocyte colony stimulating factor fusion protein (HSA-GCSF). The polynucleotide comprises a nucleotide sequence at least 90% identical to SEQ ID NO.7. Preferably, the polynucleotide comprises a nucleotide sequence at least 95% identical to SEQ ID NO. 7. Preferably, the polynucleotide encodes an amino acid sequence comprising SEQ ID NO. 8.

In yet another embodiment, an isolated polynucleotide is provided that encodes a human serum albumin-granulocyte macrophage colony stimulating factor fusion protein (HSA-GMCSF). The polynucleotide comprises a nucleotide sequence at least 90% identical to SEQ ID NO. 9. Preferably, the polynucleotide comprises a nucleotide sequence at least 95% identical to SEQ ID NO. 9. Preferably, the polynucleotide encodes an amino acid sequence comprising SEQ ID NO. 10.

In yet another embodiment, an isolated polynucleotide is provided that encodes a human serum albumin-CPSF fusion protein (HSA-CPSF). The polynucleotide comprises a nucleotide sequence at least 90% identical to SEQ ID NO. 11. Preferably, the polynucleotide comprises a nucleotide sequence at least 95% identical to SEQ ID NO. 11. Preferably, the polynucleotide encodes an amino acid sequence comprising SEQ ID NO. 12. Optionally, the polynucleotide further comprises a nucleotide sequence at least 90% identical to SEQ ID NOs. 13, 15, 17, 19, or 21. Preferably, the polynucleotide further comprises a nucleotide sequence encoding an amino acid sequence comprising SEQ ID NOs. 14, 16, 18, 20, or 22.

According to the embodiment, the CPSF may be selected from the group consisting of G-CSF, GM-CSF, (EOS)-CSF, CSF-1, EPO, IL-1; IL-2, IL-3, IL-4; IL-6; IL-7; IL-8, IL-9; IL-10; IL-11; IL-12; IL-13, IL-18, SLF, SCF, mast cell growth factor, EPA, Lactoferrin, H-subunit ferritin, prostaglandin (PG) E1 and E2, TNF-α, TNF-β, IFN-α, IFN-β, IFN-ω, IFN-γ; TGF-β, activin, inhibin, leukemic inhibitory factor, oncostatin M, MIP-1-α, MIP-1β; MIP-2-α, GRO-α; MIP-2-β, platelet factor-4, macrophage chemotactic and activating factor and IP-10.

The fusion protein may be a secretory protein, which binds to a specific antibody of human albumin, and optionally, binds to a specific antibody of the CPSF in this fusion protein.

In another aspect of the invention, a recombinant vector is provided that comprises the sequence of the polynucleotide described above. The recombinant vectors can be an expression vector for expressing the fusion protein encoded by the polynucleotide, HSA-CPSF, HSA-L-CPSF, or CPSF-L-HSA in a host organism. The host organism includes, but is not limited to, mammalian (e.g., human, monkey, mouse, rabbit, etc.), fish, insect, plant, yeast, and bacterium.

In a preferred embodiment, the host organism belongs to a genus of yeast such as *Saccharomyces* (e.g., *S. cerevisiae*), *Pichia, Kluyveromyces, Torulaspora*, and *Schinosaccharomyces*. In a more preferred embodiment, the host organism is *Pichia pastoris*. In a particular embodiment, the recombinant vector is a pPICZ A, pPICZ B, or pPICZ C.

Depending upon the host organism employed in a recombinant process for producing the fusion proteins, the recombinant fusion proteins of the present invention may be glycosylated or may be non-glycosylated. Preferably, when expressed in a host organism, the fusion protein of HSA and CPSF is glycosylated to substantially the same extent as that when expressed in mammalian cells such as Chinese hamster ovarian (CHO) cells, or as that when expressed in *Pichia pastoris*.

In yet another aspect of the invention, a recombinant cell is provided that is capable of expressing the sequence of the polynucleotide described above. The recombinant cell may constitutively or be induced in the presence or absence of an agent to express the fusion protein encoded by the nucleic acid, HSA-CPSF, HSA-L-CPSF, or CPSF-L-HSA in a host organism. The type of the recombinant cell includes, but is not limited to, mammalian (e.g., human, monkey, mouse, rabbit, etc.), fish, insect, plant, yeast, and bacterial cells.

When stored at ambient temperature or a lower temperature, the fusion protein of HSA and CPSF may have a shelf-life 2 times longer, preferably 4 times longer, more preferably 6 times, and most preferably 10 times, longer than that of the CPSF alone (i.e., not fused to HSA) stored under the same condition.

The fusion protein of the present invention may be administered to a mammal, preferably a human, via a variety of routes, including but not limited to, orally, parenterally, intraperitoneally, intravenously, intraarterially, topically, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The antibody may also be delivered to the host locally (e.g., via stents or catheters) and/or in a timed-release manner. In a particular embodiment, the fusion protein is delivered parenterally via injection.

When delivered in vivo to an animal, the fusion protein of HSA and CPSF may have a plasma half-life 2 times longer, preferably 4 times longer, more preferably 6 times, and most preferably 10 times, longer than that of the CPSF alone (i.e., not fused to HSA).

The HSA/CPSF fusion proteins of the present invention may also be administered in combination with a natural or recombinant human albumin, preferably a recombinant human serum albumin at a therapeutically effective dose and ratio.

In yet another aspect of the invention, combinations of different HSA/CPSF fusion proteins of are provided. The specific combinations of these fusion proteins may be administered to a patient to stimulate proliferation of multiple types of cells in the body or to synergistically enhance proliferation of a particular cell type.

In one embodiment, HSA/IL-11 fusion may be combined with HSA/EPO fusion and the resulting combination may be administered to a patient with a hematological disorder to simultaneously stimulate proliferation of erythrocytes and platelets.

In another embodiment, HSA/IL-3 fusion may be combined with HSA/EPO fusion and the resulting combination may be administered to a patient with a hematological disorder to enhance EPO-induced production of erythrocytes.

In yet another embodiment, HSA/IL-3 fusion may be combined with HSA/GCSF fusion and the resulting combination may be administered to a patient with a hematological disorder to increase the production of erythrocytes and neutrophiles, as well as eosinophils.

Alternatively, an HSA/CPSF fusion may be co-administered with a different HSA/CPSF fusion simultaneously or sequentially to a patient in need thereof. This combination therapy may confer synergistic therapeutic effects on the patients.

In yet another aspect of the invention, a method is provided for treating a patient with a CPSF in need thereof. In one embodiment, the method comprises: administering a pharmaceutical formulation comprising a fusion protein of HSA and CPSF to the patient in a therapeutically effective amount. The pharmaceutical formulation may contain any pharmaceutically acceptable excipient and agents that stabilizes the HSA/CPSF fusion protein. The pharmaceutical formulation may further comprise natural or recombinant human serum albumin and/or another, different HSA/CPSF fusion protein.

The pharmaceutical formulation may contain any pharmaceutically acceptable excipient and agents that stabilizes the HSA/CPSF fusion protein. The pharmaceutical formulation may further comprise natural or recombinant human serum albumin and/or another, different HSA/CPSF fusion protein.

In another embodiment, the method comprises: administering a first pharmaceutical formulation comprising a first fusion protein of HSA and a first CPSF to the patient in a therapeutically effective amount; and administering to the patient a second pharmaceutical formulation comprising a second fusion protein of HSA and a second CPSF to the patient in a therapeutically effective amount. Such a combination therapy may confer synergistic therapeutic effects on the patient.

For example, HSA-IL-11 fusion protein may be administered to the patient first, followed by administration of HSA-EPO, HSA-GCSF and/or HSA-GMCSF at therapeutically effective doses and ratios to stimulate proliferation of different types of blood cells.

In yet another aspect of the invention, a kit is provided, comprising: a first fusion protein of HSA and a first CPSF, and a second fusion protein of HSA and a second CPSF. The first and second CPSFs may be the same or different. For example, the first CPSF is IL-11 and the second CPSF is EPO; the first CPSF is IL-3 and the second CPSF is EPO; or the first CPSF is IL-11 and the second CPSF is GCSF.

BRIEF DESCRIPTION OF THE FIGURES

FIG. 1 shows nucleotide and amino acid sequences of embodiments of HSA-CPSF fusion proteins, HSA, and examples of individual CPSFs.

FIG. 6 is a bioassay for human IL-11 and HSA/hIL-11 fusion protein in stimulation of T1165 cell proliferation. A), with hIL-6 antibody in medium; B), without hIL-6 antibody in medium.

FIG. 8 shows the results of a stability test of rHSA/hIL-11 fusion protein under different temperature and its cell proliferation activity. A), 37° C.; B), 50° C.

FIG. 9 shows the results of an in vivo animal test of synergistic effects of a combination of different HSA-CPSFs in stimulating multiple blood cell proliferation, as compared with those when single HSA-CPSFs or CPSFs were administered.

DETAILED DESCRIPTION OF THE INVENTION

Figure 2:
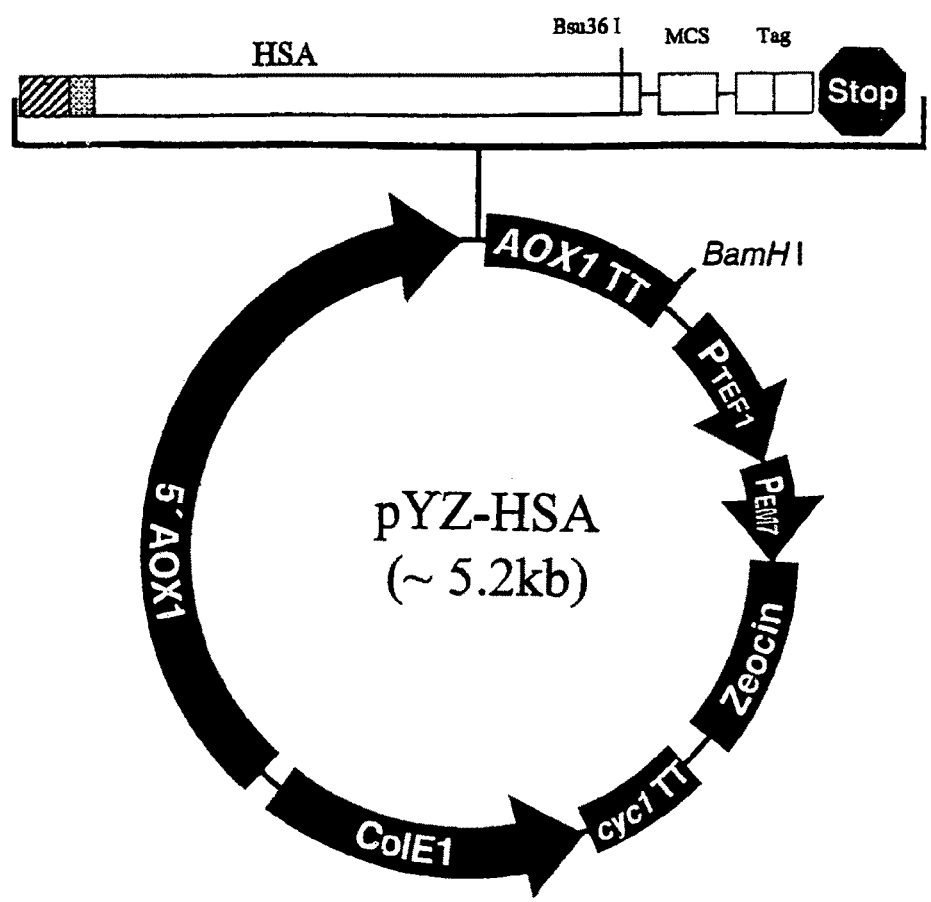
FIG. 2 illustrates a plasmid DNA vector contains the HSA sequence and as a backbone vector for making HSA-CPSF fusion proteins.

The present invention provides innovative compositions, kits and methods for modulating cell proliferation in vivo and more particularly for promoting cell growth for enhancing general health or for treating diseases or undesirable conditions.

In general, recombinant fusion proteins of human serum albumin (HSA) and a cell proliferation stimulatory factor (CPSF) are provided in order to circumvent problems associated with conventional therapy using the CPSF protein itself. Generally, compared with the CPSF protein alone, the inventive fusion proteins of the present invention possess the following advantages: 1) being capable of stimulating proliferation of multiple cell types, especially cells of various developmental lineages in the blood; 2) allowing a slower release of the HSA-CPSF fusion in the body to maximize the therapeutic effects of the CPSF, and/or 3) reducing potential side effects or toxicity associated with administration of CPSF alone.

The present invention also provides a method for treating a patient with a CPSF in need thereof. In one embodiment, the method comprises: administering a pharmaceutical formulation comprising a fusion protein of HSA and CPSF to the patient in a therapeutically effective amount. The pharmaceutical formulation may contain any pharmaceutically acceptable excipient and agents that stabilizes the HSA/CPSF fusion protein. The pharmaceutical formulation may further comprise natural or recombinant human serum albumin and/ or another, different HSA/CPSF fusion protein. The pharmaceutical formulation may contain any pharmaceutically acceptable excipient and agents that stabilizes the HSA/CPSF fusion protein. The pharmaceutical formulation may further comprise natural or recombinant human serum albumin and/or another, different HSA/CPSF fusion protein.

In addition, the present invention also provides manufacturing processes efficient, cost-effective production for producing these recombinant fusion proteins in yeast. In particular, fusion proteins of HSA with each of human IL-11, EPO, G-GCSF and GM-CSF have been expressed in a yeast strain of *Pichia pastoria* and shown to have superior stability in storage and in plasma, and when combined, to possess synergistic effects on the production and growth of multiple types of blood cells.

1. HSA/CPSF Fusion Proteins

In one aspect of the invention, isolated polynucleotides are provided that encode fusion proteins formed between HSA and a CPSF, i.e., HSA/CPSF fusion. It should be noted other types of albumin can also be employed to produce a fusion protein with a CPSF of the present invention.

The CPSF may include any protein that can stimulate cell proliferation and/or production. In a particular embodiment, the CPSF is a hematopoietically active cytokine. Examples of such a CPSF are described in Aggarwal and Puri (1995) "Role of cytokines in immuno-regulation", in "Human Cytokines: Their role in disease and therapy", edited by Aggarwal and Puri, Blackwell Science Inc., Cambridge, Mass., USA, pp 28, which is incorporated herein by reference in its entirety.

Specific examples of the CPSF include, but are not limited to, colony-stimulating factors such as G-CSF, GM-CSF, eosinophil (EOS)-CSF (i.e. Interleukin-5), macrophage (M)-CSF (CSF-1), multi-CSF (i.e. IL-3) and erythropoietin (EPO); interleukins such as IL-1; IL-2; IL-4; IL-6; IL-7; IL-9; IL-10; IL-11; IL-12; IL-13 and IL-18; Steel factors (SLF: c-kit ligand; Stem-cell factor (SCF); mast cell growth factor); erythroid potentiating activity (EPA), Lactoferrin (LF), H-subunit ferritin (i.e., acidic isoferritin), prostaglandin (PG) E1 and E2, tumor necrosis factor (TNF)-α, -β (i.e. lymphotoxin), interferon (IFN)-α(1b, 2a, and 2b), -β, -ω and -γ, transforming growth factor (TGF)-β, activin, inhibin, leukemic inhibitory factor, oncostatin M; and chemokines such as macrophage inflammatory protein (MIP)-1-α (i.e. Stem-cell inhibitor); macrophage inflammatory protein (MIP)-1β; macrophage inflammatory protein (MIP)-2-α (i.e., GRO-β); GRO-α; MIP-2-β (i.e., GRO-γ); platelet factor-4; IL-8; macrophage chemotactic and activating factor and IP-10.

Four distinct colony-stimulating factors (CSFs) that promote survival proliferation and differentiation of bone marrow precursor cells have been well characterized: GM-CSF, G-CSF, M-CSF and Interleukin-3 (IL-3, Multi-CSF). Both GM-CSF and IL-3 are multipotent growth factors, stimulating proliferation of progenitor cells from more than one hematopoietic lineage. In contrast, G-CSF and M-CSF are lineage-restricted hematopoietic growth factors, stimulating the final mitotic divisions and the terminal cellular maturation of partially differentiated hematopoietic progenitors. Erythropoietin is a hematopoietic growth factor that stimulated red blood cell proliferation. Growth factors, such as Stem Cell Factor, all the interleukins, and all the interferon, all are CPSF.

The CPSF may be linked directly to the N-terminus or the C-terminus of HSA to form an HSA-CPSF fusion. Optionally, there is a peptide linker (L) linking HSA and CPSF together to form the fusion protein: HSA-L-CPSF, or CPSF-L-HSA. The length of peptide is preferably between 2-100 aa, more preferably between 5-50 aa, and most preferably between 14-30 aa. The peptide linker may be a flexible linker that minimizes steric hindrance imposed by the bulk HA protein on CPSF, such as a $(G_4S)_{3-4}$ linker. The linker addition may be good for CPSF binds to its receptor.

The fusion protein may be a secretory protein, which binds to a specific antibody of human albumin, and optionally, binds to a specific antibody of the CPSF in this fusion protein.

In one embodiment, an isolated polynucleotide is provided that encodes a human serum albumin-interleukin-11 fusion protein (HSA-IL-11). The polynucleotide comprises a nucleotide sequence at least 90% identical to SEQ ID NO. 1. Preferably, the polynucleotide comprises a nucleotide sequence at least 95% identical to SEQ ID NO. 1. Preferably, the polynucleotide encodes an amino acid sequence comprising SEQ ID NO. 2. [HSA-IL-11].

In one embodiment, an isolated polynucleotide is provided that encodes a human serum albumin-interleukin-3 fusion protein (HSA-IL-3). The polynucleotide comprises a nucleotide sequence at least 90% identical to SEQ ID NO. 3. Preferably, the polynucleotide comprises a nucleotide sequence at least 95% identical to SEQ ID NO. 3. Preferably, the polynucleotide encodes an amino acid sequence comprising SEQ ID NO. 4. [HSA-IL-3].

In another embodiment, an isolated polynucleotide is provided that encodes a human serum albumin-erythropoietin fusion protein (HSA-EPO). The polynucleotide comprises a nucleotide sequence at least 90% identical to SEQ ID NO. 5. Preferably, the polynucleotide comprises a nucleotide sequence at least 95% identical to SEQ ID NO. 5. Preferably, the polynucleotide encodes an amino acid sequence comprising SEQ ID NO. 6 [HSA-EPO].

In yet another embodiment, an isolated polynucleotide is provided that encodes a human serum albumin-granulocyte colony stimulating factor fusion protein (HSA-GCSF). The polynucleotide comprises a nucleotide sequence at least 90% identical to SEQ ID NO. 7. Preferably, the polynucleotide comprises a nucleotide sequence at least 95% identical to SEQ ID NO. 7. Preferably, the polynucleotide encodes an amino acid sequence comprising SEQ ID NO. 8 [HSA-GCSF].

In yet another embodiment, an isolated polynucleotide is provided that encodes a human serum albumin-granulocyte macrophage colony stimulating factor fusion protein (HSA-GMCSF). The polynucleotide comprises a nucleotide sequence at least 90% identical to SEQ ID NO. 9. Preferably, the polynucleotide comprises a nucleotide sequence at least 95% identical to SEQ ID NO. 9. Preferably, the polynucleotide encodes an amino acid sequence comprising SEQ ID NO. 10 [HSA-GMCSF].

In yet another embodiment, an isolated polynucleotide is provided that encodes a human serum albumin-CPSF fusion protein (HSA-CPSF). The polynucleotide comprises a nucleotide sequence at least 90% identical to SEQ ID NO. 11. Preferably, the polynucleotide comprises a nucleotide sequence at least 95% identical to SEQ ID NO. 11. Preferably, the polynucleotide encodes an amino acid sequence comprising SEQ ID NO. 12. Optionally, the polynucleotide further comprises a nucleotide sequence at least 90% identical to SEQ ID NOs. 13, 15, 17, 19, or 21. Preferably, the polynucleotide further comprises a nucleotide sequence encoding an amino acid sequence comprising SEQ ID NOs. 14, 16, 18, 20, or22.

According to the embodiment, the CPSF may be selected from the group consisting of G-CSF, GM-CSF, (EOS)-CSF, CSF-1, EPO, IL-1; IL-2, IL-3, IL-4; IL-6; IL-7; IL-8, IL-9; IL-10; IL-11; IL-12; IL-13, IL-18, SLF, SCF, mast cell growth factor, EPA, Lactoferrin, H-subunit ferritin, prostaglandin (PG) E1 and E2, TNF-α, TNF-β, IFN-α, IFN-β, IFN-ω, IFN-γ; TGF-β, activin, inhibin, leukemic inhibitory factor, oncostatin M, MIP-1-α, MIP-1β; MIP-2-α, GRO-α; MIP-2-β, platelet factor-4, macrophage chemotactic and activating factor and IP-10.

The above-described polynucleotide with a sequence having a certain degree of sequence identity, for example at least 95% "identical" to a reference nucleotide sequence encoding a HSA/CPSF fusion protein, is intended that the polynucleotide sequence is identical to the reference sequence except that the polynucleotide sequence may include up to five point mutations per each 100 nucleotides of the reference nucleotide sequence encoding the HSA/CPSF fusion protein. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to, for instance, the polynucleotide sequence encoding a HSA/CPSF fusion protein can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, Advances in Applied Mathematics 2:482-489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

When stored at ambient temperature or a lower temperature, the fusion protein of HSA and CPSF may have a shelf-life 2 times longer, preferably 4 times longer, more preferably 6 times, and most preferably 10 times, longer than that of the CPSF alone stored under the same condition.

The present invention involves the utilization of albumin as a vehicle to carry a therapeutic protein such as a CPSF that can be used in the treatment of certain diseases such as cancers, or people in need of an increased blood cell proliferation in order to increase the blood cell numbers. The fusion protein of the present invention may be administered to a mammal, preferably a human, via a variety of routes, including but not limited to, orally, parenterally, intraperitoneally, intravenously, intraarterially, topically, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The HSA-CPSF may also be delivered to the host locally (e.g., via stents or catheters) and/or in a timed-release manner. In a particular embodiment, the fusion protein is delivered parenterally via injection.

When delivered in vivo to an animal, the fusion protein of HSA and CPSF may have a plasma half-life 2 times longer, preferably 4 times longer, more preferably 6 times, and most preferably 10 times, longer than that of the CPSF alone.

The HSA/CPSF fusion proteins of the present invention may also be administered in combination with a natural or recombinant human albumin, preferably a recombinant human serum albumin at a therapeutically effective dose and ratio.

It is believed that after fusion with albumin, the CPSF protein can have a longer shelf-life and plasma half-life, which allows cost-effective storage and transportation, as well as reduces amount and/or frequency of drug administration.

It is noted that the same strategy may be used to develop stable fusion proteins with anticancer functions. For example, tumor suppressors, such as p53, pRb, pRb2/p130, and KLF6 may be fused with HSA. Optionally, insulin and insulin-like growth factor may be fused with HSA for therapeutic treatment of diabetes. The gene of antibody from human or other sources with therapeutic function also can be fused with albumin for easy delivery and therapeutic purpose. Antigens against which vaccines are developed can also be fused to albumin for in vivo delivery and increasing the antigenicity of the antigens. Antibody can be fused to albumin and then delivered into blood system to induce an immune response to the invaded foreign antigens such as bacteria, parasites and viruses. In addition anti-aging proteins may be fused with albumin and delivered to humans.

2. Expression of Fusion Proteins in Host Organisms

The polynucleotides encoding the inventive HSA/CPSF fusion proteins can be cloned by recombinant techniques into vectors which are introduced to host cells where the fusion proteins can be expressed.

Generally, host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the polynucleotides encoding HSA/CPSF fusion proteins. The culture conditions, such as temperature, pH and the like, are those previously used with the host cell selected for expression, and will be apparent to the ordinarily skilled artisan.

According to the invention, a recombinant vector is provided that comprises the polynucleotide sequence encoding an HSA/CPSF fusion protein. The recombinant vectors can be an expression vector for expressing the fusion protein encoded by the nucleic acid, HSA-CPSF, HSA-L-CPSF, or CPSF-L-HSA in a host organism. The host organism includes, but is not limited to, mammalian (e.g., human, monkey, mouse, rabbit, etc.), fish, insect, plant, yeast, and bacterium.

Expression of the polynucleotide encoding an HSA/CPSF fusion protein is under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, a tetracycline or tetracycline-like inducible promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the polynucleotide encoding an HSA/CPSF fusion protein.

Also according to the invention, a recombinant cell is provided that is capable of expressing comprises the polynucleotide sequence encoding an HSA/CPSF fusion protein. The recombinant cell may constitutively or be induced in the presence or absence of an agent to express the fusion protein encoded by the nucleic acid, HSA-CPSF, HSA-L-CPSF, or CPSF-L-HSA in a host organism. The type of the recombinant cell includes, but is not limited to, mammalian (e.g., human, monkey, mouse, rabbit, etc.), fish, insect, plant, yeast, and bacterial cell.

In a preferred embodiment, the host organism belongs to a genus of yeast such as *Saccharomyces* (e.g., *S. cerevisiae*), *Pichia, Kluyveromyces, Torulaspora*, and *Schinosaccharomyces*. In a more preferred embodiment, the host organism is *Pichia pastoris*. In a particular embodiment, the recombinant vector is a pPICZ A, pPICZ B, or pPICZ C.

Depending upon the host employed in a recombinant process for producing the fusion proteins, the fusion proteins of the present invention may be glycosylated or may be non-glycosylated. Preferably, when expressed in a host organism, the fusion protein of HSA and CPSF may be glycosylated to substantially the same extent as that when expressed in mammalian cells such as Chinese hamster ovarian (CHO) cells, or as that when expressed in *Pichia pastoris*.

As indicated above, the albumin fusion proteins of the present invention are substantially preferably proteomic and can therefore be generated by the techniques of genetic engineering. The preferred way to obtain these fusion proteins is by the culture of cells transformed, transfected, or infected by vectors expressing the fusion protein. In particular, expression vectors capable of transforming yeasts, especially of the genus *Pichia*, for the secretion of proteins will be used.

It is particularly advantageous to express the HSA/CPSF fusion protein in yeast. Such an expression system allows for production of high quantities of the fusion protein in a mature form, which is secreted into the culture medium, thus facilitating purification.

The development of yeast genetic engineering has been made possible the expression of heterologous genes and the secretion of their protein products from yeast. The advantages of protein secretion (export) of yeast are including but not limited to, high expression level, soluble protein, corrected folding, easy to scale-up and easy for purification.

The HSA/CPSF fusion protein can be secreted into the media of yeast via an albumin natural secretion signal. The polypeptide sequence of HSA fusion protein can be preceded by a signal sequence which serves to direct the proteins into the secretory pathway. In a preferred embodiment the preprosequence of human albumin is used to secret the fusion protein out of yeast cells into the culture medium. Other secret signal peptides, such as the native *Saccharomyces cerevisiae* α-factor secretion signal, can also be used to make fusion protein of the present invention.

Yeast-expressed HSA is soluble and appears to have the same disulfide linkages as the human-blood derived counterpart. If used as a pharmaceutical, which may be potentially used in gram amounts in humans, a recombinant HSA will require a close identity with the natural HSA product. Secreting the HSA/CPSF fusion protein into the growth media of yeast, which is via prepro-amino-terminal processing (no initiator methionine residue), also circumvents the problems associated with preparing yeast extracts, such as the resistance of yeast cells to lysis. In addition, the purity of the product can be increased obtained by placing the product in an environment in which 0.5-1.0% of total yeast proteins is included and the lacks toxic proteins that would contaminate the product.

In a preferred embodiment, a particular species of yeast *Pichia pastoris* is used the system for expressing HSA/CPSF fusions of the present invention. *Pichia pastoris* was developed into an expression system by scientists at Salk Institute Biotechnology/Industry Association (SIBA) and Phillips Petroleum for high-level expression of recombinant proteins. The techniques related to *Pichia* are taught in, for example, U.S. Pat. Nos. 4,683,293, 4,808,537, and 4,857,467.

There are some advantages of using yeast *Pichia pastoris* to expression of HSA and HSA fusion proteins than using other systems. *Pichia pastoris* is a species of yeast genus, *Pichia*. *Pichia* has many of advantages of higher eukaryotic expression systems such as protein processing, protein folding, and posttranslational modification, while being as easy to manipulate as *E. coli* or *Saccharomyces cerevisiae*. It is faster, easier, and less expensive to use than other eukaryotic expression systems such as baculovirus or mammalian tissue culture, and generally gives higher expression levels. *Pichia* has an additional advantage which gives 10 to 100-fold higher heterologous protein expression levels. Those features make *Pichia* very useful as a protein expression system.

Owing to the similarity between *Pichia* and *Saccharomyces*, many techniques developed for *Saccharomyces* may be applied to *Pichia*. These include: transformation by complementation, gene disruption, gene replacement. In addition, the genetic nomenclature used for Sac has been applied to *Pichia*. For example, histidinol dehydrogenase is encoded by the HIS4 gene in both Sac and *Pichia*. The *Pichia* as a methylotrophic yeast is capable of metabolizing methanol as its sole carbon source. The first step in the metabolism of methanol is oxidation of methanol to formaldehyde using molecular oxygen by the enzyme alcohol oxidase. In addition to formaldehyde, this reaction generates hydrogen peroxide. To avoid hydrogen peroxide toxicity, methanol metabolism takes place within a specialized cell organelle, called the peroxisome, which sequesters toxic by-products away from the rest of the cell. Alcohol oxidase has a poor affinity for $O_2$, and *Pichia* compensates by generating large amounts of this enzyme. The promoter regulating the production of alcohol oxidase is the one used to drive heterologous (HSA or HSA fused) protein expression in *Pichia*.

Compared with *Saccharomyces cerevisiae*, *Pichia* may have an advantage in the glycosylation of secreted proteins because it generally does not hyper-glycosylate. Both *Saccharomyces* and *Pichia* have a majority of N-linked glycosylation of the high-mannose type; however, the length of the oligosaccharide chains added post-translationally to proteins in *Pichia* (average 8-14 mannose residues per side chain) is much shorter than those in *Saccharomyces* (50-150 mannose residues). Very little O-linked glycosylation has been observed in *Pichia*. In addition, *Saccharomyces* core oligosaccharide have terminal α-1,3 glycan linkages whereas *Pichia* does not. It is believed that the α-1,3 glycan linkages in glycosylated proteins produced from *Saccharomyces* are primarily responsible for the hyper-antigenic nature of those proteins making them particularly unsuitable for therapeutic use. Although not yet proven, this is predicted to be less of a problem for glycoprotein generated in *Pichia*, because it may resemble the glycoprotein structure of higher eukaryotes. Protein expressed as a secreted form for correctly refolding and easy to purification of HSA and HSA fusion proteins.

Watanabe, et al. (2001) "In vitro and in vivo properties of recombinant human serum albumin from *Pichia pastoris* purified by a method of short processing time", Pharm Res 2001 December:18(12):1775; and Kobayashi, K et al. (1998) "The development of recombinant human serum albumin" Ther Apher, November:2(4):257-62.

There are many expression systems available for expressing in *Pichia*, such as EasySelect™ *Pichia* Expression Kit from Invitrogen, Inc. On this vector, an AOX1 promoter is used to allow methanol-inducible high level expression in *Pichia* and a Zeocin™ resistance as selective market for the recombinants from the transformation. Promoters (transcription initiation region) are very important in expression of fusion proteins in this invention.

AOX1 gene promoter is a very strong promoter in yeast system, especially in *Pichia*. Two Alcohol Oxidase Proteins are coded in *Pichia* for alcohol oxidase—AOX1 and AOX2. The AOX1 gene is responsible for the vast majority of alcohol oxidase activity in the cell. Expression of the AOX1 gene is tightly regulated and induced by methanol to very high levels, typically ≧30% of the total soluble protein in cells grown with methanol as the carbon source. The AOX1 gene has been isolated and a plasmid-bone version of the AOX1 promoter is used to drive expression of the gene of interest encoding the desired heterologous protein (Ellis et al., 1985; Koutz et al., 1989; Tschopp et al., 1987a). While AOX2 is about 97% homologous to AOX 1, growth on methanol is much slower than with AOX1. This slow growth on methanol allows isolation of Mut$^s$ strains (aox1). Except AOX1 gene promoter, other promoters can also be used to driver HSA fusion gene in yeast. They are including the promoter from, but not limited to, PGK1, GAPDH, Gal1, Gal10, CYC1, PH05, TRP1, ADH1, or ADH2 gene.

The expression plasmid can also take the form of shuttle vectors between a bacterial host such as *E. coli*, DH5a from GIBCO/Life Science and yeast; the antibiotic Zeocin are used to be a marker for HSA carrier vector in all the examples.

The expression vector contains the polynucleotide of HSA or HSA fusion therapeutic protein are introduced into yeast according to the protocols described in the kit from Invitrogen Inc. After selection of transformed yeast colonies, those cells expressing the HSA fusion protein of interest are inoculated into appropriate selective medium and then tested for their capacity to secrete the given fusion protein into the extracellular medium. The harvesting of the protein can be conducted during cell growth for continuous cultures, or at the end of the growth phase for batch cultures. The fusion proteins which are the subject of this invention are then further purified from the culture supernatant by methods which take into account the albumin purification methods and pharmacological activities.

It is noted that other expression systems may also be used to express rHSA and HSA/CPSF fusion proteins, including but not limited to *E. coli, B. Subtitis, Saccharomyces, Kluyverornyces, Candida, Torulopsis, Torulaspora, Schizosaccharomyces, Citeromyces, Pachysolen, Debaromyces, Metschunikowia, Rhodosporidium, Leucosporidium, Botryoascus, Sporidiobolus, Endomycopsis*, animals, plants, and insect cells.

3. Combination Therapy of HSA/CPSF Fusion Proteins

The present invention also provides combinations of different HSA/CPSF fusion proteins. The specific combinations of these fusion proteins may be administered to a patient to stimulate proliferation of multiple types of cells in the body or to synergistically enhance proliferation of a particular cell type. In particular, a combination of human albumin fusions with different hematopoietically active cytokines is used to effectively promoting proliferation of the multiple blood cells and platelets. By using a combination of HSA/CPSF fusion proteins targeting the signal transduction pathways of different types of blood cells, multiple blood functional cell production, such as platelets, erythrocytes and macrophages of white cells, can be increased after administration by just one injection.

In the present invention, the albumin's plasma transporter function and the therapeutic function of the CPSF are integrated into a fusion form. The presence of albumin may confer a superior stability to the CPSF by resisting degradation by proteases in the blood circulation, thus significantly prolonging the plasma half life of the CPSF. Due to the masking effect of a bulky albumin, a combination of different CPSFs fused with albumin may impose less interference with the biological function(s) among different albumin fused CPSFs than among a combination of the "naked" CPSFs. Further, a CPSF fused with albumin may be slowly released in the system over an extensive period of time, thereby reducing the toxicity associated with injection of the CPSF alone in abnormally high concentrations in the body. Such a slow release mode of action of the fusion protein combination can significantly reduce the amount and/or frequency of injections of the CPSF, thereby further reducing the side effects of CPSFs. Such combinations are particularly useful for stimulating multiple blood cell proliferation after or before the chemo- or radiation therapy of cancer patients whose tolerance for frequent, high dose injection of CPSF are seriously compromised.

For example, in animal testing human TPO, stem cell factor (SCF) and IL-3 have shown very strong toxicities in vivo. Due to the severe toxicity in vivo, SCF has been approved by the FDA for use in vitro only. The limitation on SCF has prevented it from being developed into useful therapeutics in the clinic. The side effects of IL-3 are dose-dependent. At a dose higher than 5 µg/Kg, side effects have been observed in patients treated with IL-3, including fever, rash, fatigue, diarrhea, rigor, musculoskeletal pain, chills, headache, conjunctivitis, edema, chest pain, dyspnea, decrease in platelet counts, increasing in basophilic counts, marrow fibrosis, and pulmonary edema. Eder, M et al. (1997) "IL-3 in the Clinic", Stem Cells, 15:327-333.

According to the present invention, HSA fusion protein with this type of CPSF may remove above limitations by slowly releasing the drug into the patient's system. In addition, such fusion proteins may be combined with a relatively higher amount of albumin to further reduce the impact resulted from directly injecting the drug into the blood which causes a strong, adverse reaction of the central nervous system.

It is also known that "naked" cytokines (i.e., cytokines not fused to another protein such as HSA) are quite unstable when stored and have a short plasma half-life. Clearly, a therapeutic protein with such a weak stability in vivo constitutes a major handicap. In effect, repeated injections of the product, which are costly and inconvenient for patient, or an administration of product by perfusion, become necessary to attain an efficient concentration in plasma. Due to its extended plasma half-life and enhanced stability, the HSA/CPSF fusion proteins of the present invention and their combinations, e.g., HSA fusions with hIL-11, hEPO, hG-CSF and hGM-CSF, can be used to stimulate the production of multiple blood cells in plasma of humans.

In one embodiment, HSA/IL-11 fusion may be combined with HSA/EPO fusion and the resulting combination may be administered to a patient with a hematological disorder to simultaneously stimulate proliferation of erythrocytes and platelets. For example, cancer patients may be injected with a combination of HSA/IL-11 and HSA/EPO fusion proteins, before or after, chemotherapy treatment to avoid blood transfusion and to stimulate proliferation of erythrocytes and platelets.

In another embodiment, HSA/IL-3 fusion may be combined with HSA/EPO fusion and the resulting combination may be administered to a patient with a hematological disorder to enhance EPO-induced production of erythrocytes.

In yet another embodiment, HSA/IL-3 fusion may be combined with HSA/GCSF fusion and the resulting combination may be administered to a patient with a hematological disorder to increase the production of erythrocytes and neutrophiles, as well as eosinophils.

Alternatively, an HSA/CPSF fusion may be co-administered with a different HSA/CPSF fusion simultaneously or sequentially to a patient in need thereof. This combination therapy may confer synergistic therapeutic effects on the patients. In one embodiment, the method is provided, comprising: administering a first pharmaceutical formulation comprising a first fusion protein of HSA and a first CPSF to the patient in a therapeutically effective amount; and administering to the patient a second pharmaceutical formulation comprising a second fusion protein of HSA and a second CPSF to the patient in a therapeutically effective amount. Such a combination therapy may confer synergistic therapeutic effects on the patient.

For example, HSA-IL-11 fusion protein may be administered to the patient first, followed by administration of HSA-EPO, HSA-GCSF and/or HSA-GMCSF at therapeutically effective doses and ratios to stimulate proliferation of different types of blood cells.

The present invention further provides a kit for use in the combination therapy described above. The kit comprises: a first fusion protein of HSA and a first CPSF, and a second fusion protein of HSA and a second CPSF. The first and second CPSFs may be the same or different. For example, the first CPSF is IL-11 and the second CPSF is EPO; the first CPSF is IL-3 and the second CPSF is EPO; or the first CPSF is IL-11 and the second CPSF is GCSF.

The HSA/CPSF fusion proteins and their combinations thereof may be used to treat a wide variety of diseases, including but not limited to the hematological disorders such as hypochromia, hypochromic microcytic anemia, and anemia, platelet-less, HIV infection, cancer, renal failure, and tissue/organ transplantation. These fusion proteins are preferred not to contain non-human sequences that may elicit adverse immunogenicity in the patient.

EXAMPLES

1. General Molecular Cloning Techniques

The classic methods of molecular cloning including, DNA preparative extractions, agarose and polyacrylamide electrophoresis, plasmid DNA purification by column or from gel, DNA fragment ligations, and restriction digestion, are described in detail in Maniatis T. et al., "Molecular cloning, a Laboratory Manual", Cold Spring Harbor laboratory, Cold Spring Harbor, N.Y., 1982 and will not be reiterated here.

Polymerase Chain Reaction (PCR) used through out all the examples is described by Saiki, R. K. et al, Science 230:1350-1354, 1985 and is carried out on a DNA thermal cycler (Perkin Elmer) according to the manufacturer's specification. DNA sequencing was performed by using standard facilities and following the method developed by Sanger et al., Proc. Natl. Acad. Sci. USA, 74:5463-5467, 1977. Oligonucleotides were synthesized by commercial facilities.

Transformation of E. coli was done by using DH5α competent cells from GIBCO/BRL. Qiagen plasmid DNA purification columns were used in the purification of plasmid DNAs. The transformation of yeast was carried out by electroporation following the instruction provided by the manufacturer or according to the manual of EasySelect™ Pichia Expression Kit (Invitrogen Inc). All yeast stains used in the examples are members of the family of Pichia, and in particular, the strain of Pichia pastoris (supplied by Invitrogen).

2. Construction of a Backbone Vector Expressing Human Serum Albumin

A total RNA isolated from human fetal liver was used in a reverse transcription polymerase chain reaction (RT-PCR) to generate the polynucleotide encoding human serum albumin. Briefly, 5 µg of RNA was reverse transcribed by adding a poly(T)$_{18+N}$ primer and the SuperScript™ RNase H⁻ reverse transcriptase (GIBCO/BRL) to make the complementary first strand of cDNA. The reaction was incubated at 45° C. for 20 minutes, then at 55° C. for 40 minutes.

The primers for cloning human serum albumin (HSA) are the following:

```
SEQ ID No. 23:
5'-GAATTCATGAAGTGGGTAACCTTTATTTCC-3'
and

SEQ ID No. 24:
5'-GAATTCTTATAAGCCTAAGGCAGCTTGACTTGC-3'.
```

These primers were designed based on the HSA sequence published by GenBank (Access# V00494). Two EcoR I (underline of primers) sites were created at the 5' end and 3' end for sub-cloning into an expression vector. After inactivating the reverse transcriptase at 94° C. for 4 minutes, the DNA encoding of HSA was further amplified by Taq DNA PCR (Perkin Elmer) with 35 cycles of 94° C./30 seconds and 58° C./30 seconds and 72° C./2 minutes 30 second, followed by a 72° C./10 minutes incubation. The PCR product (1842 base pairs) was confirmed by 1% agarose gel electrophoresis. The product was subcloned into a pCR II TA cloning vector from Invitrogen. DNA sequencing confirmed that the plasmid DNA contained an insert whose polynucleotide sequence matches the DNA sequence published in GenBank (Access# V00494). FIG. 1, Seq ID No.11 is a polynucleotide DNA sequence and Seq ID No 12 is the protein amino acid sequence of human serum albumin.

After restriction digestion of the PCR product with EcoR I, the gel purified HSA DNA fragment was inserted into a pPICZ-A vector (provided by Invitrogen) at the EcoR I site. After transformation of bacteria DH5α cells with this vector encoding HSA, a colony was selected from a low salt LB-agar plate contains 25 µg/ml Zeocin. The direction of the insert was confirmed by restriction enzyme double digestion of plasmid DNA by Xho I/Nde I. The construct was designated as pYZ-HSA (Y: yeast vector; Z: Zeocin resistant) and its physical map is shown in FIG. 2.

There are some advantages associated with the vector constructed above. It confers resistance to the antibiotic Zeocin. Zeocin is isolated from Streptomyces and is structurally related to bleomycin/phleomycin-type antibiotics. Antibiotics in the family of bleomycin/phleomycin are broad spectrum antibiotics that act as strong antibacterial and anti-tumor drugs. They show strong toxicity against bacteria, fungi (including yeast), plants, and mammalian cells. However, Zeocin is not as toxic as bleomycin on fungi. A single antibiotic Zeocin could be used in selecting the recombinants in both bacteria and in yeast. Further, there are multiple cloning sites at the 3' end of HSA for conveniently subcloning a CPSF protein in frame to encode a HSA-CPSF. In addition, a myc epitope sequence and a polyhistidine tag can be fused to the C-terminal of the expressed fusion protein for easy detection and/or purification by using commercially available antibodies against myc or polyhistidine tags. This vector, as a backbone vector, was used in the construction of expression vectors for all the HSA fusion proteins described in the Example section.

3. Molecular Cloning of Human IL-11, EPO, G-CSF, and GM-CSF 3.1. Molecular Cloning of Human IL-11 Gene Human Il-11 was cloned from a total RNA preparation of human bone marrow-derived stromal cells by RT-PCR method described in Example 2. The oligonucleotide primers are

```
SEQ ID NO. 25:
5'-CATATGAACTGTGTTTGCCGCCTGGTCC-3'

SEQ ID NO. 26:
5'-GATATGTATGACACATTTAATTCCC-3'
```

A polynucleotide having 1051 base pairs (bp) was amplified from RT-PCR reaction and subcloned into pCR II TA cloning vector from Invitrogen Inc. DNA sequencing confirmed the reading frame of human IL-11 and inclusion of a 448 bp 3'-end un-translation region of hIL-11. An Nde I restriction enzyme site was created at the 5' end. The ATG initiate start codon of hIL-11 was included in this site (underlined in SEQ ID NO. 25). The DNA sequence of hIL-11 (SEQ ID NO. 13) and its amino acid sequence (SEQ ID NO. 14) are shown in FIG. 1.

3.2. Molecular Cloning of Human Erythropoietin Gene

Human erythropoietin gene was obtained by RT-PCR from human fetal kidney mRNA from Clontech Laboratory. EPO specific primers were designed based on the sequence published by Lin, F K et al., "Cloning and expression of human erythropoietin gene", Proc. Natl. Acad. Sci. USA., 82(22): 7580-7584 (1985). They are

```
SEQ ID NO. 27:
5'-GGATCCATGGGGGTGCACGAATGTCC-3',
and

SEQ ID NO. 28:
5'-GAATTCTCATCTGTCCCCTGTCCTGC-3'.
```

The PCR product was a full length reading frame of EPO with two newly created restriction enzymes in each end, Bam HI at the 5'end and EcoR I at 3'end. The product was inserted into pCR II vector and sequence confirmed. The human EPO DNA sequence (SEQ ID NO. 15) and amino acid sequence (SEQ ID NO. 16) are showed in FIG. 1.

3.3. Molecular Cloning of Human G-CSF

Primers used to clone the human G-CSF gene from a cDNA library of human fetal liver tissues are

```
SEQ ID NO. 29:
5'-GGATCCATGGCTGGACCTGCCACCC-3',
and

SEQ ID NO. 30:
5'-GAATTCTCAGGGCTGGGCAAGGTGGC-3'
```

These primers were designed based on Nagata, S et al., Molecular Cloning and Expression of cDNA for Human Granulocyte Colony-Stimulating Factor, Nature, 319:415-418, 1986. A Bam HI site at 5'end and an EcoR I site at 3'end of G-CSF were created. The PCR products were gel-purified and subcloned into pCR2.1 TA cloning vectors and DNA sequence was confirmed. The human G-CSF DNA sequence (SEQ ID NO. 17) and the amino acid sequence (SEQ ID NO. 18) are shown in FIG. 1.

3.4. Molecular Cloning of Human GM-CSF

Human GM-CSF was cloned from a total RNA sample prepared from human fetal liver based on Wong, G G et al., "Human GM-CSF: molecular cloning of the complementary DNA and purification of the nature and recombinant proteins" Science, 228:810-815, 1985. The Primers were:

```
SEQ ID NO. 31:
5'-GGATCCATGTGGCTGCAGAGCCTGCTGC-3',
and

SEQ ID NO. 32:
5'-GAATTCTCACTCCTGGACTGGCTCC-3'
```

The PCR products were gel-purified and inserted into pCR2.1 TA cloning vector and sequence confirmed. The human GM-CSF DNA sequence (SEQ ID NO. 19) and amino acid sequence (SEQ ID NO. 20) are shown in FIG. 1.

4. In Frame Fusion of HSA With Human IL-11, EPO, G-CSF or GM-CSF

There is a Bsu36 I site at the C'-terminus of HSA. All of the CPSFs described in the Example section were fused into this site by PCR primer extension to generate a restriction enzyme site of Bsu36 I at the N-terminus of the CPSF DNA sequence. The CPSF DNA fragments were amplified by PCR and then subcloned into Bsu36 I and Xho I sites of pYZ-HSA vector which had been double digested with Bsu36 I and Xho I to linearize the plasmid DNA 4.1. Construction of Vector Containing Hybrid Polynucleotide of HSA/hIL-11

IL-11 gene was fused to HSA C'-terminus by using the following PCR primers:

```
SEQ ID NO. 33:
5'-CTGCCTTAGGCTTACCTGGGCCACCACCTGGCC-3'.

(Human IL-11 mature protein sequence is
underlined), and

SEQ ID NO. 34: 5'-TGTCGACTCACAGCCGAGTCTTCAGCAGC-3'.
```

A Sal I site (underlined in SEQ ID NO. 34) was created at the 3' end of hIL-11 gene because there is a Xho I site in the sequence of mature protein of IL-11. The Sal I site sequence is a cohesive sequence with Xho I site. After ligation, the Sal I and Xho I site were all gone.

The PCR products were digested with Bsu36I and Sal I, and the fragment was gel purified and inserted into pYZ-HSA between of Bsu36 I and Xho I sites to generate a new plasmid DNA, pYZ-HSA/hIL-11. The HSA-hIL-11 hybrid polynucleotide sequence (SEQ ID NO. 1) and its fusion protein amino acid sequence (SEQ ID NO. 2) are showed in FIG. 1.

4.2. Construction of Vector Containing Hybrid Polynucleotide of HSA/EPO

To make a HSA-EPO fusion protein, the following primers were designed

```
SEQ ID NO. 35:
5'-CTGCCTTAGGCTTAATCTGTGACAGCCGAGTCC-3'

(human EPO mature protein sequence underlined), and

SEQ ID NO. 36: 5'-CACTCGAGTCATCTGTCCCCTGTCCTGC-3'

(Xho I site underlined)
``` and used to generate the modified human IL-11 DNA fragment. The PCR products were inserted between Bsu36I and Xho I sites of pYZ-HSA to generate a pYZ-HSA/hEPO. The HSA-EPO hybrid polynucleotide sequence (SEQ ID NO. 5) and its fusion protein amino acid sequence (SEQ ID NO. 6) are shown in FIG. 1.

4.3. Construction of Vector Containing Hybrid Polynucleotide of HSA/HG-CSF

Human G-CSF gene was fused with HSA DNA sequence by using two primers:

```
SEQ ID NO. 37:
5'-CTGCCTTAGGCTTAACCCCCCTGGGCCCTGCCAGC-3'

(G-CSF mature protein sequence underlined), and

SEQ ID NO. 38: 5'-CTCGAGTCAGGGCTGGGCAAGGTGG-3'

(Xho I site at the 3'-teminus of G-CSF underlined).
```

The PCR products were gel purified and subcloned between Bsu36I and Xho I sites of pYZ-HSA to generate a pYZ-HSA/hG-CSF. The HSA-G-CSF hybrid polynucleotide sequence (SEQ ID NO. 7) and its amino acid sequence (SEQ ID NO. 8) are shown in FIG. 1.

4.4. Construction of Vector Containing Hybrid Polynucleotide of HSA/HGM-CSF

The following primers:

```
SEQ ID NO. 39:
5'-ACTCCTTAGGCTTAGCACCCGCCCGCTCGCCCAGC-3'

(GM-CSF mature protein sequence underlined), and

SEQ ID NO. 40: 5'-CTCGAGTCACTCCTGGACTGGCTCC-3'

(Xho I site underlined)
``` were used to modify GM-CSF DNA sequence in order to subclone it into pYZ-HSA vector. PCR products were gel purified and double digested with Bsu36 I and Xho I and inserted between Bsu36 I and XhoI sites of pYZ-HSA to generate a pYZ-HSA/hGMCSF. The HSA/GM-CSF hybrid polynucleotide sequence (SEQ ID NO. 9) and its fusion protein amino acid sequence (SEQ ID NO. 10) are shown in FIG. 1.

5. Transformation of Yeasts

A yeast *Pichia pastoris* strain, GS115, colony was inoculated into 5 ml of YPD medium in a 50 ml conical tube at 30° C. overnight with shaking at 250 rpm. 0.2 ml of the culture was inoculated into 500 ml of YPD medium continually shaking at 30° C. for further 2-3 hours or until the cell density reach to $OD_{600}$=1.3-1.5. The cells were collected by centrifuging. The cell pellet resuspend in 500 ml of ice-cold sterile water in order to wash the cells. After two rounds water washing, the cells were resuspended in 20 ml of ice-cold 1 M sorbitol to wash again. The cells finally suspended in 1 ml of ice-cold 1M sorbitol. The plasmid DNA constructs from Example 2, pYZ-HSA and in Example 4, pYZ-HSA/IL-11, pYZ-HSA/hEPO, pYZ_HSA/hG-CSF, and pYZ-HSA/hGM-CSF was linearized by PmeI restriction enzyme digestion first.

Five μg of each linear plasmid DNA was used to transform 80 μl of the freshly made yeast cells in an ice-cold 0.2 cm electroporation cuvette. The cells mixed with plasmid DNA were pulsed for 5-10 ms with field strength of 7500 V/cm. After the pulse, 1 ml of ice-cold 1M sorbitol was immediately added into the cuvette and the content was transferred to a sterile 15 ml tube. The transformed cells were incubated in 30° C. without shaking for 2 hours then spread on pre-made YPD-agar plates with 100 μg/ml Zeocin. The colonies were identified with the insert and the expression level was determined by SDS-PAGE or western-blot with proper antibodies.

A consortium of 4 yeast strains produced above (collected referred to as YZ-HSA/CPSFs) of *Pichia pastoris* encoding HSA/IL-11, HSA/hEPO, HSA/hG-CSF, and HSA/hGM-CSF was deposited to the ATCC® (America Type Culture Collection) under the Budapest Treaty on the International Recognition of the Deposit of Microorganisms for the Purposes of Patent Procedure. The 4 yeast strains are separately designated as YZ-HSA/IL-11, YZ-HSA/hEPO, YZ-HSA/hG-CSF, and YZ-HSA/hGM-CSF, respectively, and their consortium is deposited at the ATCC® under Patent Deposit Designation No: PTA-4607.

Different strains of *Pichia*, such as X-33, KM71 and proteinase deficient strains SMD1168 and ZY101 were tested for the expression and secretory of recombinant proteins.

6. Secretion and Characterization of HSA-CPSF Fusion Proteins Expressed by *Pichia*

Several colonies from each transformation of the HSA-CPSF were cultured with Zeocin in the buffered minimal medium with glycerol overnight or until $OD_{600}$=2-6 at 30° C. and shaking at 300 rpm. The cultured cells were collected by centrifuge at 1500 rpm for 5 minutes. Resuspend the cells into buffered minimal medium without glycerol and cell densities was keep in $OD_{600}$=1.0. 100% methanol was added into each flask to a final concentration at 0.5% every 24 hours to induce the protein expression. The culture medium was collected at different time points and the expression of each fusion protein was confirmed by SDS-PAGE and western blot. The results showed that human albumin and HSA-CPSF fusion protein were expressed and secreted into the medium.

Figure 3:
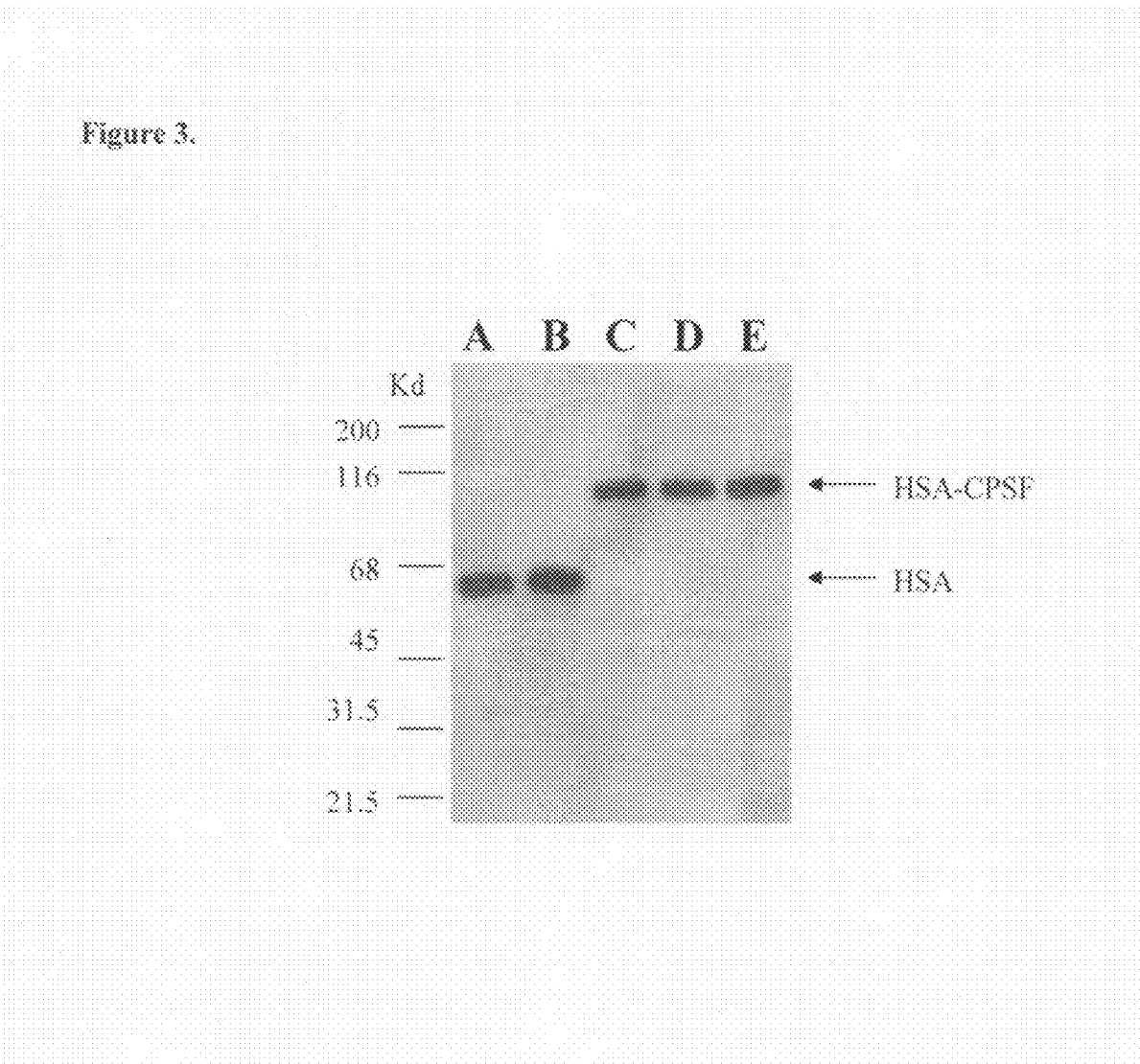
FIG. 3 shows a Western blot detected using mouse monoclonal anti-human serum albumin (Sigma Cat# A6684). Each lane was load with equivalent of 100 ng of proteins. A), HSA (65 Kd) from blood plasma; B), HSA (65 Kd) from yeast; C), HSA/hG-CSF (84.2 Kd); D), HSA/hEPO(83.5 Kd); E), HSA/hIL-11(84.5 Kd).
Figure 4:
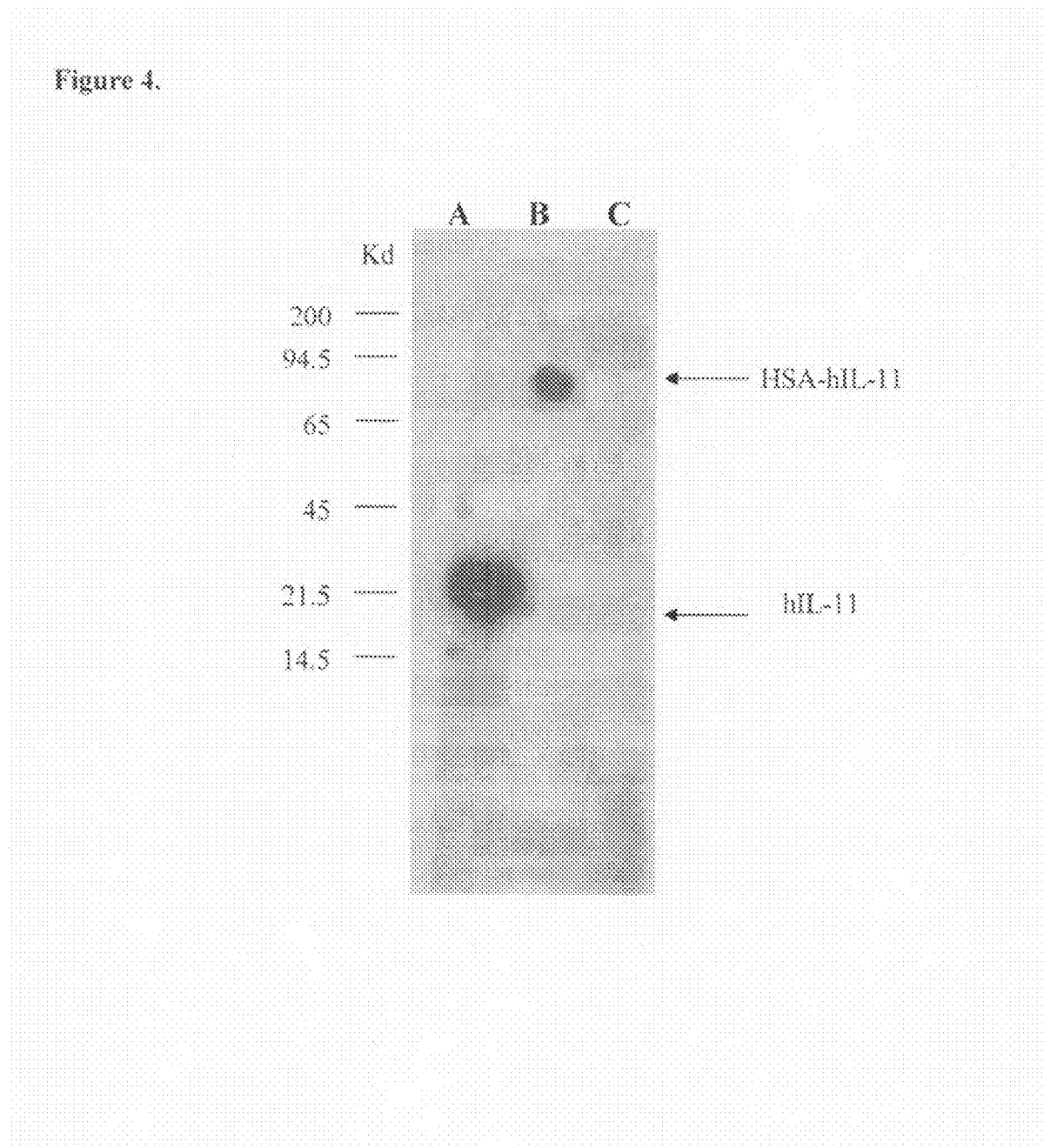
FIG. 4 shows a Western blot detected using goat polyclonal anti-hIL-11 antibody (R&D Systems, Cat# Ab-218-NA), each lane contains 100 ng proteins. A), human IL-11 expressed by *E. coli*; B), HSA/hIL-11 fusion protein expressed by yeast.

Mouse monoclonal anti-human serum albumin (Sigma) was used for immunoblotting on a SDS-PAGE gel. A typical Western blot experiment was carried on by electrophoresis transfer the protein from SDS-PAG to a nylon or nitrocellulose filter and incubated with a specific antibody (as the "first antibody"). Then an anti-first antibody was added to bind to the first antibody (as the "second antibody"). The second antibody was labeled with Fluorescence and the filter was exposed to an X-ray film. Protein molecular weight standard was used to determine the protein size. The results (FIG. 3) showed that the expressed recombinant proteins, HSA, HSA-CPSF therapeutic fusion protein, had an expected molecular weight and also had the same antigen as that of HSA prepared from a human blood plasma (Sigma). Using monoclonal anti-hIL-11 specific antibody as the first antibody, the HSA/hIL-11 fusion protein and human IL-11 (R&D System) had the same antigen and showed that the molar ratio of HSA to hIL-11 in the HSA/hIL-11 fusion protein is as expected (FIG.

Figure 5:
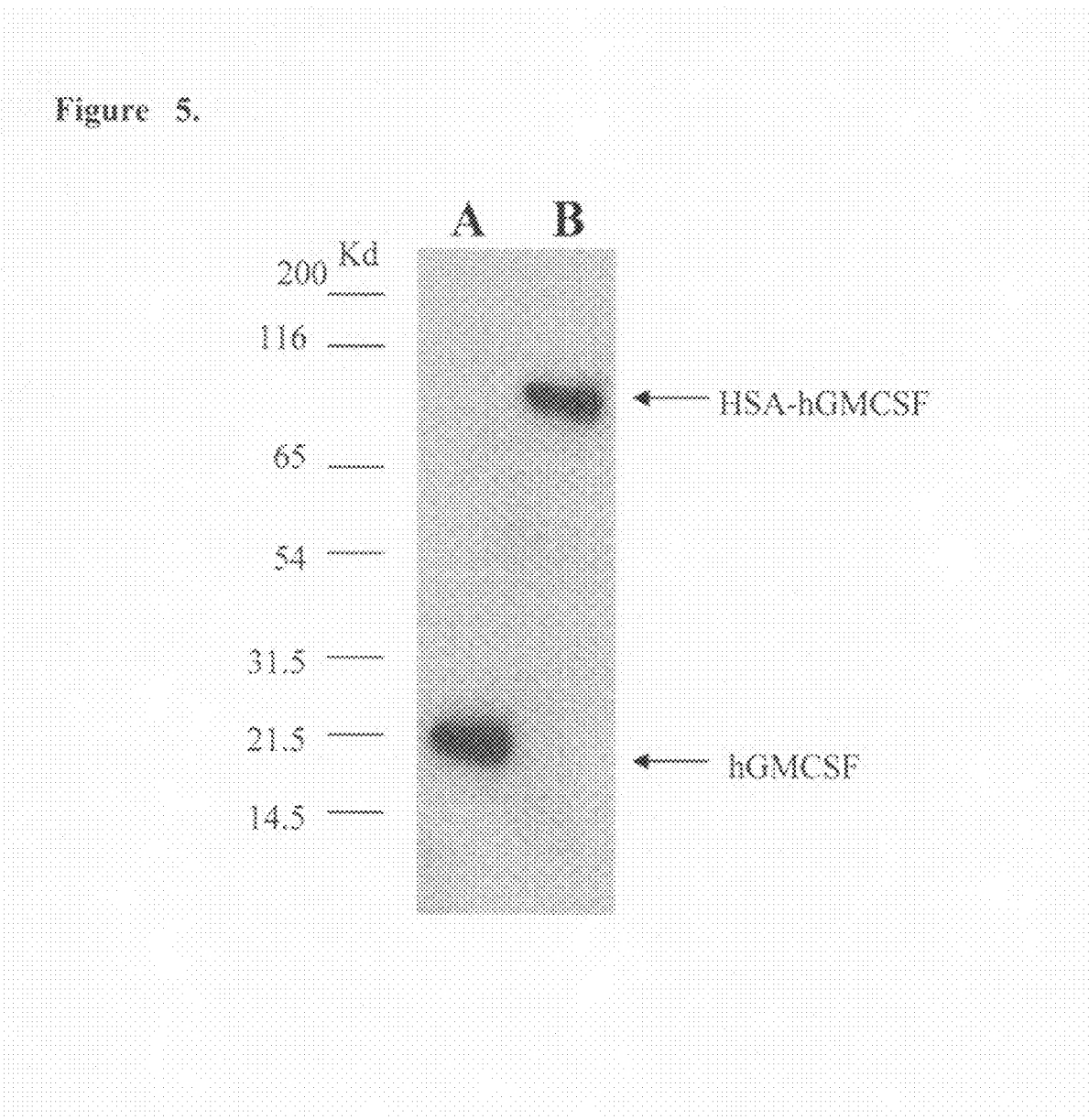
FIG. 5 shows a Western blot detected using monoclonal anti-hGMCSF antibody (R&D Systems), each lane contains 20 ng proteins. A), Human GMCSF expressed by *E. coli*; B), HSA/hGMCSF fusion protein expressed in yeast.

4). Using monoclonal anti-hGMCSF specific antibody (R&D System) as the first antibody, the HSA-GMCSF fusion protein and human GMCSF (R&D System) had the same antigen and showed that the molar ratio of HSA to GMCSF in the HSA/GMCSF fusion protein is as expected (FIG. 5).

7. Purification and Molecular Characterization of HSA-CPSF

The cell culture medium (supernatant) containing the secreted protein of HSA or HSA-CPSF fusion protein produced from the recombinant *Pichia* was collected, the salt concentration reduced, and the pH was adjusted to above 7.5. The concentrated sample was passed through an Affi-Gel Blue-gel (50-100 mesh) (Bio-Rad). The albumin or albumin fusion protein was bound to the matrix and eluded by a gradient 1-5M NaCl. 75-85% pure albumin or albumin-CPSF can be recovered in this step. If further purification is necessary, a size exclusion chromatography is applied to give a 95-99% purity of proteins. The pyrogen was removed from the protein samples in order to meet the requirement for use in in vivo test. The Affi-Prep Polymyxin Support (BIO-Rad) column was used to remove endotoxin from the samples. The purified protein finally passed through 0.2 µM filter to be sterilized and the protein concentration was measured by a standard method by using a Bio-Rad Protein Assay Kit.

8. Cell Proliferation Assay of Human IL-11

A murine plasmacytoma cell line T1165 which is an IL-6 depended cell line was used to carry out a bioassay for IL-11 according to Paul, S R et al., PNAS 87:7512-7516, 1990. The cells were maintained in RPMI medium supplemented with 10% heat-inactivated fetal calf serum, 2 mM glutamine, penicillin (100 U/ml) and streptomycin (100 µg/ml) (Gibco/BRL), 50 µM 2-meracaptoethanol (sigma), and recombinant human IL-6 (4-10 ng/ml or 20 U/ml in final concentration) (Gibco/BRL). Bioassay is preformed by $1\times10^4$ cells/well were placed into 96-well tissue culture plate in 200 ul of IL-6 free medium for 48 hr in 37° C. in the presence of multiple dilution of hIL-11 purified from Thioredoxin fusion protein in *E. coli* or from yeast purified HSA/IL-11 fusion protein. In the final 6 hours, the cells were pulse-labeled with 0.5 mCi of [$^3$H]thymidine (1 Ci=37 GBq, from Dupont) per well. After incubation, the cells were collected on to a glass filter, washed and assayed on a Beckman scintillation counter, Neutralizing goat anti-human IL-6 antibody was included to abrogate the effect of IL-6 as control in the testing of purified protein samples. The control proteins including with or without HSA (from human blood preparation), rHSA expressed in yeast (*Pichia*) in the lab, Thioredoxin (Trx) was a peptide purified from the enterokinase digested Trx/IL-11 fusion protein. The results are shown in FIG. 6 (A and B panels). The HSA/hIL-11 bioactivities were not affected by the presence of antibody of human IL-6. HSA fusion protein has about ⅓ of cell proliferation activity compared with that human IL-11 alone in the same amount of protein. Since HSA has a molecular weight about 3 times higher than that of hIL-11, it can be inferred that HSA-hIL-11 fusion protein has the same bioactivity as that of human IL-11 alone.

9. Bioassay of EPO by ELISA

Enzyme-linked immunosorbent assay (ELISA) kit from R&D Systems was used for the quantitative determination of erythropoietin (EPO) concentration and bioactivities comparison with a commercial EPO sample. The EPO ELISA is based on the double-antibody sandwich method. Microplate wells, precoated with monoclonal (murine) antibody specific for human EPO were incubated with samples or standard. Erythropoietin binds to the immobilized antibody on the plate. After removing excess protein sample or standard, wells were incubated with an anti-EPO polyclonal (rabbit) antibody conjugated to horseradish peroxidase. During the second incubation, the antibody-enzyme conjugate bound to the immobilized EPO. Excess conjugate was removed by washing. A chromogen was added into the wells and oxidized by the enzyme reaction to form a blue colored complex.

The reaction was stopped by the addition of acid, which turned the blue to yellow. The amount of color generated was directly proportional to the amount of conjugate bound to the EPO antibody complex, which, in turn, was directly proportional to the amount of EPO in the protein samples or standard. The absorbance of this complex was measured and a standard curve was generated by plotting absorbance versus the concentration of the EPO standards. The EPO concentration of the unknown sample was determined by comparing the optical density of the protein samples to the standard curve. The standards used in this assay were recombinant human EPO (with kit) calibrated against the Second International Reference Preparation (67/343), a urine-derived form of human erythropoietin. Human recombinant EPO expressed in CHO cells was used as a control to determine the rHSA/EPO bioassay sensitivity.

Figure 7:
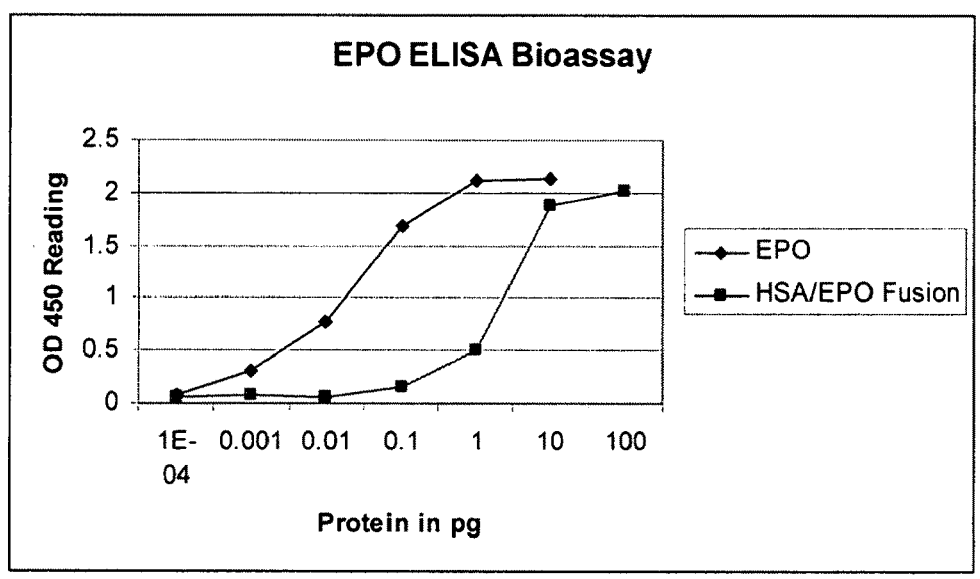
FIG. 7 is an ELISA bioassay for EPO and HSA fusion protein, HSA/hEPO.

The results showed that in the bioassay hEPO fused to HSA had 1/10 of the sensitivity compared with the standard (FIG. 7). The size of HSA-EPO fusion protein molecule may be too large, which prevents the anti-EPO antibody from efficiently binding to the EPO molecule fused to HSA, thereby reducing the sensitivity of the detection in this bioassay.

10. Stability Testing of HSA-CPSF Fusion Proteins In Vitro

Using HSA/hIL-11 as an example, the stability of this HSA-CPSF fusion protein was tested at different time points at 37° C. and 50° C. 5 ng of human IL-11 from bacteria or 5 ng of rHSA/hIL-11 was put into 200 µl thin-well PCR tube with 200 µl of tissue culture medium RPM1 without fetal bovine serum and other components. The tubes were sealed and left in water bath. Samples were taken out at different time points and immediately put into −80° C. for storage. After all of samples were collected, a cell proliferation test on T1165 cell line was carried out by incorporating $^3$H-Thymidine into newly synthesized DNA of proliferating cells. The control of the test was set up in the same way as that in the bioassay of human IL-11 (See Paul et al., 1990). As shown in FIG. 8, after 5 weeks in 37° C. (Panel A), the bioactivity of HSA/ IL-11 still remained the same, but the "naked" human IL-11 lost almost all of its bioactivity after three weeks at 37° C. At 50° C. (Panel B), the "naked" human IL-11 lost its the bioactivity completely in 2 weeks. And the HSA/IL-11 fusion protein still retained at least half of its bioactivity. These results indicate that a CPSF fused to human albumin can have a longer storage time and more resistant to degradation in harsh environment such as high temperatures.

11. Synergistic Effects of Combination of HSA-CPSF Fusion Proteins in Stimulation of Multicell Proliferation Rabbits (2.3-2.6 Kg) were injected with 200 µl of recombinant proteins prepared above at day 1, day 3 and day 6. Rabbit A was injected with a mixture of 150 U/kg EPO (about 10 µg of protein) and 100 µg recombinant HSA (rHSA); Rabbit B with a mixture of 120 µg IL-11 and 100 µg rHSA; and Rabbit C with a mixture of 120 µg rHSA/hIL-11 fusion (equivalent of 50 µg of pure bacteria-expressed IL-11), 27 µg rHSA/hEPO fusion (equivalent of 150 U of HSA-EPO determined by using the EPO-ELISA Kit, R&D System Inc.) and 50 µg rHSA. Rabbit D was injected with 120 µg of HSA-IL-11 and about 80 µg rHSA.

Blood samples were collected and red blood cell and platelet numbers were counted by a hemacytometer. The results are shown in FIG. 9 (panels A, B, and C). The cell counts on the starting day of the experiment was treated as the base line. After the treatment with the proteins, the cell counts were compared with those on the starting day and the changes were plotted in the graphs in FIG. 9.

As shown in panel A of FIG. 9, both EPO and HSA/EPO fusion protein stimulated the production of erythrocytes in rabbit A and C, respectively. However, in rabbit A injected with the naked EPO, the level of erythrocytes reached a peak around day 35 post first injection and then declined quickly to reach near a baseline level around day 55. In contrast, in rabbit C injected with HSA/EPO fusion protein, the level of erythrocytes increased and reached a plateau around day 35 post first injection but remained high till the end of the experiment. These results demonstrated that HSA/EPO fusion protein has a much longer plasma half-life than the naked EPO and remains bioactive for a much longer time than the naked EPO in vivo. As also shown in this panel, IL-11 had little effect in stimulation of erythrocyte production in rabbit B.

As shown in panel B of FIG. 9, both IL-11 and HSA/IL-11 fusion protein stimulated the production of platelets in rabbit B and C, respectively. However, in rabbit B injected with the naked IL-11, the level of platelets reached a peak around day 20 post first injection and then declined quickly to reach near a baseline level around day 43. In contrast, in rabbit C injected with HSA/IL11 fusion protein, the level of platelets increased and reached a plateau around day 40 post first injection but remained high till the end of the experiment. These results demonstrated that HSA/IL-11 fusion protein has a much longer plasma half-life than the naked IL-11 and remains bioactive for a much longer time than the naked IL-11 in vivo. As also shown in this panel, EPO had little effect in stimulation of platelet production in rabbit A.

Panel C in FIG. 9 compares the effects of a combination of HSA/EPO and HSA/IL-11 with HSA/EPO and HSA/IL-11 individually in stimulation of the production of erythrocytes and platelets on day 35 post first injection. As shown in this panel, compared with individual HSA/EPO and HSA/IL-11, a combination of HSA/EPO and HSA/IL-11 had much stronger effects in stimulating the production of both erythrocytes and platelets. For example, the erythrocyte level in the rabbit C which was injected with 27 μg of HSA/EPO in combination 120 μg HSA/IL-11 with is higher than the total erythrocyte level combining that in rabbit A (injected with 10 μg HSA/EPO) and rabbit D (120 μg HSA/IL-11). Since the molar ratio of HSA to EPO in the HSA/EPO fusion is about 5:1 and the amount of HSA/EPO in rabbit C is only 2.7 folds of that in Rabbit A, it can be predicted that if the amount of HSA/EPO is increased 5 folds so that a equal mole of HSA/EPO in both the HSA/EPO+HSA/IL-11 combination and HSA/EPO alone is administered, the erythrocyte level in the animal should be even higher with the administration of the combination. Based on this analysis, it can be reasonably inferred that a combination of HSA/EPO+HSA/IL-11 fusion proteins has a synergistic effect in stimulating multiple blood cell production.

12. Expression and Scale-Up of HSA-CPSF Fusion Protein by Fermentation

Figure 10:
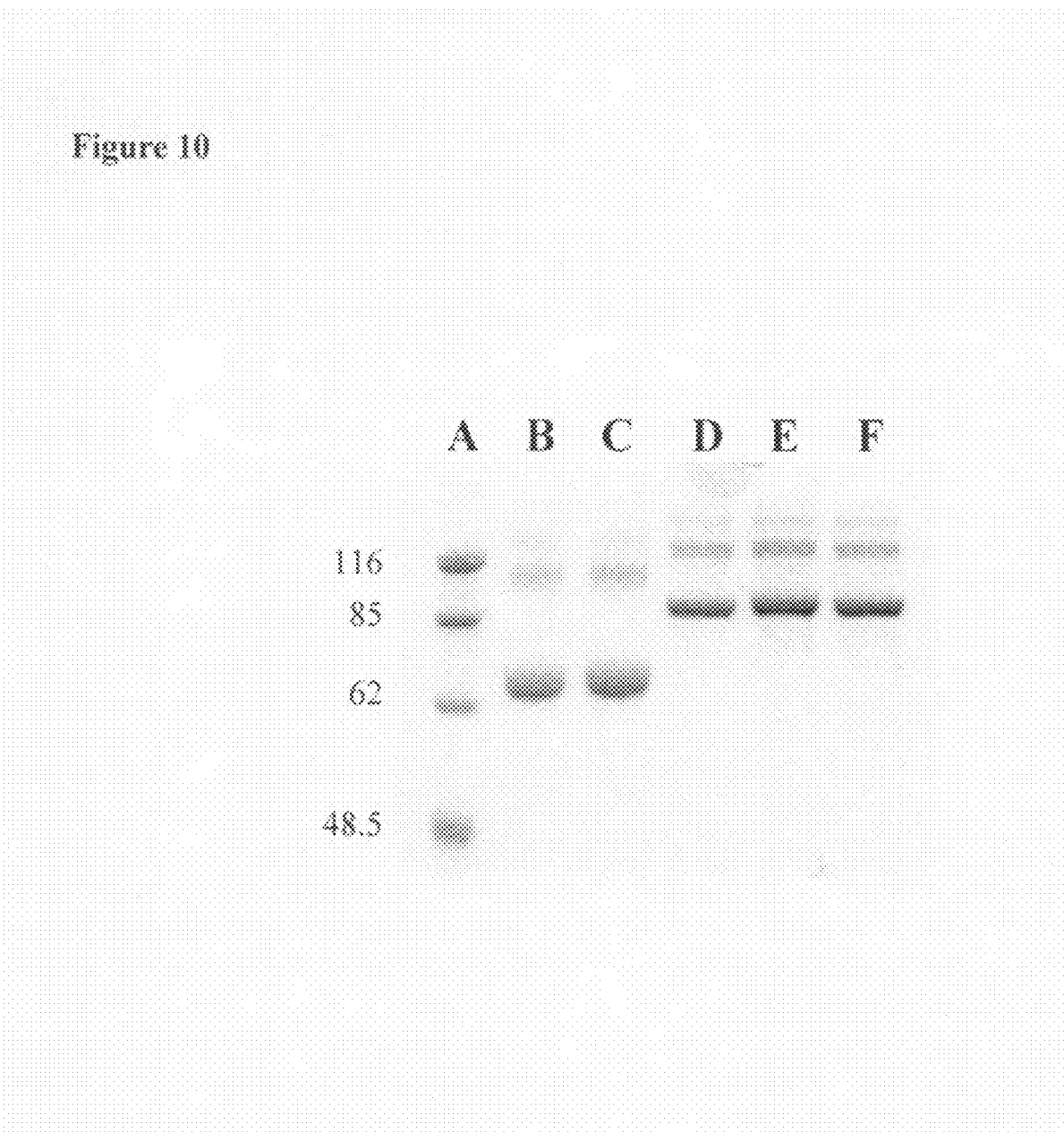
FIG. 10 shows a SDS-PAGE of purified HSA-CPSFs. Each lane was loaded with about 20 μg of protein. A), HSA (65 Kd) from blood plasma; B), HSA (65 Kd) from yeast; C), HSA/hG-CSF (84.2 Kd); D), HSA/hEPO(83.5 Kd); E), HSA/hIL-11(84.5 Kd).

In this example, it is shown that expression and scale-up are much easier by using a *Pichia* system than other currently available systems. After *Pichia* recombinants were isolated, expression of both Mut+ and Mut$^S$ recombinants was tested. This involved growing a small culture of each recombinant, inducing with methanol, and taking sample at different time points. For secretory expression, both the cell pellet and supernatant were analyzed from each time point. The samples were analyzed on SDS-PAGE gels by using both Coomassie staining and Western blot. Bioactivities of expressed samples were tested and the expression levels and purity were monitored in each step for production of HSA fusion proteins. FIG. 10 shows a SDS-PAGE of the purity of various HSA-CPSFs fusion proteins.

REFERENCES CITED

| U.S. Patent Documents | | |
|---|---|---|
| 4683293 | July, 1987 | Craig |
| 4847201 | July, 1989 | Kaswasaki, et al. |
| 5292646 | March, 1994 | McCoy, et al. |
| 5371193 | December, 1994 | Bennett, et al. |
| 5457038 | October, 1995 | Trinchieri, et al. |
| 5466781 | November, 1995 | Dorin, et al. |
| 5470569 | November, 1995 | Kaswasaki, et al. |
| 5547933 | August, 1996 | Lin, et al. |
| 5686263 | November, 1997 | Wurm |
| 6022953 | February, 2000 | Ralph, et al. |
| 6160089 | December, 2000 | Honjo, et al. |
| 6162467 | December, 2000 | Baumann, et al. (*) |
| 6165470 | December, 2000 | Becquart, et al. |
| 6207802 | March, 2001 | Zsebo, et al. |
| 6254870 | July, 2001 | Staten, et al. |
| 6258559 | July, 2001 | Zamost |
| 6300314 | October, 2001 | Wallner, et al. |
| 6309632 | October, 2001 | Agosti |
| 6322779 | November, 2001 | Halenbeck, et al. |
| 6326198 | December, 2001 | Emerson, et al. |
| Foreign Patent Documents | | |
| WO01/79271 | October, 2001 | Balance et al. |
| WO01/79442 | October, 2001 | Rosen and Haseltin |

OTHER REFERENCES

Testa, et al., Exp. Hematol., 8(Supp. 8), 144-152 (1980).
Tong, et al., J. Biol. Chem., 256(24), 12666-12672 (1981).
Goldwasser, J. Cell. Physiol., 110(Supp 1), 133-135 (1982).
Finch, Blood, 60(6), 1241-1246 (1982);
Sytowski, et al., Exp. Hematol., 8(Supp 8), 52-64 (1980).
Naughton, Ann. Clin. Lab. Sci., 13(5), 432-438 (1983).
Weiss, et al., Am. J. Vet. Res., 44(10), 1832-1835 (1983).
Lappin, et al., Exp. Hematol., 11(7), 661-666 (1983).
Baciu, et al., Ann. N.Y. Acad. Sci., 414, 66-72 (1983).
Murphy, et al., Acta. Haematologica *Japonica,* 46(7), 1380-1396 (1983).
Dessypris, et al., Brit. J. Haematol, 56, 295-306 (1984).
Emmanouel, et al., Am. J. Physiol., 247 (1 Pt 2), F1 68-76 (1984).
Lin, F K et al., "Cloning and expression of human erythropoietin gene", Proc. Natl. Acad.
Sci. USA., 82(22):7580-7584 (1985).
Sanger et al., Proc. Natl. Acad. Sci. USA, 74:5463-5467, 1977)
Saiki, R. K. et al, Science 230:1350-1354, 1985
Maniatis T et al., "Molecular cloning, a Laboratory Manual", Cold Spring Harbor
laboratory, Cold Spring Harbor, N.Y., 1982
Ellis et al., 1985; Koutz et al., 1989; Tschopp et al., 1987a (*Pichia* manu)
Watanabe, et al., Pharm Res 2001 December:18(12):1775.
Kobayashi, K et al., Ther Apher, November:2(4):257-62, 1998.(*Pichia*)
Buckholz and Gleeson, 1991; Cregg and Higgins, 1995 (*Pichia*)

Metcalf, D., Blood, 67, 257, 1986
Mufson, R. A. et al., Cellular Immunol., 119, 182, 1989
Wong, G., et al., Science, 228, 810, 1986.
Metcalf, D., Blood, 67, 257, 1986.
Hattersley, G., et al., J. Cell Physiol., 137, 199, 1988.
Nicola, N., Immunol. Today, 8, 134, 1987.
Kitamura, T., et al., J. cell Physiol., 140, 323, 1989.
Kawasaki, E. S., et al., Science, 230, 291, 1985.
Morrison, "Bioprocessing in Space—an Overview", pp. 557-571 in The World Biotech REPOrt 1984, Volume 2:USA, (Online Publications, New York, N.Y. 1984).
Vedovato, et al., Acta. Haematol, 71, 211-213 (1984)
Vichinsky, et al., J. Pediatr., 105(1), 15-21 (1984)
Cotes, et al., Brit. J. Obstet. Gynaecol., 90(4), 304-311 (1983)
Haga, et al., Acta. Pediatr. Scand., 72, 827-831 (1983)
Claus-Walker, et al., Arch. Phys. Med. Rehabil., 65, 370-374 (1984)
Dunn, et al., Eur. J. Appl. Physiol., 52, 178-182 (1984)
Miller, et al., Brit. J. Haematol., 52, 545-590 (1982)
Udupa, et al., J. Lab. Clin. Med., 103(4), 574-580 and 581-588 (1984);
Lipschitz, et al., Blood, 63(3), 502-509 (1983)
Dainiak, et al., Cancer, 51(6), 1101-1106 (1983)
Schwartz, et al., Otolaryngol., 109, 269-272 (1983)
Pennathur-Das, et al., Blood, 63(5), 1168-71 (1984)
Haddy, Am. Jour. Ped. Hematol./Oncol., 4, 191-196, (1982)
Eschbach, et al. J. Clin. Invest., 74(2), pp. 434-441, (1984
Krane, Henry Ford Hosp. Med. J., 31(3), 177-181 (1983).

What is claimed is:

1. A human serum albumin-erythropoietin (HSA-EPO) fusion protein comprising: (a) the amino acid sequence of SEQ ID NO: 6; (b) the amino acid sequence encoded by the polynucleotide, of SEQ ID NO: 5; or (c) the amino acid sequence encoded by the polynucleotide contained in the yeast strain designated as YZ-HSA/hEPO in ATCC® Deposit No: PTA-4607, said HSA-EPO fusion protein having a plasma half-life longer than a plasma half-life of erythropoietin.

2. The HSA-EPO fusion protein of claim 1, wherein said fusion protein is a human serum albumin-human erythropoietin fusion protein.

3. The HSA-EPO fusion protein of claim 1, wherein said HSA-EPO fusion protein has a shelf-life four times longer than a shelf-life of erythropoietin.

4. The HSA-EPO fusion protein of claim 1, wherein said HSA-EPO fusion protein has said plasma half-life four times longer than said plasma half-life of erythropoietin.

5. A composition comprising said HSA-EPO fusion protein of claim 1 and a pharmaceutically acceptable excipient.

6. The composition of claim 5 further comprising a human serum albumin-human interleukin-11 fusion protein (HSA-IL-11 fusion protein).

7. The composition of claim 5 further comprising a human serum albumin-human interleukin-3 fusion protein (HSA-IL-3 fusion protein).

* * * * *